US005739026A

United States Patent [19]

Garoff et al.

[11] Patent Number: 5,739,026
[45] Date of Patent: Apr. 14, 1998

[54] DNA EXPRESSION SYSTEMS BASED ON ALPHAVIRUSES

[75] Inventors: Henrik Garoff, Hägersten; Peter Liljeström, Huddinge, both of Sweden

[73] Assignee: Bioption AB, Tullinge, Sweden

[21] Appl. No.: 920,281

[22] PCT Filed: Dec. 12, 1991

[86] PCT No.: PCT/SE91/00855

§ 371 Date: Aug. 13, 1992

§ 102(e) Date: Aug. 13, 1992

[87] PCT Pub. No.: WO92/10578

PCT Pub. Date: Jun. 25, 1992

[30] Foreign Application Priority Data

Dec. 13, 1990 [SE] Sweden ................... 9003978

[51] Int. Cl.$^6$ ............. C12N 5/10; C12N 15/86; C12N 15/40
[52] U.S. Cl. ............ 435/240.2; 435/320.1; 536/23.72; 536/24.1
[58] Field of Search ............ 435/235.1, 69.1, 435/172.1, 240.2, 320.1, 172.3; 536/23.72, 24.1, 23.1; 935/22, 32, 52, 55, 57

[56] References Cited

FOREIGN PATENT DOCUMENTS 0194809 9/1986 European Pat. Off. .
WO8912095 12/1989 WIPO .

OTHER PUBLICATIONS

Jalanko et al. (1985), *Virology* 141:257–266.
Käärläinen et al. (1982), *Virology* 113:686–697.
Kuhn et al. (1990) *J. Virol.* 64:1465–1476.
Kuhn et al. (1991) *Virology* 182:430–441.
Niesters et al. (1990) *J. Virol.* 64:4162–4168.
Niesters et al. (1990) *J. Virol.* 64:1639–1647.
Ou et al. (1981) *Virology* 109:281–289.
Ou et al. (1982 *J.Mol.Biol.* 156:719–730.
Strauss et al., pp. 205–234 in *Virus Structure and Assembly* S. Casjens, ed., c. 1985 by Jones and Bartlett, Boston, MA.
Weiss et al. (1989) *J.Virol.* 63:5310–5318.
Hahn et al. (1988) *Proc. Natl. Acad. Sci. USA* 85:5997–6001.
Ou et al. (1983) *J. Mol. Biol.* 168:1–15.
Alphaviruses –A new vector expressing heterologous genes, in Vopr. Virusol, Jul.–Aug. 1988, 33(4) pp. 502–504.
Levis et al, (1987), Proc. Nat'l Academy of Science, vol. 84, pp. 4811–4815, *Biochemistry*.
Xiong et al, (1989) *Science* vol. 243, pp. 1188–1191.
K. Takkinen (1986) *Nucleic Acids Research*, vol. 14, No. 14, pp. 5667–5682.
Garoff et al, (1982) in Cooper et al, eds, *Current Topics in Microbiology and Immunology*, Springer–Verlag, New York, pp. 1–50.
"Sandles Virus: An Efficient, Broad Host Range Vector for Gene Expression in Animal Cells", Xiong et al. Science, vol. 243, pp. 1188–1191, Mar. 3, 1989.

*Primary Examiner*—David Guzo
*Attorney, Agent, or Firm*—Birch, Stewart, Kolasch & Birch, LLP

[57] ABSTRACT

The disclosure describes recombinant alphavirus RNA molecules and expression of heterologous proteins therefrom in animal cells. Recombinant alphaviruses of the present invention, when made to express an antigenic protein, can be administered as vaccines.

48 Claims, 35 Drawing Sheets

Fig. 5A

```
GATGGCGGAT GTGTGACATA CACGACGCCA AAAGATTTTG TTCCAGCTCC TGCCACCTCC

GCTACGCGAG AGATTAACCA CCCACG ATG GCC GCC AAA GTG CAT GTT GAT ATT
                             Met Ala Ala Lys Val His Val Asp Ile
                                                         5
```

| | | | | | | | | | | | | | | |
|---|---|---|---|---|---|---|---|---|---|---|---|---|---|---|
| GAG | GCT | GAC | AGC | CCA | TTC | ATC | AAG | TCT | TTG | CAG | AAG | GCA | TTT | CCG | 158
| Glu | Ala | Asp | Ser | Pro | Phe | Ile | Lys | Ser | Leu | Gln | Lys | Ala | Phe | Pro |
| 10 | | | | | 15 | | | | | 20 | | | | |

```
TCG TTC GAG GTG GAG TCA TTG CAG GTC ACA CCA AAT GAC CAT GCA     203
Ser Phe Glu Val Glu Ser Leu Gln Val Thr Pro Asn Asp His Ala
 25              30                  35

AAT GCC AGA GCA TTT TCG CAC CTG GCT ACC AAA TTG ATC GAG CAG     248
Asn Ala Arg Ala Phe Ser His Leu Ala Thr Lys Leu Ile Glu Gln
 40                  45                  50

GAG ACT GAC AAA GAC ACA CTC ATC TTG GAT ATC GGC AGT GCG CCT     293
Glu Thr Asp Lys Asp Thr Leu Ile Leu Asp Ile Gly Ser Ala Pro
 55                  60                  65

TCC AGG AGA ATG ATG TCT ACG CAC AAA TAC CAC TGC GTA TGC CCT     338
Ser Arg Arg Met Met Ser Thr His Lys Tyr His Cys Val Cys Pro
 70                  75                  80

ATG CGC AGC GCA GAA GAC CCC GAA AGG CTC GAT AGC TAC GCA AAG     383
Met Arg Ser Ala Glu Asp Pro Glu Arg Leu Asp Ser Tyr Ala Lys
 85                  90                  95

AAA CTG GCA GCG GCC TCC GGG AAG GTG CTG GAT AGA GAG ATC GCA     428
Lys Leu Ala Ala Ala Ser Gly Lys Val Leu Asp Arg Glu Ile Ala
100                 105                 110

GGA AAA ATC ACC GAC CTG CAG ACC GTC ATG GCT ACG CCA GAC GCT     473
Gly Lys Ile Thr Asp Leu Gln Thr Val Met Ala Thr Pro Asp Ala
115                 120                 125

GAA TCT CCT ACC TTT TGC CTG CAT ACA GAC GTC ACG TGT CGT ACG     518
Glu Ser Pro Thr Phe Cys Leu His Thr Asp Val Thr Cys Arg Thr
130                 135                 140

GCA GCC GAA GTG GCC GTA TAC CAG GAC GTG TAT GCT GTA CAT GCA     563
Ala Ala Glu Val Ala Val Tyr Gln Asp Val Tyr Ala Val His Ala
145                 150                 155

CCA ACA TCG CTG TAC CAT CAG GCG ATG AAA GGT GTC AGA ACG GCG     608
Pro Thr Ser Leu Tyr His Gln Ala Met Lys Gly Val Arg Thr Ala
160                 165                 170

TAT TGG ATT GGG TTT GAC ACC ACC CCG TTT ATG TTT GAC GCG CTA     653
Tyr Trp Ile Gly Phe Asp Thr Thr Pro Phe Met Phe Asp Ala Leu
175                 180                 185

GCA GGC GCG TAT CCA ACC TAC GCC ACA AAC TGG GCC GAC GAG CAG     698
Ala Gly Ala Tyr Pro Thr Tyr Ala Thr Asn Trp Ala Asp Glu Gln
190                 195                 200
```

Fig. 5B

| | | | | | | | | | | | | |
|---|---|---|---|---|---|---|---|---|---|---|---|---|
| GTG | TTA | CAG | GCC | AGG | AAC | ATA | GGA | CTG | TGT | GCA | GCA | TCC | TTG | ACT | 743 |
| Val | Leu | Gln | Ala | Arg | Asn | Ile | Gly | Leu | Cys | Ala | Ala | Ser | Leu | Thr | |
| 205 | | | | 210 | | | | 215 | | | | | | | |

```
GTG TTA CAG GCC AGG AAC ATA GGA CTG TGT GCA GCA TCC TTG ACT   743
Val Leu Gln Ala Arg Asn Ile Gly Leu Cys Ala Ala Ser Leu Thr
205             210             215

GAG GGA AGA CTC GGC AAA CTG TCC ATT CTC CGC AAG AAG CAA TTG   788
Glu Gly Arg Leu Gly Lys Leu Ser Ile Leu Arg Lys Lys Gln Leu
220             225             230

AAA CCT TGC GAC ACA GTC ATG TTC TCG GTA GGA TCT ACA TTG TAC   833
Lys Pro Cys Asp Thr Val Met Phe Ser Val Gly Ser Thr Leu Tyr
235             240             245

ACT GAG AGC AGA AAG CTA CTG AGG AGC TGG CAC TTA CCC TCC GTA   878
Thr Glu Ser Arg Lys Leu Leu Arg Ser Trp His Leu Pro Ser Val
250             255             260

TTC CAC CTG AAA GGT AAA CAA TCC TTT ACC TGT AGG TGC GAT ACC   923
Phe His Leu Lys Gly Lys Gln Ser Phe Thr Cys Arg Cys Asp Thr
265             270             275

ATC GTA TCA TGT GAA GGG TAC GTA GTT AAG AAA ATC ACT ATG TGC   968
Ile Val Ser Cys Glu Gly Tyr Val Val Lys Lys Ile Thr Met Cys
280             285             290

CCC GGC CTG TAC GGT AAA ACG GTA GGG TAC GCC GTG ACG TAT CAC   1013
Pro Gly Leu Tyr Gly Lys Thr Val Gly Tyr Ala Val Thr Tyr His
295             300             305

GCG GAG GGA TTC CTA GTG TGC AAG ACC ACA GAC ACT GTC AAA GGA   1058
Ala Glu Gly Phe Leu Val Cys Lys Thr Thr Asp Thr Val Lys Gly
310             315             320

GAA AGA GTC TCA TTC CCT GTA TGC ACC TAC GTC CCC TCA ACC ATC   1103
Glu Arg Val Ser Phe Pro Val Cys Thr Tyr Val Pro Ser Thr Ile
325             330             335

TGT GAT CAA ATG ACT GGC ATA CTA GCG ACC GAC GTC ACA CCG GAG   1148
Cys Asp Gln Met Thr Gly Ile Leu Ala Thr Asp Val Thr Pro Glu
340             345             350

GAC GCA CAG AAG TTG TTA GTG GGA TTG AAT CAG AGG ATA GTT GTG   1193
Asp Ala Gln Lys Leu Leu Val Gly Leu Asn Gln Arg Ile Val Val
355             360             365

AAC GGA AGA ACA CAG CGA AAC ACT AAC ACG ATG AAG AAC TAT CTG   1238
Asn Gly Arg Thr Gln Arg Asn Thr Asn Thr Met Lys Asn Tyr Leu
370             375             380

CTT CCG ATT GTG GCC GTC GCA TTT AGC AAG TGG GCG AGG GAA TAC   1283
Leu Pro Ile Val Ala Val Ala Phe Ser Lys Trp Ala Arg Glu Tyr
385             390             395

AAG GCA GAC CTT GAT GAT GAA AAA CCT CTG GGT GTC CGA GAG AGG   1328
Lys Ala Asp Leu Asp Asp Glu Lys Pro Leu Gly Val Arg Glu Arg
400             405             410

TCA CTT ACT TGC TGC TGC TTG TGG GCA TTT AAA ACG AGG AAG ATG   1373
Ser Leu Thr Cys Cys Cys Leu Trp Ala Phe Lys Thr Arg Lys Met
415             420             425
```

Fig. 5C

```
CAC ACC ATG TAC AAG AAA CCA GAC ACC CAG ACA ATA GTG AAG GTG   1418
His Thr Met Tyr Lys Lys Pro Asp Thr Gln Thr Ile Val Lys Val
430             435             440

CCT TCA GAG TTT AAC TCG TTC GTC ATC CCG AGC CTA TGG TCT ACA   1463
Pro Ser Glu Phe Asn Ser Phe Val Ile Pro Ser Leu Trp Ser Thr
445             450             455

GGC CTC GCA ATC CCA GTC AGA TCA CGC ATT AAG ATG CTT TTG GCC   1508
Gly Leu Ala Ile Pro Val Arg Ser Arg Ile Lys Met Leu Leu Ala
460             465             470

AAG AAG ACC AAG CGA GAG TTA ATA CCT GTT CTC GAC GCG TCG TCA   1553
Lys Lys Thr Lys Arg Glu Leu Ile Pro Val Leu Asp Ala Ser Ser
475             480             485

GCC AGG GAT GCT GAA CAA GAG GAG AAG GAG AGG TTG GAG GCC GAG   1598
Ala Arg Asp Ala Glu Gln Glu Glu Lys Glu Arg Leu Glu Ala Glu
490             495             500

CTG ACT AGA GAA GCC TTA CCA CCC CTC GTC CCC ATC GCG CCG GCG   1643
Leu Thr Arg Glu Ala Leu Pro Pro Leu Val Pro Ile Ala Pro Ala
505             510             515

GAG ACG GGA GTC GTC GAC GTC GAC GTT GAA GAA CTA GAG TAT CAC   1688
Glu Thr Gly Val Val Asp Val Asp Val Glu Glu Leu Glu Tyr His
520             525             530

GCA GGT GCA GGG GTC GTG GAA ACA CCT CGC AGC GCG TTG AAA GTC   1733
Ala Gly Ala Gly Val Val Glu Thr Pro Arg Ser Ala Leu Lys Val
535             540             545

ACC GCA CAG CCG AAC GAC GTA CTA CTA GGA AAT TAC GTA GTT CTG   1778
Thr Ala Gln Pro Asn Asp Val Leu Leu Gly Asn Tyr Val Val Leu
550             555             560

TCC CCG CAG ACC GTG CTC AAG AGC TCC AAG TTG GCC CCC GTG CAC   1823
Ser Pro Gln Thr Val Leu Lys Ser Ser Lys Leu Ala Pro Val His
565             570             575

CCT CTA GCA GAG CAG GTG AAA ATA ATA ACA CAT AAC GGG AGG GCC   1868
Pro Leu Ala Glu Gln Val Lys Ile Ile Thr His Asn Gly Arg Ala
580             585             590

GGC GGT TAC CAG GTC GAC GGA TAT GAC GGC AGG GTC CTA CTA CCA   1913
Gly Gly Tyr Gln Val Asp Gly Tyr Asp Gly Arg Val Leu Leu Pro
595             600             605

TGT GGA TCG GCC ATT CCG GTC CCT GAG TTT CAA GCT TTG AGC GAG   1958
Cys Gly Ser Ala Ile Pro Val Pro Glu Phe Gln Ala Leu Ser Glu
610             615             620

AGC GCC ACT ATG GTG TAC AAC GAA AGG GAG TTC GTC AAC AGG AAA   2003
Ser Ala Thr Met Val Tyr Asn Glu Arg Glu Phe Val Asn Arg Lys
625             630             635

CTA TAC CAT ATT GCC GTT CAC GGA CCG TCG CTG AAC ACC GAC GAG   2048
Leu Tyr His Ile Ala Val His Gly Pro Ser Leu Asn Thr Asp Glu
640             645             650
```

Fig. 5D

```
GAG AAC TAC GAG AAA GTC AGA GCT GAA AGA ACT GAC GCC GAG TAC    2093
Glu Asn Tyr Glu Lys Val Arg Ala Glu Arg Thr Asp Ala Glu Tyr
655             660             665

GTG TTC GAC GTA GAT AAA AAA TGC TGC GTC AAG AGA GAG GAA GCG    2138
Val Phe Asp Val Asp Lys Lys Cys Cys Val Lys Arg Glu Glu Ala
670             675             680

TCG GGT TTG GTG TTG GTG GGA GAG CTA ACC AAC CCC CCG TTC CAT    2183
Ser Gly Leu Val Leu Val Gly Glu Leu Thr Asn Pro Pro Phe His
685             690             695

GAA TTC GCC TAC GAA GGG CTG AAG ATC AGG CCG TCG GCA CCA TAT    2228
Glu Phe Ala Tyr Glu Gly Leu Lys Ile Arg Pro Ser Ala Pro Tyr
700             705             710

AAG ACT ACA GTA GTA GGA GTC TTT GGG GTT CCG GGA TCA GGC AAG    2273
Lys Thr Thr Val Val Gly Val Phe Gly Val Pro Gly Ser Gly Lys
715             720             725

TCT GCT ATT ATT AAG AGC CTC GTG ACC AAA CAC GAT CTG GTC ACC    2318
Ser Ala Ile Ile Lys Ser Leu Val Thr Lys His Asp Leu Val Thr
730             735             740

AGC GGC AAG AAG GAG AAC TGC CAG GAA ATA GTT AAC GAC GTG AAG    2363
Ser Gly Lys Lys Glu Asn Cys Gln Glu Ile Val Asn Asp Val Lys
745             750             755

AAG CAC CGC GGG AAG GGG ACA AGT AGG GAA AAC AGT GAC TCC ATC    2408
Lys His Arg Gly Lys Gly Thr Ser Arg Glu Asn Ser Asp Ser Ile
760             765             770

CTG CTA AAC GGG TGT CGT CGT GCC GTG GAC ATC CTA TAT GTG GAC    2453
Leu Leu Asn Gly Cys Arg Arg Ala Val Asp Ile Leu Tyr Val Asp
775             780             785

GAG GCT TTC GCT TGC CAT TCC GGT ACT CTG CTG GCC CTA ATT GCT    2498
Glu Ala Phe Ala Cys His Ser Gly Thr Leu Leu Ala Leu Ile Ala
790             795             800

CTT GTT AAA CCT CGG AGC AAA GTG GTG TTA TGC GGA GAC CCC AAG    2543
Leu Val Lys Pro Arg Ser Lys Val Val Leu Cys Gly Asp Pro Lys
805             810             815

CAA TGC GGA TTC TTC AAT ATG ATG CAG CTT AAG GTG AAC TTC AAC    2588
Gln Cys Gly Phe Phe Asn Met Met Gln Leu Lys Val Asn Phe Asn
820             825             830

CAC AAC ATC TGC ACT GAA GTA TGT CAT AAA AGT ATA TCC AGA CGT    2633
His Asn Ile Cys Thr Glu Val Cys His Lys Ser Ile Ser Arg Arg
835             840             845

TGC ACG CGT CCA GTC ACG GCC ATC GTG TCT ACG TTG CAC TAC GGA    2678
Cys Thr Arg Pro Val Thr Ala Ile Val Ser Thr Leu His Tyr Gly
850             855             860

GGC AAG ATG CGC ACG ACC AAC CCG TGC AAC AAA CCC ATA ATC ATA    2723
Gly Lys Met Arg Thr Thr Asn Pro Cys Asn Lys Pro Ile Ile Ile
865             870             875
```

Fig. 5E

```
GAC ACC ACA GGA CAG ACC AAG CCC AAG CCA GGA GAC ATC GTG TTA    2768
Asp Thr Thr Gly Gln Thr Lys Pro Lys Pro Gly Asp Ile Val Leu
880             885             890

ACA TGC TTC CGA GGC TGG GCA AAG CAG CTG CAG TTG GAC TAC CGT    2813
Thr Cys Phe Arg Gly Trp Ala Lys Gln Leu Gln Leu Asp Tyr Arg
895             900             905

GGA CAC GAA GTC ATG ACA GCA GCA GCA TCT CAG GGC CTC ACC CGC    2858
Gly His Glu Val Met Thr Ala Ala Ala Ser Gln Gly Leu Thr Arg
910             915             920

AAA GGG GTA TAC GCC GTA AGG CAG AAG GTG AAT GAA AAT CCC TTG    2903
Lys Gly Val Tyr Ala Val Arg Gln Lys Val Asn Glu Asn Pro Leu
925             930             935

TAT GCC CCT GCG TCG GAG CAC GTG AAT GTA CTG CTG ACG CGC ACT    2948
Tyr Ala Pro Ala Ser Glu His Val Asn Val Leu Leu Thr Arg Thr
940             945             950

GAG GAT AGG CTG GTG TGG AAA ACG CTG GCC GGC GAT CCC TGG ATT    2993
Glu Asp Arg Leu Val Trp Lys Thr Leu Ala Gly Asp Pro Trp Ile
955             960             965

AAG GTC CTA TCA AAC ATT CCA CAG GGT AAC TTT ACG GCC ACA TTG    3038
Lys Val Leu Ser Asn Ile Pro Gln Gly Asn Phe Thr Ala Thr Leu
970             975             980

GAA GAA TGG CAA GAA GAA CAC GAC AAA ATA ATG AAG GTG ATT GAA    3083
Glu Glu Trp Gln Glu Glu His Asp Lys Ile Met Lys Val Ile Glu
985             990             995

GGA CCG GCT GCG CCT GTG GAC GCG TTC CAG AAC AAA GCG AAC GTG    3128
Gly Pro Ala Ala Pro Val Asp Ala Phe Gln Asn Lys Ala Asn Val
1000            1005            1010

TGT TGG GCG AAA AGC CTG GTG CCT GTC CTG GAC ACT GCC GGA ATC    3173
Cys Trp Ala Lys Ser Leu Val Pro Val Leu Asp Thr Ala Gly Ile
1015            1020            1025

AGA TTG ACA GCA GAG GAG TGG AGC ACC ATA ATT ACA GCA TTT AAG    3218
Arg Leu Thr Ala Glu Glu Trp Ser Thr Ile Ile Thr Ala Phe Lys
1030            1035            1040

GAG GAC AGA GCT TAC TCT CCA GTG GTG GCC TTG AAT GAA ATT TGC    3263
Glu Asp Arg Ala Tyr Ser Pro Val Val Ala Leu Asn Glu Ile Cys
1045            1050            1055

ACC AAG TAC TAT GGA GTT GAC CTG GAC AGT GGC CTG TTT TCT GCC    3308
Thr Lys Tyr Tyr Gly Val Asp Leu Asp Ser Gly Leu Phe Ser Ala
1060            1065            1070

CCG AAG GTG TCC CTG TAT TAC GAG AAC AAC CAC TGG GAT AAC AGA    3353
Pro Lys Val Ser Leu Tyr Tyr Glu Asn Asn His Trp Asp Asn Arg
1075            1080            1085

CCT GGT GGA AGG ATG TAT GGA TTC AAT GCC GCA ACA GCT GCC AGG    3398
Pro Gly Gly Arg Met Tyr Gly Phe Asn Ala Ala Thr Ala Ala Arg
1090            1095            1100
```

Fig. 5F

```
CTG GAA GCT AGA CAT ACC TTC CTG AAG GGG CAG TGG CAT ACG GGC    3443
Leu Glu Ala Arg His Thr Phe Leu Lys Gly Gln Trp His Thr Gly
1105              1110              1115

AAG CAG GCA GTT ATC GCA GAA AGA AAA ATC CAA CCG CTT TCT GTG    3488
Lys Gln Ala Val Ile Ala Glu Arg Lys Ile Gln Pro Leu Ser Val
1120              1125              1130

CTG GAC AAT GTA ATT CCT ATC AAC CGC AGG CTG CCG CAC GCC CTG    3533
Leu Asp Asn Val Ile Pro Ile Asn Arg Arg Leu Pro His Ala Leu
1135              1140              1145

GTG GCT GAG TAC AAG ACG GTT AAA GGC AGT AGG GTT GAG TGG CTG    3578
Val Ala Glu Tyr Lys Thr Val Lys Gly Ser Arg Val Glu Trp Leu
1150              1155              1160

GTC AAT AAA GTA AGA GGG TAC CAC GTC CTG CTG GTG AGT GAG TAC    3623
Val Asn Lys Val Arg Gly Tyr His Val Leu Leu Val Ser Glu Tyr
1165              1170              1175

AAC CTG GCT TTG CCT CGA CGC AGG GTC ACT TGG TTG TCA CCG CTG    3668
Asn Leu Ala Leu Pro Arg Arg Arg Val Thr Trp Leu Ser Pro Leu
1180              1185              1190

AAT GTC ACA GGC GCC GAT AGG TGC TAC GAC CTA AGT TTA GGA CTG    3713
Asn Val Thr Gly Ala Asp Arg Cys Tyr Asp Leu Ser Leu Gly Leu
1195              1200              1205

CCG GCT GAC GCC GGC AGG TTC GAC TTG GTC TTT GTG AAC ATT CAC    3758
Pro Ala Asp Ala Gly Arg Phe Asp Leu Val Phe Val Asn Ile His
1210              1215              1220

ACG GAA TTC AGA ATC CAC CAC TAC CAG CAG TGT GTC GAC CAC GCC    3803
Thr Glu Phe Arg Ile His His Tyr Gln Gln Cys Val Asp His Ala
1225              1230              1235

ATG AAG CTG CAG ATG CTT GGG GGA GAT GCG CTA CGA CTG CTA AAA    3848
Met Lys Leu Gln Met Leu Gly Gly Asp Ala Leu Arg Leu Leu Lys
1240              1245              1250

CCC GGC GGC ATC TTG ATG AGA GCT TAC GGA TAC GCC GAT AAA ATC    3893
Pro Gly Gly Ile Leu Met Arg Ala Tyr Gly Tyr Ala Asp Lys Ile
1255              1260              1265

AGC GAA GCC GTT GTT TCC TCC TTA AGC AGA AAG TTC TCG TCT GCA    3938
Ser Glu Ala Val Val Ser Ser Leu Ser Arg Lys Phe Ser Ser Ala
1270              1275              1280

AGA GTG TTG CGC CCG GAT TGT GTC ACC AGC AAT ACA GAA GTG TTC    3983
Arg Val Leu Arg Pro Asp Cys Val Thr Ser Asn Thr Glu Val Phe
1285              1290              1295

TTG CTG TTC TCC AAC TTT GAC AAC GGA AAG AGA CCC TCT ACG CTA    4028
Leu Leu Phe Ser Asn Phe Asp Asn Gly Lys Arg Pro Ser Thr Leu
1300              1305              1310

CAC CAG ATG AAT ACC AAG CTG AGT GCC GTG TAT GCC GGA GAA GCC    4073
His Gln Met Asn Thr Lys Leu Ser Ala Val Tyr Ala Gly Glu Ala
1315              1320              1325
```

Fig. 5G

```
ATG CAC ACG GCC GGG TGT GCA CCA TCC TAC AGA GTT AAG AGA GCA    4118
Met His Thr Ala Gly Cys Ala Pro Ser Tyr Arg Val Lys Arg Ala
1330          1335              1340

GAC ATA GCC ACG TGC ACA GAA GCG GCT GTG GTT AAC GCA GCT AAC    4163
Asp Ile Ala Thr Cys Thr Glu Ala Ala Val Val Asn Ala Ala Asn
1345          1350              1355

GCC CGT GGA ACT GTA GGG GAT GGC GTA TGC AGG GCC GTG GCG AAG    4208
Ala Arg Gly Thr Val Gly Asp Gly Val Cys Arg Ala Val Ala Lys
1360          1365              1370

AAA TGG CCG TCA GCC TTT AAG GGA GCA GCA ACA CCA GTG GGC ACA    4253
Lys Trp Pro Ser Ala Phe Lys Gly Ala Ala Thr Pro Val Gly Thr
1375          1380              1385

ATT AAA ACA GTC ATG TGC GGC TCG TAC CCC GTC ATC CAC GCT GTA    4298
Ile Lys Thr Val Met Cys Gly Ser Tyr Pro Val Ile His Ala Val
1390          1395              1400

GCG CCT AAT TTC TCT GCC ACG ACT GAA GCG GAA GGG GAC CGC GAA    4343
Ala Pro Asn Phe Ser Ala Thr Thr Glu Ala Glu Gly Asp Arg Glu
1405          1410              1415

TTG GCC GCT GTC TAC CGG GCA GTG GCC GCC GAA GTA AAC AGA CTG    4388
Leu Ala Ala Val Tyr Arg Ala Val Ala Ala Glu Val Asn Arg Leu
1420          1425              1430

TCA CTG AGC AGC GTA GCC ATC CCG CTG CTG TCC ACA GGA GTG TTC    4433
Ser Leu Ser Ser Val Ala Ile Pro Leu Leu Ser Thr Gly Val Phe
1435          1440              1445

AGC GGC GGA AGA GAT AGG CTG CAG CAA TCC CTC AAC CAT CTA TTC    4478
Ser Gly Gly Arg Asp Arg Leu Gln Gln Ser Leu Asn His Leu Phe
1450          1455              1460

ACA GCA ATG GAC GCC ACG GAC GCT GAC GTG ACC ATC TAC TGC AGA    4523
Thr Ala Met Asp Ala Thr Asp Ala Asp Val Thr Ile Tyr Cys Arg
1465    -     1470              1475

GAC AAA AGT TGG GAG AAG AAA ATC CAG GAA GCC ATT GAC ATG AGG    4568
Asp Lys Ser Trp Glu Lys Lys Ile Gln Glu Ala Ile Asp Met Arg
1480          1485              1490

ACG GCT GTG GAG TTG CTC AAT GAT GAC GTG GAG CTG ACC ACA GAC    4613
Thr Ala Val Glu Leu Leu Asn Asp Asp Val Glu Leu Thr Thr Asp
1495          1500              1505

TTG GTG AGA GTG CAC CCG GAC AGC AGC CTG GTG GGT CGT AAG GGC    4658
Leu Val Arg Val His Pro Asp Ser Ser Leu Val Gly Arg Lys Gly
1510          1515              1520

TAC AGT ACC ACT GAC GGG TCG CTG TAC TCG TAC TTT GAA GGT ACG    4703
Tyr Ser Thr Thr Asp Gly Ser Leu Tyr Ser Tyr Phe Glu Gly Thr
1525          1530              1535

AAA TTC AAC CAG GCT GCT ATT GAT ATG GCA GAG ATA CTG ACG TTG    4748
Lys Phe Asn Gln Ala Ala Ile Asp Met Ala Glu Ile Leu Thr Leu
1540          1545              1550
```

Fig. 5H

```
TGG CCC AGA CTG CAA GAG GCA AAC GAA CAG ATA TGC CTA TAC CCG   4793
Trp Pro Arg Leu Gln Glu Ala Asn Glu Gln Ile Cys Leu Tyr Ala
1555             1560             1565

CTG GGC GAA ACA ATG GAC AAC ATC AGA TCC AAA TGT CCG GTG AAC   4838
Leu Gly Glu Thr Met Asp Asn Ile Arg Ser Lys Cys Pro Val Asn
1570             1757             1580

GAT TCC GAT TCA TCA ACA CCT CCC AGG ACA GTG CCC TGC CTG TGC   4883
Asp Ser Asp Ser Ser Thr Pro Pro Arg Thr Val Pro Cys Leu Cys
1585             1590             1595

CGC TAC GCA ATG ACA GCA GAA CGG ATC GCC CGC CTT AGG TCA CAC   4928
Arg Tyr Ala Met Thr Ala Glu Arg Ile Ala Arg Leu Arg Ser His
1600             1605             1610

CAA GTT AAA AGC ATG GTG GTT TGC TCA TCT TTT CCC CTC CCG AAA   4973
Gln Val Lys Ser Met Val Val Cys Ser Ser Phe Pro Leu Pro Lys
1615             1620             1625

TAC CAT GTA GAT GGG GTG CAG AAG GTA AAG TGC GAG AAG GTT CTC   5018
Tyr His Val Asp Gly Val Gln Lys Val Lys Cys Glu Lys Val Leu
1630             1635             1640

CTG TTC GAC CCG ACG GTA CCT TCA GTG GTT AGT CCG CGG AAG TAT   5063
Leu Phe Asp Pro Thr Val Pro Ser Val Val Ser Pro Arg Lys Tyr
1645             1650             1655

GCC GCA TCT ACG ACG GAC CAC TCA GAT CGG TCG TTA CGA GGG TTT   5108
Ala Ala Ser Thr Thr Asp His Ser Asp Arg Ser Leu Arg Gly Phe
1660             1665             1670

GAC TTG GAC TGG ACC ACC GAC TCG TCT TCC ACT GCC AGC GAT ACC   5153
Asp Leu Asp Trp Thr Thr Asp Ser Ser Ser Thr Ala Ser Asp Thr
1675             1680             1685

ATG TCG CTA CCC AGT TTG CAG TCG TGT GAC ATC GAC TCG ATC TAC   5198
Met Ser Leu Pro Ser Leu Gln Ser Cys Asp Ile Asp Ser Ile Tyr
1690             1695             1700

GAG CCA ATG GCT CCC ATA GTA GTG ACG GCT GAC GTA CAC CCT GAA   5243
Glu Pro Met Ala Pro Ile Val Val Thr Ala Asp Val His Pro Glu
1705             1710             1715

CCC GCA GGC ATC GCG GAC CTG GCG GCA GAT GTG CAC CCT GAA CCC   5288
Pro Ala Gly Ile Ala Asp Leu Ala Ala Asp Val His Pro Glu Pro
1720             1725             1730

GCA GAC CAT GTG GAC CTC GAG AAC CCG ATT CCT CCA CCG CGC CCG   5333
Ala Asp His Val Asp Leu Glu Asn Pro Ile Pro Pro Pro Arg Pro
1735             1740             1745

AAG AGA GCT GCA TAC CTT GCC TCC CGC GCG GCG GAG CGA CCG GTG   5378
Lys Arg Ala Ala Tyr Leu Ala Ser Arg Ala Ala Glu Arg Pro Val
1750             1755             1760

CCG GCG CCG AGA AAG CCG ACG CCT GCC CCA AGG ACT GCG TTT AGG   5423
Pro Ala Pro Arg Lys Pro Thr Pro Ala Pro Arg Thr Ala Phe Arg
1765             1770             1775
```

Fig. 5I

```
AAC AAG CTG CCT TTG ACG TTC GGC GAC TTT GAC GAG CAC GAG GTC    5468
Asn Lys Leu Pro Leu Thr Phe Gly Asp Phe Asp Glu His Glu Val
1780            1785            1790

GAT GCG TTG GCC TCC GGG ATT ACT TTC GGA GAC TTC GAC GAC GTC    5513
Asp Ala Leu Ala Ser Gly Ile Thr Phe Gly Asp Phe Asp Asp Val
1795            1800            1805

CTG CGA CTA GGC CGC GCG GGT GCA TAT ATT TTC TCC TCG GAC ACT    5558
Leu Arg Leu Gly Arg Ala Gly Ala Tyr Ile Phe Ser Ser Asp Thr
1810            1815            1820

GGC AGC GGA CAT TTA CAA CAA AAA TCC GTT AGG CAG CAC AAT CTC    5603
Gly Ser Gly His Leu Gln Gln Lys Ser Val Arg Gln His Asn Leu
1825            1830            1835

CAG TGC GCA CAA CTG GAT GCG GTC CAG GAG GAG AAA ATG TAC CCG    5648
Gln Cys Ala Gln Leu Asp Ala Val Gln Glu Glu Lys Met Tyr Pro
1840            1845            1850

CCA AAA TTG GAT ACT GAG AGG GAG AAG CTG TTG CTG CTG AAA ATG    5693
Pro Lys Leu Asp Thr Glu Arg Glu Lys Leu Leu Leu Leu Lys Met
1855            1860            1865

CAG ATG CAC CCA TCG GAG GCT AAT AAG AGT CGA TAC CAG TCT CGC    5738
Gln Met His Pro Ser Glu Ala Asn Lys Ser Arg Tyr Gln Ser Arg
1870            1875            1880

AAA GTG GAG AAC ATG AAA GCC ACG GTG GTG GAC AGG CTC ACA TCG    5783
Lys Val Glu Asn Met Lys Ala Thr Val Val Asp Arg Leu Thr Ser
1885            1890            1895

GGG GCC AGA TTG TAC ACG GGA GCG GAC GTA GGC CGC ATA CCA ACA    5828
Gly Ala Arg Leu Tyr Thr Gly Ala Asp Val Gly Arg Ile Pro Thr
1900            1905            1910

TAC GCG GTT CGG TAC CCC CGC CCC GTG TAC TCC CCT ACC GTG ATC    5873
Tyr Ala Val Arg Tyr Pro Arg Pro Val Tyr Ser Pro Thr Val Ile
1915            1920            1925

GAA AGA TTC TCA AGC CCC GAT GTA GCA ATC GCA GCG TGC AAC GAA    5918
Glu Arg Phe Ser Ser Pro Asp Val Ala Ile Ala Ala Cys Asn Glu
1930            1935            1940

TAC CTA TCC AGA AAT TAC CCA ACA GTG GCG TCG TAC CAG ATA ACA    5963
Tyr Leu Ser Arg Asn Tyr Pro Thr Val Ala Ser Tyr Gln Ile Thr
1945            1950            1955

GAT GAA TAC GAC GCA TAC TTG GAC ATG GTT GAC GGG TCG GAT AGT    6008
Asp Glu Tyr Asp Ala Tyr Leu Asp Met Val Asp Gly Ser Asp Ser
1960            1965            1970

TGC TTG GAC AGA GCG ACA TTC TGC CCG GCG AAG CTC CGG TGC TAC    6053
Cys Leu Asp Arg Ala Thr Phe Cys Pro Ala Lys Leu Arg Cys Tyr
1975            1980            1985

CCG AAA CAT CAT GCG TAC CAC CAG CCG ACT GTA CGC AGT GCC GTC    6098
Pro Lys His His Ala Tyr His Gln Pro Thr Val Arg Ser Ala Val
1990            1995            2000
```

Fig. 5J

```
CCG TCA CCC TTT CAG AAC ACA CTA CAG AAC GTG CTA GCG GCC GCC    6143
Pro Ser Pro Phe Gln Asn Thr Leu Gln Asn Val Leu Ala Ala Ala
2005            2010                2015

ACC AAG AGA AAC TGC AAC GTC ACG CAA ATG CGA GAA CTA CCC ACC    6188
Thr Lys Arg Asn Cys Asn Val Thr Gln Met Arg Glu Leu Pro Thr
2020            2025                2030

ATG GAC TCG GCA GTG TTC AAC GTG GAG TGC TTC AAG CGC TAT GCC    6233
Met Asp Ser Ala Val Phe Asn Val Glu Cys Phe Lys Arg Tyr Ala
2035            2040                2045

TGC TCC GGA GAA TAT TGG GAA GAA TAT GCT AAA CAA CCT ATC CGG    6278
Cys Ser Gly Glu Tyr Trp Glu Glu Tyr Ala Lys Gln Pro Ile Arg
2050            2055                2060

ATA ACC ACT GAG AAC ATC ACT ACC TAT GTG ACC AAA TTG AAA GGC    6323
Ile Thr Thr Glu Asn Ile Thr Thr Tyr Val Thr Lys Leu Lys Gly
2065            2070                2075

CCG AAA GCT GCT GCC TTG TTC GCT AAG ACC CAC AAC TTG GTT CCG    6368
Pro Lys Ala Ala Ala Leu Phe Ala Lys Thr His Asn Leu Val Pro
2080            2085                2090

CTG CAG GAG GTT CCC ATG GAC AGA TTC ACG GTC GAC ATG AAA CGA    6413
Leu Gln Glu Val Pro Met Asp Arg Phe Thr Val Asp Met Lys Arg
2095            2100                2105

GAT GTC AAA GTC ACT CCA GGG ACG AAA CAC ACA GAG GAA AGA CCC    6458
Asp Val Lys Val Thr Pro Gly Thr Lys His Thr Glu Glu Arg Pro
2110            2115                2120

AAA GTC CAG GTA ATT CAA GCA GCG GAG CCA TTG GCG ACC GCT TAC    6503
Lys Val Gln Val Ile Gln Ala Ala Glu Pro Leu Ala Thr Ala Tyr
2125            2130                2135

CTG TGC GGC ATC CAC AGG GAA TTA GTA AGG AGA CTA AAT GCT GTG    6548
Leu Cys Gly Ile His Arg Glu Leu Val Arg Arg Leu Asn Ala Val
2140            2145                2150

TTA CGC CCT AAC GTG CAC ACA TTG TTT GAT ATG TCG GCC GAA GAC    6593
Leu Arg Pro Asn Val His Thr Leu Phe Asp Met Ser Ala Glu Asp
2155            2160                2165

TTT GAC GCG ATC ATC GCC TCT CAC TTC CAC CCA GGA GAC CCG GTT    6638
Phe Asp Ala Ile Ile Ala Ser His Phe His Pro Gly Asp Pro Val
2170            2175                2180

CTA GAG ACG GAC ATT GCA TCA TTC GAC AAA AGC CAG GAC GAC TCC    6683
Leu Glu Thr Asp Ile Ala Ser Phe Asp Lys Ser Gln Asp Asp Ser
2185            2190                2195

TTG GCT CTT ACA GGT TTA ATG ATC CTC GAA GAT CTA GGG GTG GAT    6728
Leu Ala Leu Thr Gly Leu Met Ile Leu Glu Asp Leu Gly Val Asp
2200            2205                2210

CAG TAC CTG CTG GAC TTG ATC GAG GCA GCC TTT GGG GAA ATA TCC    6773
Gln Tyr Leu Leu Asp Leu Ile Glu Ala Ala Phe Gly Glu Ile Ser
2215            2220                2225
```

Fig. 5K

```
AGC TGT CAC CTA CCA ACT GGC ACG CGC TTC AAG TTC GGA GCT ATG    6818
Ser Cys His Leu Pro Thr Gly Thr Arg Phe Lys Phe Gly Ala Met
2230             2235             2240

ATG AAA TCG GGC ATG TTT CTG ACT TTG TTT ATT AAC ACT GTT TTG    6863
Met Lys Ser Gly Met Phe Leu Thr Leu Phe Ile Asn Thr Val Leu
2245             2250             2255

AAC ATC ACC ATA GCA AGC AGG GTA CTG GAG CAG AGA CTC ACT GAC    6908
Asn Ile Thr Ile Ala Ser Arg Val Leu Glu Gln Arg Leu Thr Asp
2260             2265             2270

TCC GCC TGT GCG GCC TTC ATC GGC GAC GAC AAC ATC GTT CAC GGA    6953
Ser Ala Cys Ala Ala Phe Ile Gly Asp Asp Asn Ile Val His Gly
2275             2280             2285

GTG ATC TCC GAC AAG CTG ATG GCG GAG AGG TGC GCG TCG TGG GTC    6998
Val Ile Ser Asp Lys Leu Met Ala Glu Arg Cys Ala Ser Trp Val
2290             2295             2300

AAC ATG GAG GTG AAG ATC ATT GAC GCT GTC ATG GGC GAA AAA CCC    7043
Asn Met Glu Val Lys Ile Ile Asp Ala Val Met Gly Glu Lys Pro
2305             2310             2315

CCA TAT TTT TGT GGG GGA TTC ATA GTT TTT GAC AGC GTC ACA CAG    7088
Pro Tyr Phe Cys Gly Gly Phe Ile Val Phe Asp Ser Val Thr Gln
2320             2325             2330

ACC GCC TGC CGT GTT TCA GAC CCA CTT AAG CGC CTG TTC AAG TTG    7133
Thr Ala Cys Arg Val Ser Asp Pro Leu Lys Arg Leu Phe Lys Leu
2335             2340             2345

GGT AAG CCG CTA ACA GCT GAA GAC AAG CAG GAC GAA GAC AGG CGA    7178
Gly Lys Pro Leu Thr Ala Glu Asp Lys Gln Asp Glu Asp Arg Arg
2350             2355             2360

CGA GCA CTG AGT GAC GAG GTT AGC AAG TGG TTC CGG ACA GGC TTG    7223
Arg Ala Leu Ser Asp Glu Val Ser Lys Trp Phe Arg Thr Gly Leu
2365             2370             2375

GGG GCC GAA CTG GAG GTG GCA CTA ACA TCT AGG TAT GAG GTA GAG    7268
Gly Ala Glu Leu Glu Val Ala Leu Thr Ser Arg Tyr Glu Val Glu
2380             2385             2390

GGC TGC AAA AGT ATC CTC ATA GCC ATG ACC ACC TTG GCG AGG GAC    7313
Gly Cys Lys Ser Ile Leu Ile Ala Met Thr Thr Leu Ala Arg Asp
2395             2400             2405

ATT AAG GCG TTT AAG AAA TTG AGA GGA CCT GTT ATA CAC CTC TAC    7358
Ile Lys Ala Phe Lys Lys Leu Arg Gly Pro Val Ile His Leu Tyr
2410             2415             2420

GGC GGT CCT AGA TTG GTG CGT TAATACACAGAAT TCTGATTATA GCGCACTATT 7412
Gly Gly Pro Arg Leu Val Arg
2425             2430

ATAGCACC ATG AAT TAC ATC CCT ACG CAA ACG TTT TAC GGC CGC CGG   7459
         Met Asn Tyr Ile Pro Thr Gln Thr Phe Tyr Gly Arg Arg
              5                  10
```

Fig. 5L

```
TGG CGC CCG CGC CCG GCG GCC CGT CCT TGG CCG TTG CAG GCC ACT    7504
Trp Arg Pro Arg Pro Ala Ala Arg Pro Trp Pro Leu Gln Ala Thr
     15              20              25

CCG GTG GCT CCC GTC GTC CCC GAC TTC CAG GCC CAG CAG ATG CAG    7549
Pro Val Ala Pro Val Val Pro Asp Phe Gln Ala Gln Gln Met Gln
         30              35              40

CAA CTC ATC AGC GCC GTA AAT GCG CTG ACA ATG AGA CAG AAC GCA    7594
Gln Leu Ile Ser Ala Val Asn Ala Leu Thr Met Arg Gln Asn Ala
     45              50              55

ATT GCT CCT GCT AGG CCT CCC AAA CCA AAG AAG AAG AAG ACA ACC    7639
Ile Ala Pro Ala Arg Pro Pro Lys Pro Lys Lys Lys Lys Thr Thr
     60              65              70

AAA CCA AAG CCG AAA ACG CAG CCC AAG AAG ATC AAC GGA AAA ACG    7684
Lys Pro Lys Pro Lys Thr Gln Pro Lys Lys Ile Asn Gly Lys Thr
     75              80              85

CAG CAG CAA AAG AAG AAA GAC AAG CAA GCC GAC AAG AAG AAG AAG    7729
Gln Gln Gln Lys Lys Lys Asp Lys Gln Ala Asp Lys Lys Lys Lys
     90              95              100

AAA CCC GGA AAA AGA GAA AGA ATG TGC ATG AAG ATT GAA AAT GAC    7774
Lys Pro Gly Lys Arg Glu Arg Met Cys Met Lys Ile Glu Asn Asp
     105             110             115

TGT ATC TTC GAA GTC AAA CAC GAA GGA AAG GTC ACT GGG TAC GCC    7819
Cys Ile Phe Glu Val Lys His Glu Gly Lys Val Thr Gly Tyr Ala
     120             125             130

TGC CTG GTG GGC GAC AAA GTC ATG AAA CCT GCC CAC GTG AAA GGA    7864
Cys Leu Val Gly Asp Lys Val Met Lys Pro Ala His Val Lys Gly
     135             140             145

GTC ATC GAC AAC GCG GAC CTG GCA AAG CTA GCT TTC AAG AAA TCG    7909
Val Ile Asp Asn Ala Asp Leu Ala Lys Leu Ala Phe Lys Lys Ser
     150             155             160

AGC AAG TAT GAC CTT GAG TGT GCC CAG ATA CCA GTT CAC ATG AGG    7954
Ser Lys Tyr Asp Leu Glu Cys Ala Gln Ile Pro Val His Met Arg
     165             170             175

TCG GAT GCC TCA AAG TAC ACG CAT GAG AAG CCC GAG GGA CAC TAT    7999
Ser Asp Ala Ser Lys Tyr Thr His Glu Lys Pro Glu Gly His Tyr
     180             185             190

AAC TGG CAC CAC GGG GCT GTT CAG TAC AGC GGA GGT AGG TTC ACT    8044
Asn Trp His His Gly Ala Val Gln Tyr Ser Gly Gly Arg Phe Thr
     195             200             205

ATA CCG ACA GGA GCG GGC AAA CCG GGA GAC AGT GGC CGG CCC ATC    8089
Ile Pro Thr Gly Ala Gly Lys Pro Gly Asp Ser Gly Arg Pro Ile
     210             215             220

TTT GAC AAC AAG GGG AGG GTA GTC GCT ATC GTC CTG GGC GGG GCC    8134
Phe Asp Asn Lys Gly Arg Val Val Ala Ile Val Leu Gly Gly Ala
     225             230             235
```

Fig. 5M

```
AAC GAG GGC TCA CGC ACA GCA CTG TCG GTG GTC ACC TGG AAC AAA    8179
Asn Glu Gly Ser Arg Thr Ala Leu Ser Val Val Thr Trp Asn Lys
240             245                 250

GAT ATG GTG ACT AGA GTG ACC CCC GAG GGG TCC GAA GAG TGG TCC    8224
Asp Met Val Thr Arg Val Thr Pro Glu Gly Ser Glu Glu Trp Ser
255             260                 265

GCC CCG CTG ATT ACT GCC ATG TGT GTC CTT GCC AAT GCT ACC TTC    8269
Ala Pro Leu Ile Thr Ala Met Cys Val Leu Ala Asn Ala Thr Phe
270             275                 280

CCG TGC TTC CAG CCC CCG TGT GTA CCT TGC TGC TAT GAA AAC AAC    8314
Pro Cys Phe Gln Pro Pro Cys Val Pro Cys Cys Tyr Glu Asn Asn
285             290                 295

GCA GAG GCC ACA CTA CGG ATG CTC GAG GAT AAC GTG GAT AGG CCA    8359
Ala Glu Ala Thr Leu Arg Met Leu Glu Asp Asn Val Asp Arg Pro
300             305                 310

GGG TAC TAC GAC CTC CTT CAG GCA GCC TTG ACG TGC CGA AAC GGA    8404
Gly Tyr Tyr Asp Leu Leu Gln Ala Ala Leu Thr Cys Arg Asn Gly
315             320                 325

ACA AGA CAC CGG CGC AGC GTG TCG CAA CAC TTC AAC GTG TAT AAG    8449
Thr Arg His Arg Arg Ser Val Ser Gln His Phe Asn Val Tyr Lys
330             335                 340

GCT ACA CGC CCT TAC ATC GCG TAC TGC GCC GAC TGC GGA GCA GGG    8494
Ala Thr Arg Pro Tyr Ile Ala Tyr Cys Ala Asp Cys Gly Ala Gly
345             350                 355

CAC TCG TGT CAT AGC CCC GTA GCA ATT GAA GCG GTC AGG TCC GAA    8539
His Ser Cys His Ser Pro Val Ala Ile Glu Ala Val Arg Ser Glu
360             365                 370

GCT ACC GAC GGG ATG CTG AAG ATT CAG TTC TCG GCA CAA ATT GGC    8584
Ala Thr Asp Gly Met Leu Lys Ile Gln Phe Ser Ala Gln Ile Gly
375             380                 385

ATA GAT AAG AGT GAC AAT CAT GAC TAC ACG AAG ATA AGG TAC GCA    8629
Ile Asp Lys Ser Asp Asn His Asp Tyr Thr Lys Ile Arg Tyr Ala
390             395                 400

GAC GGG CAC GCC ATT GAG AAT GCC GTC CGG TCA TCT TTG AAG GTA    8674
Asp Gly His Ala Ile Glu Asn Ala Val Arg Ser Ser Leu Lys Val
405             410                 415

GCC ACC TCC GGA GAC TGT TTC GTC CAT GGC ACA ATG GGA CAT TTC    8719
Ala Thr Ser Gly Asp Cys Phe Val His Gly Thr Met Gly His Phe
420             425                 430

ATA CTG GCA AAG TGC CCA CCG GGT GAA TTC CTG CAG GTC TCG ATC    8764
Ile Leu Ala Lys Cys Pro Pro Gly Glu Phe Leu Gln Val Ser Ile
435             440                 445

CAG GAC ACC AGA AAC GCG GTC CGT GCC TGC AGA ATA CAA TAT CAT    8809
Gln Asp Thr Arg Asn Ala Val Arg Ala Cys Arg Ile Gln Tyr His
450             455                 460
```

Fig. 5N

```
CAT GAC CCT CAA CCG GTG GGT AGA GAA AAA TTT ACA ATT AGA CCA    8854
His Asp Pro Gln Pro Val Gly Arg Glu Lys Phe Thr Ile Arg Pro
465         470                 475

CAC TAT GGA AAA GAG ATC CCT TGC ACC ACT TAT CAA CAG ACC ACA    8899
His Tyr Gly Lys Glu Ile Pro Cys Thr Thr Tyr Gln Gln Thr Thr
480         485                 490

GCG AAG ACC GTG GAG GAA ATC GAC ATG CAT ATG CCG CCA GAT ACG    8944
Ala Lys Thr Val Glu Glu Ile Asp Met His Met Pro Pro Asp Thr
495         500                 505

CCG GAC AGG ACG TTG CTA TCA CAG CAA TCT GGC AAT GTA AAG ATC    8989
Pro Asp Arg Thr Leu Leu Ser Gln Gln Ser Gly Asn Val Lys Ile
510         515                 520

ACA GTC GGA GGA AAG AAG GTG AAA TAC AAC TGC ACC TGT GGA ACC    9034
Thr Val Gly Gly Lys Lys Val Lys Tyr Asn Cys Thr Cys Gly Thr
525         530                 535

GGA AAC GTT GGC ACT ACT AAT TCG GAC ATG ACG ATC AAC ACG TGT    9079
Gly Asn Val Gly Thr Thr Asn Ser Asp Met Thr Ile Asn Thr Cys
540         545                 550

CTA ATA GAG CAG TGC CAC GTC TCA GTG ACG GAC CAT AAG AAA TGG    9124
Leu Ile Glu Gln Cys His Val Ser Val Thr Asp His Lys Lys Trp
555         560                 565

CAG TTC AAC TCA CCT TTC GTC CCG AGA GCC GAC GAA CCG GCT AGA    9169
Gln Phe Asn Ser Pro Phe Val Pro Arg Ala Asp Glu Pro Ala Arg
570         575                 580

AAA GGC AAA GTC CAT ATC CCA TTC CCG TTG GAC AAC ATC ACA TGC    9214
Lys Gly Lys Val His Ile Pro Phe Pro Leu Asp Asn Ile Thr Cys
585         590                 595

AGA GTT CCA ATG GCG CGC GAA CCA ACC GTC ATC CAC GGC AAA AGA    9259
Arg Val Pro Met Ala Arg Glu Pro Thr Val Ile His Gly Lys Arg
600         605                 610

GAA GTG ACA CTG CAC CTT CAC CCA GAT CAT CCC ACG CTC TTT TCC    9304
Glu Val Thr Leu His Leu His Pro Asp His Pro Thr Leu Phe Ser
615         620                 625

TAC CGC ACA CTG GGT GAG GAC CCG CAG TAT CAC GAG GAA TGG GTG    9349
Tyr Arg Thr Leu Gly Glu Asp Pro Gln Tyr His Glu Glu Trp Val
630         635                 640

ACA GCG GCG GTG GAA CGG ACC ATA CCC GTA CCA GTG GAC GGG ATG    9394
Thr Ala Ala Val Glu Arg Thr Ile Pro Val Pro Val Asp Gly Met
645         650                 655

GAG TAC CAC TGG GGA AAC AAC GAC CCA GTG AGG CTT TGG TCT CAA    9439
Glu Tyr His Trp Gly Asn Asn Asp Pro Val Arg Leu Trp Ser Gln
660         665                 670

CTC ACC ACT GAA GGG AAA CCG CAC GGC TGG CCG CAT CAG ATC GTA    9484
Leu Thr Thr Glu Gly Lys Pro His Gly Trp Pro His Gln Ile Val
675         680                 685
```

Fig. 5O

```
CAG TAC TAC TAT GGG CTT TAC CCG GCC GCT ACA GTA TCC GCG GTC    9529
Gln Tyr Tyr Tyr Gly Leu Tyr Pro Ala Ala Thr Val Ser Ala Val
    690             695                 700

GTC GGG ATG AGC TTA CTG GCG TTG ATA TCG ATC TTC GCG TCG TGC    9574
Val Gly Met Ser Leu Leu Ala Leu Ile Ser Ile Phe Ala Ser Cys
    705             710                 715

TAC ATG CTG GTT GCG GCC CGC AGT AAG TGC TTG ACC CCT TAT GCT    9619
Tyr Met Leu Val Ala Ala Arg Ser Lys Cys Leu Thr Pro Tyr Ala
    720             725                 730

TTA ACA CCA GGA GCT GCA GTT CCG TGG ACG CTG GGG ATA CTC TGC    9664
Leu Thr Pro Gly Ala Ala Val Pro Trp Thr Leu Gly Ile Leu Cys
    735             740                 745

TGC GCC CCG CGG GCG CAC GCA GCT AGT GTG GCA GAG ACT ATG GCC    9709
Cys Ala Pro Arg Ala His Ala Ala Ser Val Ala Glu Thr Met Ala
    750             755                 760

TAC TTG TGG GAC CAA AAC CAA GCG TTG TTC TGG TTG GAG TTT GCG    9754
Tyr Leu Trp Asp Gln Asn Gln Ala Leu Phe Trp Leu Glu Phe Ala
    765             770                 775

GCC CCT GTT GCC TGC ATC CTC ATC ATC ACG TAT TGC CTC AGA AAC    9799
Ala Pro Val Ala Cys Ile Leu Ile Ile Thr Tyr Cys Leu Arg Asn
    780             785                 790

GTG CTG TGT TGC TGT AAG AGC CTT TCT TTT TTA GTG CTA CTG AGC    9844
Val Leu Cys Cys Cys Lys Ser Leu Ser Phe Leu Val Leu Leu Ser
    795             800                 805

CTC GGG GCA ACC GCC AGA GCT TAC GAA CAT TCG ACA GTA ATG CCG    9889
Leu Gly Ala Thr Ala Arg Ala Tyr Glu His Ser Thr Val Met Pro
    810             815                 820

AAC GTG GTG GGG TTC CCG TAT AAG GCT CAC ATT GAA AGG CCA GGA    9934
Asn Val Val Gly Phe Pro Tyr Lys Ala His Ile Glu Arg Pro Gly
    825             830                 835

TAT AGC CCC CTC ACT TTG CAG ATG CAG GTT GTT GAA ACC AGC CTC    9979
Tyr Ser Pro Leu Thr Leu Gln Met Gln Val Val Glu Thr Ser Leu
    840             845                 850

GAA CCA ACC CTT AAT TTG GAA TAC ATA ACC TGT GAG TAC AAG ACG    10024
Glu Pro Thr Leu Asn Leu Glu Tyr Ile Thr Cys Glu Tyr Lys Thr
    855             860                 865

GTC GTC CCG TCG CCG TAC GTG AAG TGC TGC GGC GCC TCA GAG TGC    10069
Val Val Pro Ser Pro Tyr Val Lys Cys Cys Gly Ala Ser Glu Cys
    870             875                 880

TCC ACT AAA GAG AAG CCT GAC TAC CAA TGC AAG GTT TAC ACA GGC    10114
Ser Thr Lys Glu Lys Pro Asp Tyr Gln Cys Lys Val Tyr Thr Gly
    885             890                 895

GTG TAC CCG TTC ATG TGG GGA GGG GCA TAT TGC TTC TGC GAC TCA    10159
Val Tyr Pro Phe Met Trp Gly Gly Ala Tyr Cys Phe Cys Asp Ser
    900             905                 910
```

Fig. 5P

```
GAA AAC ACG CAA CTC AGC GAG GCG TAC GTC GAT CGA TCG GAC GTA    10204
Glu Asn Thr Gln Leu Ser Glu Ala Tyr Val Asp Arg Ser Asp Val
915                 920                 925

TGC AGG CAT GAT CAC GCA TCT GCT TAC AAA GCC CAT ACA GCA TCG    10249
Cys Arg His Asp His Ala Ser Ala Tyr Lys Ala His Thr Ala Ser
930                 935                 940

CTG AAG GCC AAA GTG AGG GTT ATG TAC GGC AAC GTA AAC CAG ACT    10294
Leu Lys Ala Lys Val Arg Val Met Tyr Gly Asn Val Asn Gln Thr
945                 950                 955

GTG GAT GTT TAC GTG AAC GGA GAC CAT GCC GTC ACG ATA GGG GGT    10339
Val Asp Val Tyr Val Asn Gly Asp His Ala Val Thr Ile Gly Gly
960                 965                 970

ACT CAG TTC ATA TTC GGG CCG CTG TCA TCG GCC TGG ACC CCG TTC    10384
Thr Gln Phe Ile Phe Gly Pro Leu Ser Ser Ala Trp Thr Pro Phe
975                 980                 985

GAC AAC AAG ATA GTC GTG TAC AAA GAC GAA GTG TTC AAT CAG GAC    10429
Asp Asn Lys Ile Val Val Tyr Lys Asp Glu Val Phe Asn Gln Asp
990                 995                 1000

TTC CCG CCG TAC GGA TCT GGG CAA CCA GGG CGC TTC GGC GAC ATC    10474
Phe Pro Pro Tyr Gly Ser Gly Gln Pro Gly Arg Phe Gly Asp Ile
1005                1010                1015

CAA AGC AGA ACA GTG GAG AGT AAC GAC CTG TAC GCG AAC ACG GCA    10519
Gln Ser Arg Thr Val Glu Ser Asn Asp Leu Tyr Ala Asn Thr Ala
1020                1025                1030

CTG AAG CTG GCA CGC CCT TCA CCC GGC ATG GTC CAT GTA CCG TAC    10564
Leu Lys Leu Ala Arg Pro Ser Pro Gly Met Val His Val Pro Tyr
1035                1040                1045

ACA CAG ACA CCT TCA GGG TTC AAA TAT TGG CTA AAG GAA AAA GGG    10609
Thr Gln Thr Pro Ser Gly Phe Lys Tyr Trp Leu Lys Glu Lys Gly
1050                1055                1060

ACA GCC CTA AAT ACG AAG GCT CCT TTT GGC TGC CAA ATC AAA ACG    10654
Thr Ala Leu Asn Thr Lys Ala Pro Phe Gly Cys Gln Ile Lys Thr
1065                1070                1075

AAC CCT GTC AGG GCC ATG AAC TGC GCC GTG GGA AAC ATC CCT GTC    10699
Asn Pro Val Arg Ala Met Asn Cys Ala Val Gly Asn Ile Pro Val
1080                1085                1090

TCC ATG AAT TTG CCT GAC AGC GCC TTT ACC CGC ATT GTC GAG GCG    10744
Ser Met Asn Leu Pro Asp Ser Ala Phe Thr Arg Ile Val Glu Ala
1095                1100                1105

CCG ACC ATC ATT GAC CTG ACT TGC ACA GTG GCT ACC TGT ACG CAC    10789
Pro Thr Ile Ile Asp Leu Thr Cys Thr Val Ala Thr Cys Thr His
1110                1115                1120

TCC TCG GAT TTC GGC GGC GTC TTG ACA CTG ACG TAC AAG ACC AAC
Ser Ser Asp Phe Gly Gly Val Leu Thr Leu Thr Tyr Lys Thr Asn
1125                1130                1135
```

Fig. 5Q

```
AAG AAC GGG GAC TGC TCT GTA CAC TCG CAC TCT AAC GTA GCT ACT    10879
Lys Asn Gly Asp Cys Ser Val His Ser His Ser Asn Val Ala Thr
    1140            1145            1150

CTA CAG GAG GCC ACA GCA AAA GTG AAG ACA GCA GGT AAG GTG ACC    10924
Leu Gln Glu Ala Thr Ala Lys Val Lys Thr Ala Gly Lys Val Thr
    1155            1160            1165

TTA CAC TTC TCC ACG GCA AGC GCA TCA CCT TCT TTT GTG GTG TCG    10969
Leu His Phe Ser Thr Ala Ser Ala Ser Pro Ser Phe Val Val Ser
    1170            1175            1180

CTA TGC AGT GCT AGG GCC ACC TGT TCA GCG TCG TGT GAG CCC CCG    11014
Leu Cys Ser Ala Arg Ala Thr Cys Ser Ala Ser Cys Glu Pro Pro
    1185            1190            1195

AAA GAC CAC ATA GTC CCA TAT GCG GCT AGC CAC AGT AAC GTA GTG    11059
Lys Asp His Ile Val Pro Tyr Ala Ala Ser His Ser Asn Val Val
    1200            1205            1210

TTT CCA GAC ATG TCG GGC ACC GCA CTA TCA TGG GTG CAG AAA ATC    11104
Phe Pro Asp Met Ser Gly Thr Ala Leu Ser Trp Val Gln Lys Ile
    1215            1220            1225

TCG GGT GGT CTG GGG GCC TTC GCA ATC GGC GCT ATC CTG GTG CTG    11149
Ser Gly Gly Leu Gly Ala Phe Ala Ile Gly Ala Ile Leu Val Leu
    1230            1235            1240

GTT GTG GTC ACT TGC ATT GGG CTC CGC AGA TAA GTTAGGGTAG         11192
Val Val Val Thr Cys Ile Gly Leu Arg Arg
    1245            1250
```

GCAATGGCAT TGATATAGCA AGAAAATTGA AAACAGAAAA AGTTAGGGTA AGCAATGGCA
11252

TATAACCATA ACTGTATAAC TTGTAACAAA GCGCAACAAG ACCTGCGCAA TTGGCCCCGT
11312

GGTCCGCCTC ACGGAAACTC GGGGCAACTC ATATTGACAC ATTAATTGGC AATAATTGGA
11372

AGCTTACATA AGCTTAATTC GACGAATAAT TGGATTTTTA TTTTATTTTG CAATTGGTTT
11432

TTAATATTTC CAAAAAAAAA AAAAAAAAAA AAAAAAAAAA AAAAAAAAAA AAAAAAAAAA
11492

AAAAAAAAAA AAAAAAAAAA ACTAG
11517

```
                                BamH1
--- --- --- --- --- --- --- --- -G GAT CC- --- --- --- --- --- --- ---    SFV vector E2
AAC TCA CCT TTC GTC CCG AGA GCC GAC CCG AGA GCT AGA AAA GGC AAA GTC CAT    SFV E2
Asn Ser Pro Phe Val Pro Arg Ala Asp Pro Arg Ala Arg Lys Gly Lys Val His    SFV E2
                                Glu Asp                                    SFV vector E2
                                246 247
```

```
GAT CCG CGT ATC CAG AGA GGA CCA GGA AGA GCA TTT GTT GAG                    HIV-gp120
GC GCA TAG GTC TCT CCT GGT CCT TCT CGT AAA CAA CTC CTA G                   HIV epitope
Asp Pro Arg Ile Gln Arg Gly Pro Gly Arg Ala Phe Val Glu Asp
```

Cut with BamH1
Insert HIV oligo

→

```
GAG GAT CCG CGT ATC CAG AGA GGA CCA GGA AGA GCA TTT GTT GAG GAT CCG        SFV-HIV chimera
CTC CTA GGC GCA TAG GTC TCT CCT GGT CCT TCT CGT AAA CAA CTC CTA GGC
Glu Asp Pro Arg Ile Gln Arg Gly Pro Gly Arg Ala Phe Val Glu Asp Pro
                                313
```

Figure 12A

DNA EXPRESSION SYSTEMS BASED ON ALPHAVIRUSES

The present invention is related to DNA expression systems based on alphaviruses, which systems can be used to transform animal cells for use in the production of desired products, such as proteins and vaccines, in high yields.

The rapid development of biotechnology is to a large extent due to the introduction of recombinant DNA technique, which has revolutionized cellbiological and medical research by opening new approaches to elucidate the molecular mechanisms of the cell. With the aid of the techniques of cDNA cloning, large numbers of interesting protein molecules are characterized each year. Therefore, a lot of research activity is today directed to elucidate the relationship between structure and function of these molecules. Eventually this knowledge will increase our possibilities to preserve healthiness and combat diseases in both humans and animals. Indeed, there is today a growing list of new "cloned" protein products that are already used as pharmaceuticals or diagnostics.

In the recombinant DNA approaches to study biological questions, DNA expression systems are crucial elements. Thus, efficient DNA expression systems, which are simple and safe to use, give high yields of the desired product and can be used in a variety of host cells, especially also in mammalian cells, are in great demand.

Many attempts have been made to develop DNA expression systems, which fulfill these requirements. Often, viruses have been used as a source of such systems. However, up to date none of the existing vital expression systems fulfill all these requirements in a satisfying way. For instance, the Baculovirus expression system for cDNA is extremely efficient but can be used only in insect cells (see Reference 1 of the list of cited references; for the sake of convenience, in the following the cited references are only identified by the number they have on said list). As many important molecules will have to be produced and processed in cells of mammalian origin in order for them to become active, this system cannot be used in such cases. Furthermore, the Baculovirus cDNA expression system is not practically convenient for analysis of the relationship between structure and function of a protein because this involves in general the analysis of whole series of mutant variants. Today it takes about 6–8 weeks to construct a single Baculo recombinant virus for phenotype analyses. This latter problem is also true for the rather efficient Vaccinia recombinant virus and other contemporary recombinant virus cDNA expression systems (2,3). The procedure to establish stably transformed cell lines is also a very laborious procedure, and in addition, often combined with very low levels of protein expression.

Hitherto, most attempts to develop viral DNA expression systems have been based on viruses having DNA genomes or retroviruses, the replicative intermediate of the latter being double stranded DNA.

Recently, however, also viruses comprising RNA genomes have been used to develop DNA expression systems.

In EP 0 194 809 RNA transformation vectors derived from (+) strand RNA viruses are disclosed which comprise capped viral RNA that has been modified by insertion of exogenous RNA into a region non-essential for replication of said virus RNA genome. These vectors are used for expression of the function of said exogenous RNA in cells transformed therewith. The RNA can be used in solution or packaged into capsids. Furthermore, this RNA can be used to generate new cells having new functions, i.e. protein expression. The invention of said reference is generally claimed as regards host cells, (+) strand RNA viruses and the like. Nevertheless, it is obvious from the experimental support provided therein that only plant cells have been transformed and in addition only Bromo Mosaic virus, a plant virus, has been used as transformation vector.

Although it is stated in said reference that it is readily apparent to those skilled in the art to convert any RNA virus-cell system to a useful expression system for exogenous DNA using principals described in the reference, this has not been proven to be true in at least the case of animal cell RNA viruses. The reasons for this seem to be several. These include:

1) Inefficiencies in transfecting animal cells with in vitro transcribed RNA;
2) Inefficiency of apparently replication competent RNA transcripts to start RNA replication after commonly used transfection procedures;
3) The inability to produce high titre stocks of recombinant virus that does not contain any helper virus;
4) The inability to establish stable traits of transformed cells expressing the function of the exogenous RNA.

In Proc. Natl. Acad. Sci. USA, Vol 84, 1987, pp 4811–4815 a gene expression system based on a member of the Alphavirus genus, viz. Sindbis virus, is disclosed which is used to express the bacterial CAT (chloramphenicol acetyltransferase) gene in avian cells, such as chicken embryo fibroblasts.

Xiong et al., Science, Vol 243, 1989, 1188–1191 also disclose a gene expression system based on Sindbis virus. This system is said to be efficient in a broad range of animal cells. Expression of the bacterial CAT gene in insect, avian and mammalian cells inclusive of human cells is disclosed therein.

Even though it is known from prior art that one member of the Alphavirus genus, the Sindbis virus, can tolerate insertion and direct the expression of at least one foreign gene, the bacterial chloramfenicol acetyl transferase (CAT) gene, it is evident from the results described that both systems described above are both ineffective in terms of exogenous gene expression and also very cumbersome to use. Hence, neither system has found any usage in the field of DNA expression in animal cells today.

In the first example a cDNA copy of a defective interfering (DI) virus variant of Sindbis virus was used to carry the CAT gene. RNA was transcribed in vitro and used to transfect avian cells and some CAT protein production could be demonstrated after infecting cells with wild-type Sindbis virus. The latter virus provided the viral replicase for expression of the CAT construct. The inefficiency of this system depends on 1) low level of initial DI-CAT RNA transfection (0.05–0.5% of cells) and 2) inefficient usage of the DI-CAT RNA for protein translation because of unnatural and suboptimal protein initiation translation signals. This same system also results in packaging of some of the recombinant DI-CAT genomes into virus particles. However, this occurs simultaneously with a very large excess of wild-type Sindbis virus production. Therefore, the usage of this mixed virus stock for CAT expression will be much hampered by the fact that most of the replication and translation activity of the cells infected with such a stock will deal with the wild-type and not with recombinant gene expression.

Much of the same problems are inherent to the other Sindbis expression system described. In this an RNA replication competent Sindbis DNA vector is used to carry the CAT gene. RNA produced in vitro is shown to replicate in animal cells and CAT activity is found. However, as only a very low number of cells are transfected the overall CAT production remains low. Another possible explanation for this is that the Sindbis construct used is not optimal for replication. Wild-type Sindbis virus can be used to rescue the recombinant genome into particles together with an excess of wild-type genomes and this mixed stock can then be used to express a CAT protein via infection. However, this stock has the same problems as described above for the recombinant DI system. The latter paper shows also that if virus is amplified by several passages increased titres of the recombinant virus particles can be obtained. However, one should remember that the titre of the wild-type virus will increase correspondingly and the original problem of mostly wild-type virus production remains. There are also several potential problems when using several passages to produce a mixed virus stock. As there is no selected pressure for preservation of the recombinant genomes these might easily 1) undergo rearrangements and 2) become outnumbered by wild-type genomes as a consequence of less efficient replication and/or packaging properties.

Another important aspect of viral DNA expression vectors is use thereof to express antigens of unrelated pathogens and thus they can be used as vaccines against such pathogens.

Development of safe and effective vaccines against viral diseases has proven to be quite a difficult task. Although many existing vaccines have helped to combat the worldwide spread of many infectious diseases, there is still a large number of infectious agents against which effective vaccines are missing. The current procedures of preparing vaccines present several problems: (1) it is often difficult to prepare sufficiently large amounts of antigenic material; (2) In many cases there is the additional hazard that the vaccine preparation is not killed or sufficiently attenuated; (3) Effective vaccines are often hard to produce since there is a major difficulty in presenting the antigenic epitope in an immunologically active form; (4) In the case of many viruses, genetic variations in the antigenic components results in the evolution of new strains with new serological specificities, which again creates a need for the development of new vaccines.

Two types of viral DNA vectors have been developed in order to overcome many of these problems in vaccine production. These either provide recombinant viruses or provide chimaeric viruses. The recombinant viruses contain a wild-type virus package around a recombinant genome. These particles can be used to infect cells which then produce the antigenic protein from the recombinant genome. The chimaeric viruses also contain a recombinant genome but this specifies the production of an antigen, usually as part of a normal virus structural protein, which then will be packaged in progeny particles and e.g. exposed on the surface of the viral spike proteins. The major advantages of these kind of virus preparations for the purpose of being used as a vaccine are 1) that they can be produced in large scale and 2) that they provide antigen in a natural form to the immunological system of the organism. Cells, which have been infected with recombinant viruses, will synthesize the exogenous antigen product, process it into peptides that then present them to T cells in the normal way. In the case of the chimaeric virus there is, in addition, an exposition of the antigen in the context of the subunits of the virus particle itself. Therefore, the chimaeric virus is also-called an epitope carrier.

The major difficulty with these kind of vaccine preparations are, how to ensure a safe and limited replication of the particles in the host without side effects. So far, some success has been obtained with vaccinia virus as an example of the recombinant virus approach (69) and of polio virus as an example of a chimaeric particle (70–72). As both virus variants are based on commonly used vaccine strains one might argue that they could be useful vaccine candidates also as recombinant respectively chimaeric particles (69–72). However, both virus vaccines are combined with the risk for side effects, even severe ones, and in addition these virus strains have already been used as vaccines in large parts of the population in many countries.

As is clear from the afore mentioned discussion there is much need to develop improved DNA expression systems both for an easy production of important proteins or polypeptides in high yields in various kinds of animal cells and for the production of recombinant viruses or chimaeric viruses to be used as safe and efficient vaccines against various pathogens.

Thus, an object of the present invention is to provide an improved DNA expression system based on virus vectors which can be used both to produce proteins and polypeptides and as recombinant virus or chimaeric virus, which system offers many advantages over prior art.

To that end, according to the present invention there is provided an RNA molecule derived from an alphavirus RNA genome and capable of efficient infection of animal host cells, which RNA molecule comprises the complete alphavirus RNA genome regions, which are essential to replication of the said alphavirus RNA, and further comprises an exogenous RNA sequence capable of expressing its function in said host cell, said exogenous RNA sequence being inserted into a region of the RNA molecule which is non-essential to replication thereof.

Alphavirus is a genus belonging to the family Togaviridae having single stranded RNA genomes of positive polarity enclosed in a nucleocapsid surrounded by an envelope containing viral spike proteins.

The Alphavirus genus comprises among others the Sindbis virus, the Semliki Forest virus (SFV) and the Ross River virus, which are all closely related. According to a preferred embodiment of the invention, the Semliki Forest virus (SFV) is used as the basis of the DNA expression system.

The exogenous RNA sequence encodes a desired genetic trait, which is to be conferred on the virus or the host cell, and said sequence is usually complementary to a DNA or cDNA sequence encoding said genetic trait. Said DNA sequence may be comprised of an isolated natural gene, such as a bacterial or mammalian gene, or may constitute a synthetic DNA sequence coding for the desired genetic trait i.e. expression of a desired product, such as an enzyme, hormone, etc. or expression of a peptide sequence defining an exogenous antigenic epitope or determinant.

If the exogenous RNA sequence codes for a product, such as a protein or polypeptide, it is inserted into the viral RNA genome replacing deleted structural protein encoding region (s) thereof, whereas a viral epitope encoding RNA sequence may be inserted into structural protein encoding regions of the viral RNA genome, which essentially do not comprise deletions or only have a few nucleosides deleted.

The RNA molecule can be used per se, e.g. in solution to transform animal cells by conventional transfection, e.g. the DEAE-Dextran method or the calcium phosphate precipitation method. However, the rate of transformation of cells, and, thus the expression rate can be expected to increase substantially if the cells are transformed by infection with infectious viral particles. Thus, a suitable embodiment of the invention is related to an RNA virus expression vector comprising the RNA molecule of this invention packaged into infectious particles comprising the said RNA within the alphavirus nucleocapsid and surrounded by the membrane including the alphavirus spike proteins.

The RNA molecule of the present invention can be packaged into such particles without restraints provided that it has a total size corresponding to the wild type alphavirus RNA genome or deviating therefrom to an extent compatible with package of the said RNA into the said infectious particles.

These infectious particles, which include recombinant genomes packaged to produce a pure, high titre recombinant virus stock, provides a means for exogenous genes or DNA sequences to be expressed by normal virus particle infection, which as regards transformation degree, is much more efficient than RNA transfection.

According to a suitable embodiment of the invention such infectious particles are produced by cotransfection of animal host cells with the present RNA which lacks part of or the complete region(s) encoding the structural viral proteins together with a helper RNA molecule transcribed in vitro from a helper DNA vector comprising the SP6 promoter region, those 5' and 3' regions of the alphavirus cDNA which encode cis acting signals needed for RNA replication and the region encoding the viral structural proteins but lacking essentially all of the nonstructural virus proteins encoding regions including sequences encoding RNA signals for packaging of RNA into nucleocapsid particles, and culturing the host cells.

According to another aspect of the invention efficient introduction of the present RNA into animal host cells can be achieved by electroporation. For example, in the case of Baby Hamster Kidney (BHK) cells a transformation degree of almost 100% has been obtained for the introduction of an RNA transcript derived from SFV cDNA of the present invention. This makes it possible to reach so high levels of exogenous protein production in every cell that the proteins can be followed in total cell lysates without the need of prior concentration by antibody precipitation.

By electroporation, it is also possible to obtain a high degree of cotransfection in the above process for production of infectious particles comprising packaged RNA of the present invention. Essentially all animal cells will contain both the present RNA molecule and the helper RNA molecule, which leads to a very efficient trans complementation and formation of infectious particles. A pure recombinant virus stock, consisting of up to $10^9-10^{10}$ infectious particles, can be obtained from $5\times10^6$ cotransfected cells after only a 24 h incubation. Furthermore, the so obtained virus stock is very safe to use, since it is comprised of viruses containing only the desired recombinant genome, which can infect host cells but can not produce new progeny virus.

Theoretically, a regeneration of a wild-type virus genome could take place when producing the recombinant virus in the contransfected cells. However, the possibility to avoid spread of such virus can be eliminated by incorporating a conditionally lethal mutation into the structural part of the helper genome. Such a mutation is described in the experimental part of this application. Thus, the virus produced with such a helper will be noninfectious if not treated in vitro under special conditions.

The technique of electroporation is well known within the field of biotechnology and optimal conditions can be established by the man skilled in the art. For instance, a BioRad Gene pulser apparatus (BioRad, Richmond, Calif., USA) can be used to perform said process.

The RNA molecule of the present invention is derived by in vivo or in vitro transcription of a cDNA clone, originally produced from an alphavirus RNA and comprising an inserted exogenous DNA fragment encoding a desired genetic trait.

Accordingly, the present invention is also related to a DNA expression vector comprising a full-length or partial cDNA complementary to alphavirus RNA or parts thereof and located immediately downstream of the SP6 RNA polymerase promoter and having a 5'ATGG, a 5'GATGG or any other 5' terminus and a TTTCCA$_{69}$ACTAGT (SEQ ID NO.:25) or any other 3' terminus.

According to one aspect of the present invention portions of the viral cDNA are deleted, the deletions comprising the complete or part of the region(s) encoding the virus structural proteins, and the vector further comprises an integrated polylinker region, which may correspond to BamHI-SmaI-XmaI, inserted at a location which enables an exogenous DNA fragment encoding a foreign polypeptide or protein to be inserted into the vector cDNA for subsequent expression in an animal host cell.

According to another aspect of this invention, the vector is comprised of full-length cDNA wherein an exogenous DNA fragment encoding a foreign epitopic peptide sequence can be inserted into a region coding for the viral structural proteins.

It is appreciated that this cDNA clone with its exogenous DNA insert is very efficiently replicated after having been introduced into animal cells by transfection.

A very important aspect of the present invention is that it is applicable to a broad range of host cells of animal origin. These host cells can be selected from avian, mammalian, reptilian, amphibian, insect and fish cells. Illustrative of mammalian cells are human, monkey, hamster, mouse and porcine cells. Suitable avian cells are chicken cells, and as reptilian cells viper cells can be used. Cells from frogs and from mosquitoes and flies (Drosophila) are illustrative of amphibian and insect cells, respectively. A very efficient virus vector/host cell system according to the invention is based on SFV/BHK cells, which will be discussed more in detail further below.

However, even though a very important advantage of the present DNA expression vector is that it is very efficient in a broad variety of animal cells it can also be used in other eucaryotic cells and in procaryotic cells.

The present invention is also related to a method to produce transformed animal host cells comprising transfection of the cells with the present RNA molecule or with the present transcription vector comprised of cDNA and carrying an exogenous DNA fragment. According to a suitable embodiment of the invention, transfection is produced by the above mentioned electroporation method, a very high transfection rate being obtained.

A further suitable transformation process is based on infection of the animal host cells with the above mentioned infectious viral particles comprising the present RNA molecule.

The transformed cells of the present invention can be used for different purposes.

One important aspect of the invention is related to use of the present transformed cells to produce a polypeptide or a protein by culturing the transformed cells to express the exogenous RNA and subsequent isolation and purification of the product formed by said expression. The transformed cells can be produced by infection with the present viral particles comprising exogenous RNA encoding the polypeptide or protein as mentioned above, or by transfection with an RNA transcript obtained by in vitro transcription of the present DNA vector comprised of cDNA and carrying an exogenous DNA fragment coding for the polypeptide or the protein.

Another important aspect of the invention is related to use of the present transformed cells for the production of antigens comprised of chimaeric virus particles for use as immunizing component in vaccines or for immunization purposes for in vivo production of immunizing components for antisera production.

Accordingly, the present invention is also related to an antigen consisting of a chimaeric alphavirus having an exogenous epitopic peptide sequence inserted into its structural proteins.

Preferably, the chimaeric alphavirus is derived from SFV.

According to a suitable embodiment, the exogenous epitopic peptide sequence is comprised of an epitopic peptide sequence derived from a structural protein of a virus belonging to the immunodeficiency virus class inclusive of the human immunodeficiency virus types.

A further aspect of the invention is related to a vaccine preparation comprising the said antigen as immunizing component.

In said vaccine the chimaeric alphavirus is suitably attenuated by comprising mutations, such as the conditionally lethal SFV-mutation described before, amber (stop codon) or temperature sensitive mutations, in its genome.

For instance, if the chimaeric virus particles containing the aforementioned conditional lethal mutation in its structural proteins (a defect to undergo a certain proteolytical cleavage in host cell during morphogenesis) is used as a vaccine then such chimaeric virus particles are first activated by limited proteolytic treatment before being given to the organism so that may can infect recipient cells. New chimaeric particles will be formed in cells infected with the activated virus but these will again have the conditional lethal phenotype and further spread of infection is not possible.

The invention is also concerned with a method for the production of the present antigen comprising a) in vitro transcription of the cDNA of the present DNA vector carrying an exogenous DNA fragment encoding the foreign epitopic peptide sequence and transfection of animal host cells with the produced RNA transcript, or b) transfection of animal host cells with the said cDNA of the above step a), culturing the transfected cells and recovering the chimaeric alphavirus antigen. Preferably, transfection is produced by electroporation.

Still another aspect of the invention is to use a recombinant virus containing exogenous RNA encoding a polypeptide antigen for vaccination purpose or to produce antisera. In this case the recombinant virus or the conditionally lethal variant of it is used to infect cells in vivo and antigen production will take place in the infected cells and used for antigen presentation to the immunological system.

According to another embodiment of the invention, the present antigen is produced in an organism by using in vivo infection with the present infectious particles containing exogenous RNA encoding an exogenous epitopic peptide sequence.

BRIEF DESCRIPTION OF THE DRAWINGS

In the following, the present invention will be illustrated more in detail with reference to the Semliki Forest virus (SFV), which is representative for the alphaviruses. This description can be more fully understood in conjunction with the accompanying drawings in which:

FIG. 4B shows plasmid pPLH211, i.e. the SP6 expression vector used as carrier for the full-length infectious clone of SFV. FIG. 4D shows the structure of the SP6 promoter area of the SFV clone (SEQ ID NO:25); the solid bar indicates the SP6 promoter sequence, and the first nucleotide to be transcribed is marked by an asterisk; underlined regions denote authentic SFV sequences.

FIGS. 5A–5Q shows the complete nucleotide sequence of the pSP6-SFV4 RNA transcript as DNA (U=T) (SEQ ID NO:1) and underneath the DNA sequence, the amino acid sequence of the non-structural polyprotein and the structural polyprotein (SEQ ID NO:2).

FIGS. 12A–12B show in its upper part sequences encompassing the major antigenic site of SFV and the in vitro made substitutions leading to a BamHI restriction endonuclease site (SEQ ID NO:7,8), sequences spanning the principal neutralizing domain of the HIV gp120 protein (SEQ ID NO:9,10), and the HIV domain inserted into the SFV carrier protein E2 as a BamHI oligonucleotide (SEQ ID NO:11,12); and its lower part is a schematic presentation of the SFV spike structure with blow-ups of domain 246–251 in either wild type or chimaeric form.

The alphavirus Semliki Forest virus (abbreviated SFV in the following text) has for some 20 years been used as model system in both virology and cell biology to study membrane biosynthesis, membrane structure and membrane function as well as protein-RNA interactions (4, 5). The major reason for the use of SFV as such a model is due to its simple structure and efficient replication.

Figure 1:
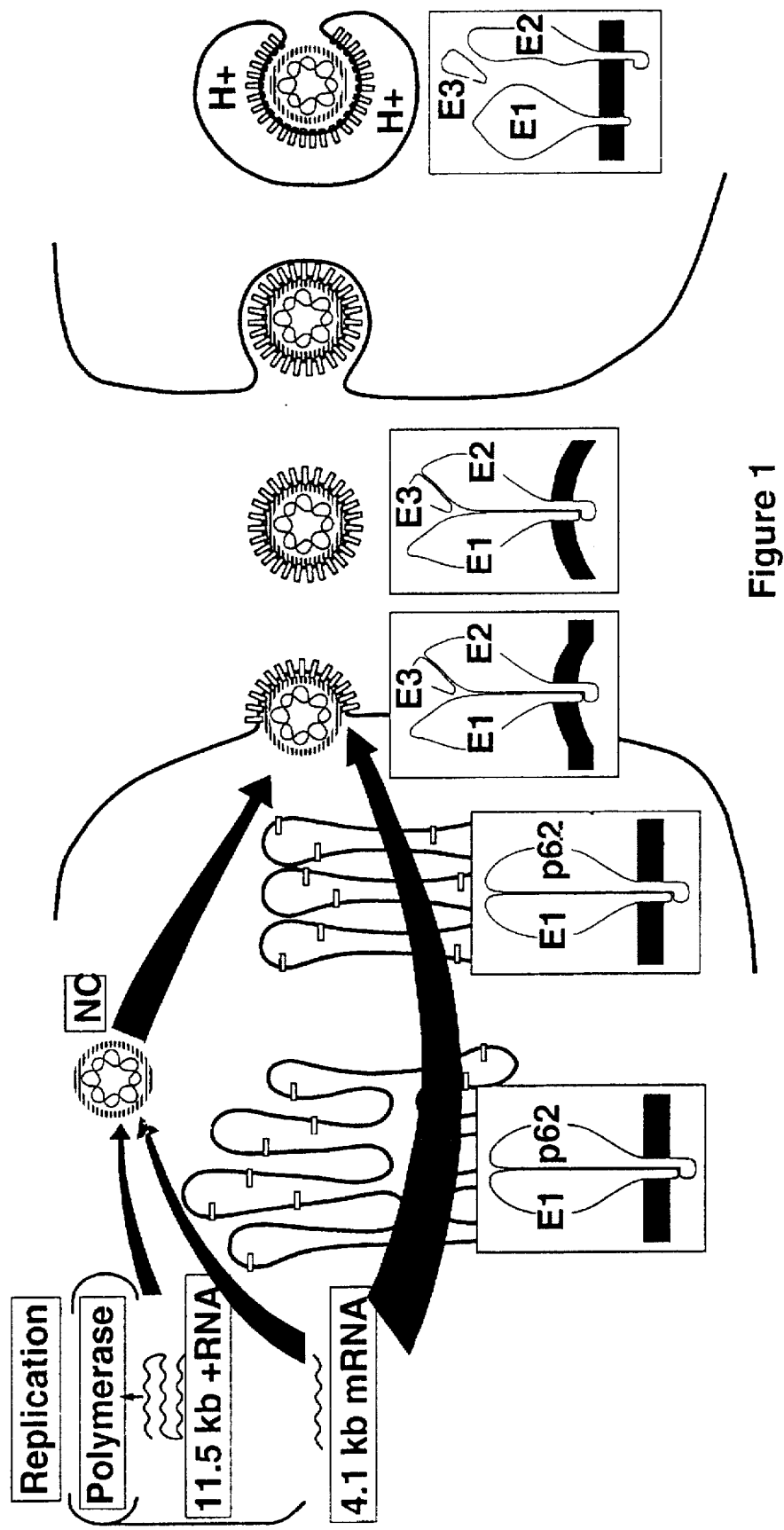
FIG. 1 is a schematic view over the main assembly and disassembly events involved in the life cycle of the Semliki Forest virus, and also shows regulation of the activation of SFV entry functions by p62 cleavage and pH1.
Figure 2:
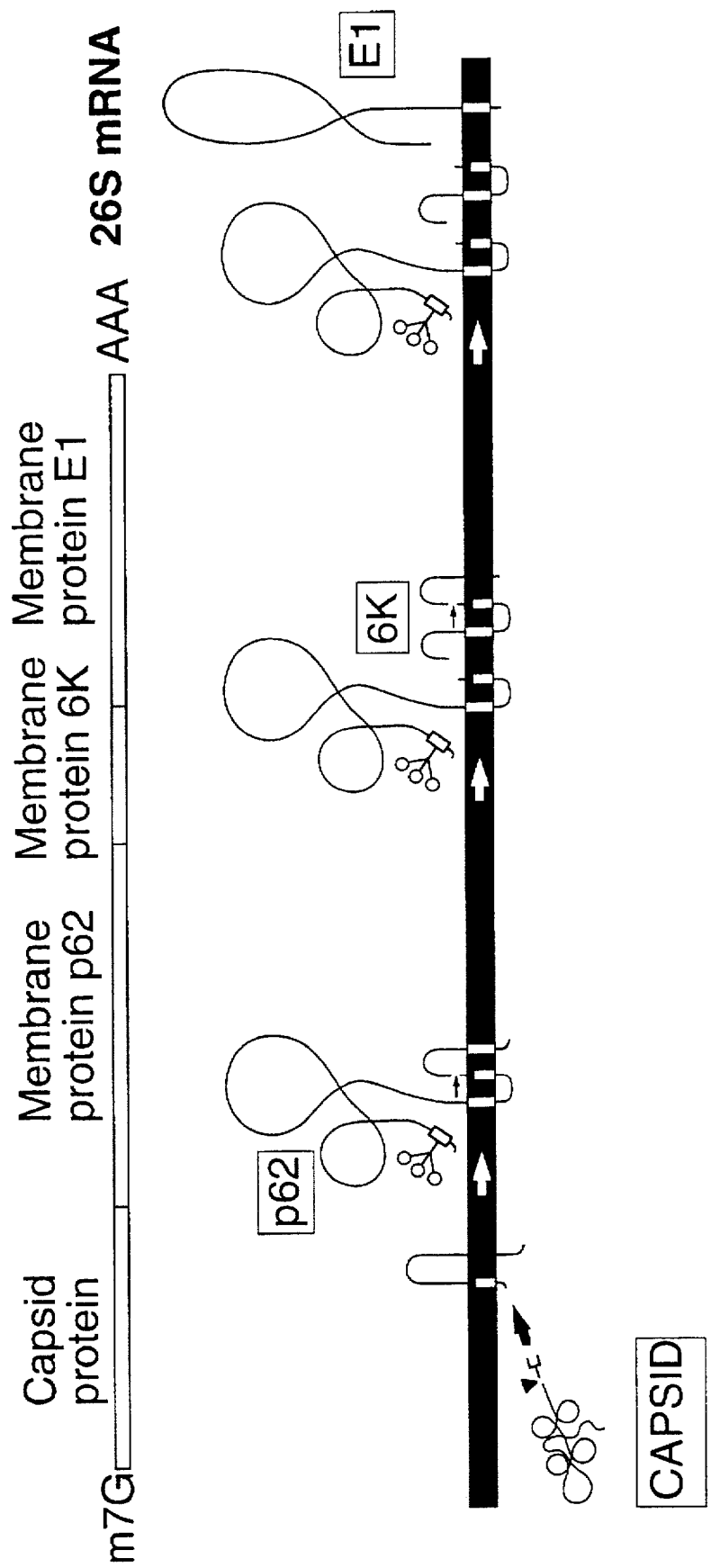
FIG. 2 illustrates the use of translocation signals during synthesis of the structural proteins of SFV; top, the gene map of the 26S subgenomic RNA; middle, the process of membrane translocation of the p62, 6K and E1 proteins; small arrows on the lumenal side denote signal peptidase cleavages; at the bottom, the characteristics of the three signal peptides are listed.
Figure 3:
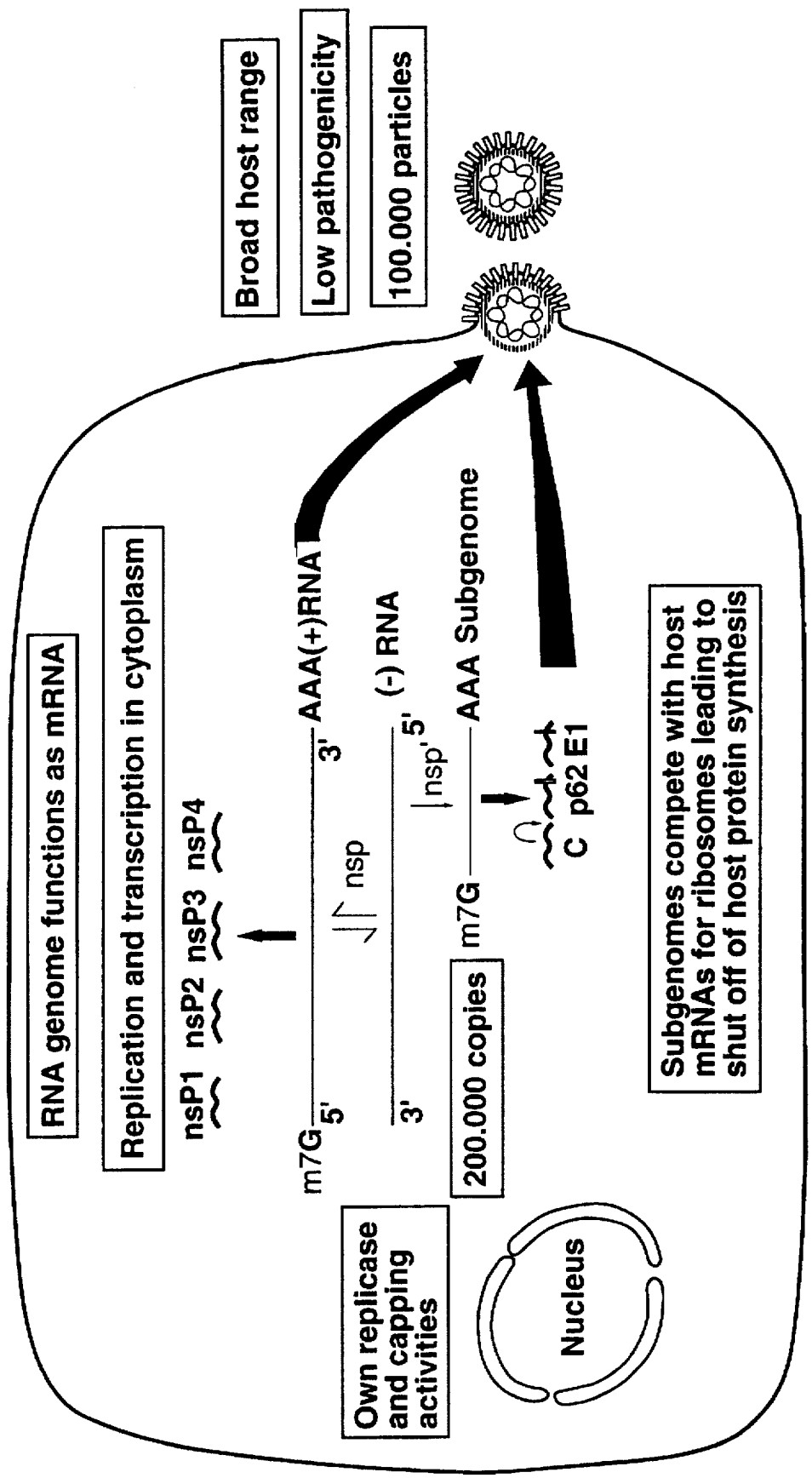
FIG. 3 shows features that make SFV an excellent choice as an expression vector.

With reference to FIG. 1–3, in the following the SFV and its replication are explained more in detail. In essential parts, this disclosure is true also for the other alphaviruses, such as the Sindbis virus, and many of the references cited in this connection are indeed directed to the Sindbis virus. SFV consists of an RNA-containing nucleocapsid and a surrounding membrane composed of a lipid bilayer and proteins, a regularly arranged icosahedral shell of a protein called C protein forming the capsid inside which the genomic RNA is packaged. The capsid is surrounded by-the lipid bilayer that contains three proteins called E1, E2, and E3. These so-called envelope proteins are glycoproteins and their glycosylated portions are on the outside of the lipid bilayer, complexes of these proteins forming the "spikes" that can be seen in electron micrographs to project outward from the surface of the virus.

The SFV genome is a single-stranded 5'-capped and 3'-polyadenylated RNA molecule of 11422 nucleotides (6,7). It has positive polarity, i.e. it functions as an mRNA, and naked RNA is able to start an infection when introduced into the cytoplasm of a cell. Infection is initiated when the virus binds to protein receptors on the host cell plasma membrane, whereby the virions become selectively incorporated into "coated pits" on the surface of the plasma membrane, which invaginate to form coated vesicles inside the cell, whereafter said vesicles bearing endocytosed virions rapidly fuse with organelles called endosomes. From the endosome, the virus escapes into the cell cytosol as the bare nucleocapsid, the viral envelope remaining in the endosome. Thereafter, the nucleocapsid is "uncoated" and, thus, the genomic RNA is released. Referring now to FIG. 1, infection then proceeds with the translation of the 5' two-thirds of the genome into a polyprotein which by self-cleavage is processed to the four nonstructural proteins nsP1–4 (8). Protein nsP1 encodes a methyl transferase which is responsible for virus-specific capping activity as well as initiation of minus strand synthesis (9, 10); nsP2 is the protease that cleaves the polyprotein into its four subcomponents (11, 12); nsP3 is a phosphoprotein (13, 14) of as yet unknown function, and nsP4 contains the SFV RNA polymerase activity (15, 16). Once the nsP proteins have been synthesized they are responsible for the replication of the plus strand (42S) genome into full-length minus strands. These molecules then serve as templates for the production of new 42S genomic RNAs. They also serve as templates for the synthesis of subgenomic (26S) RNA. This 4073 nucleotides long RNA is colinear with the last one-third of the genome, and its synthesis is internally initiated at the 26S promoter on the 42S minus strands (17, 18).

The capsid and envelope proteins are synthesized in different compartments, and they follow separate pathways through the cytoplasm, viz. the envelope proteins are synthesized by membrane-bound ribosomes attached to the rough endoplasmic reticulum, and the capsid protein is synthesized by free ribosomes in the cytosol. However, the 26S RNA codes for all the structural proteins of the virus, and these are synthesized as a polyprotein precursor in the order C-E3-E2-6K-E1 (19). Once the capsid (C) protein has been synthesized it folds to act as a protease cleaving itself off the nascent chain (20, 21). The synthesized C proteins bind to the recently replicated genomic RNA to form new nucleocapsid structures in the cell cytoplasm.

The said cleavage reveals an N-terminal signal sequence in the nascent chain which is recognized by the signal recognition particle targeting the nascent chain—ribosome complex to the endoplasmic reticulum (ER) membrane (22, 23), where it is cotranslationally translocated and cleaved by signal peptidase to the three structural membrane proteins p62 (precursor form of E3/E2), 6K and E1 (24, 25). The translocational signals used during the synthesis of the structural proteins are illustrated in FIG. 2. The membrane proteins undergo extensive posttranslational modifications within the biosynthetic transport pathway of the cell. The p62 protein forms a heterodimer with E1 via its E3 domain in the endoplasmic reticulum (26). This dimer is transported out to the plasma membrane, where virus budding occurs through spike nucleocapsid interactions. At a very late (post-Golgi) stage of transport the p62 protein is cleaved to E3 and E2 (27), the forms that are found in mature virions. This cleavage activates the host cell binding function of the virion as well as the membrane fusion potential of E1. The latter activity is expressed by a second, low-pH activation step after the virus enters the endosomes of a new host cell and is responsible for the release of the viral nucleocapsid into the cell cytoplasm (28–32). The mature virus particles contain one single copy of the RNA genome encapsidated within 180 copies of the capsid protein in a T=3 symmetry, and is surrounded by a lipid bilayer carrying 240 copies of the spike trimer protein consisting of E1+E2+E3 arranged in groups of three in a T=4 symmetry (33).

The SFV entry functions are activated and regulated by p62 cleavage and pH. More specifically, the p62-E1 heterodimers formed in the ER are acid resistant. When these heterodimers are transported to the plasma membrane via the Golgi complex the E1 fusogen cannot be activated in spite of the mildly acidic environment, since activation requires dissociation of the complex. As is illustrated in FIG. 1, the released virus particles contain E2E1 complexes. Since the association between E2 and E1 is sensitive to acidic pH, during entry of the virus into a host cell through endocytosis the acidic milieu of the endosome triggers the dissociation of the spike complex (E1 E2 E3) resulting in free E1. The latter can be activated for the catalysis of the fusion process between the viral and endosomal membranes in the infection process as disclosed above.

As indicated in the preceding parts of the disclosure, the alphavirus system, and especially the SFV system, has several unique features which are to advantage in DNA expression systems. These are summarized below with reference to FIG. 3.

1. Genome of positive polarity. The SFV RNA genome is of positive polarity, i.e. it functions directly as mRNA, and infectious RNA molecules can thus be obtained by transcription from a full-length cDNA copy of the genome.

2. Efficient replication. The infecting RNA molecule codes for its own RNA replicase, which in turn drives an efficient RNA replication. Indeed, SFV is one of the most efficiently replicating viruses known. Within a few hours up to 200.000 copies of the plus-RNAs are made in a single cell. Because of the abundance of these molecules practically all ribosomes of the infected cell will be enrolled in the synthesis of the virus encoded proteins, thus overtaking host protein synthesis (34), and pulse-labelling of infected cells results in almost exclusive labelling of viral proteins. During a normal infection $10^5$ new virus particles are produced from one single cell, which calculates to at least $10^8$ protein molecules encoded by the viral genome (5).

3. Cytoplasmic replication. SFV replication occurs in the cell cytoplasm, where the virus replicase transcribes and caps the subgenomes for production of the structural proteins (19). It would obviously be very valuable to include this feature in a cDNA expression system to eliminate the many problems that are encountered in the conventional "nuclear" DNA expression systems, such as mRNA splicing, limitations in transcription factors, problems with capping efficiency and mRNA transport.

4. Late onset of cytopathic effects. The cytopathic effects in the infected cells appear rather late during infection. Thus, there is an extensive time window from about 4 hours after infection to up to 24 hours after infection during which a very high expression level of the structural proteins is combined with negligible morphological change.

5. Broad host range. This phenomenon is probably a consequence of the normal life cycle which includes transmission through arthropod vectors-to wild rodents and birds in nature. Under laboratory conditions, SFV infects cultured mammalian, avian, reptilian and insect cells (35) (Xiong, et al, loc. cit.)

6. In nature SFV is of very low pathogenicity for humans. In addition, the stock virus produced in tissue culture cells is apparently apathogenic. By means of specific mutations it is possible to create conditionally lethal mutations of SFV, a feature that is of great use to uphold safety when mass production of virus stocks is necessary.

In the nucleotide and amino acid sequences the following abbreviations have been used in this specification:

Ala, alanine; 11e, isoleucine; leu, leucine; Met, methionine; Phe, phenylalanine; Pro, proline; Trp, tryptophan; Val, valine; Asn, asparagine; Cys, cysteine; Gln, glutamine; Gly, glycine; Ser, serine; Thr, threonine; Tys, tyrosine; Arg, arginine; His, histidine; Lys, lysine; Asp, aspartic acid; Glu, glutamic acid; A, adenine; C, cytosine; G, guanine; T, thymine; U, uracil.

The materials and the general methodology used in the following examples are disclosed below.

1. Materials. Most restriction enzymes, DNA Polymerase I, Klenow fragment, calf intestinal phosphatase, T4 DNA ligase and T4 Polynucleotide kinase were from Boehringer (Mannheim, FRG). SphI, StuI and Kpni together with RNase inhibitor (RNasin) and SP6 Polymerase were from Promega Biotec (Madison, Wis.). Sequenase (Modified T7 polymerase) was from United States Biochemical (Cleveland, Ohio). Proteinase K was from Merck (Darmstadt, FRG). Ribonucleotides, deoxyribonucleotides, dideoxyribonucleotides and the cap analogue $m^7G(5')ppp(5')G$ were from Pharmacia (Sweden). Oligonucleotides were produced using an Applied Bio-systems synthesizer 380B followed by HPLC and NAP-5 (Pharmacia) purification. Spermidine, phenylmethylsulfonyl fluoride (PMSF), diethylpyrocarbonate (DEPC), bovine serum albumin (BSA), creatine phosphate and creatine phosphokinase were from Sigma (St. Louis, Mo.). Pansorbin was from CalBiochem (La Jolla, Calif.). Agarose was purchased from FMC BioProducts (Rockland, Me.), and acrylamide from BioRad (Richmond, Calif.). L-[$^{35}$S]methionine and $\alpha$-[$^{35}$S]-dATP-$\alpha$-S were from Amersham.

2. Virus growth and purification: BHK-21 cells were grown in BHK medium (Gibco Life Technologies, Inc., New York) supplemented with 5% fetal calf serum, 10% tryptose phosphate broth, 10 mM HEPES (N-2-hydroxyethylpiperazine-N'-2-ethanesulfonic acid) and 2 mM glutamine. 90% confluent monolayers were washed once with PBS and infected with SFV in MEM containing 0.2% bovine serum albumin (BSA), 10 mM HEPES and 2 mM glutamine at a multiplicity of 0.1. Twenty-four hours post infection (p.i.) the medium was collected and cell debris removed by centrifugation at 8.000 xg for 20 min at 4° C. The virus was pelleted from the medium by centrifugation at 26.000 rpm for 1.5 h in an SW28 rotor at 4° C. The virus was resuspended in TN containing 0.5 mM EDTA.

3. Metabolic labeling and immunoprecipitation. Confluent monolayers of BHK cells grown in MEM supplemented with 10 mM HEPES, 2 mM glutamine, 0.2% BSA, 100 IU/mol of penicillin and 100 µg/ml streptomycin, were infected at a multiplicity of 50 at 37° C. After 1 h p.i. the medium was replaced with fresh medium and growth continued for 3.5 h. The medium was removed and cells washed once with PBS and overlayed with methionine-free MEM containing 10 mM HEPES and 2 mM glutamine. After 30 min at 37° C. the medium was replaced with the same containing 100 µCi/ml of [$^{35}$S]methionine (Amersham) and the plates incubated for 10 min at 37° C. The cells were washed twice with labeling medium containing 10× excess methionine and then incubated in same medium for various times. The plates were put on ice, cells washed once with ice-cold PBS and finally lysis buffer (1% NP-40–50 mM Tris-HCl, pH 7.6–150 mM NaCl2 mM EDTA) containing 10 µg/ml PMSF (phenylmethylsulfonyl fluoride) was added. Cells were scraped off the plates, and nuclei removed by centrifugation at 6.000 rpm for 5 min at 4° C. in an Eppendorf centrifuge. Immunoprecipitations of proteins was performed as described (31). Briefly, antibody was added to lysate and the mixture kept on ice for 30 min. Complexes were recovered by binding to Pansorbin for 30 min on ice. Complexes were washed once with low salt buffer, once with high salt buffer, and once with 10 mM Tris-HCl, pH 7.5, before heating with gel loading buffer. To precipitate immunoprecipitate particular proteins, SDS was added to 0.1% and the mixture heated to 95° C. for 2 min followed by addition of 10 volumes of lysis buffer. Antibodies employed for the immunoprecipitation are as follows. Anti-E1 [8.139], anti-E2 [5.1] (36), and anti-C [12/2] (37) monoclonals have been described. The human transferrin receptor was precipitated with the monoclonal antibody OKT-9 in ascites fluid. This preparation was provided by Thomas Ebel at our laboratory using a corresponding hybridoma cell line obtained from ATCC (American Type Culture Collection) No CRL 8021. Polyclonal rabbit anti-mouse dhfr was a kind gift from E. Hurt (European Molecular Biology Laboratory, Heidelberg, FRG) and rabbit anti-lysozyme has been described (38).

4. Immunofluorescence. To perform indirect immunofluorescence, infected cell monolayers on glass coverslips were rinsed twice with phosphate-buffered saline (PBS) and fixed in −20° C. methanol for 6 min. After fixation, the methanol was removed and the coverslip washed 3 times with PBS. Unspecific antibody binding was blocked by incubation at room temperature with PBS containing 0.5% gelatin and 0.25% BSA. The blocking buffer was removed and replaced with same buffer containing primary antibody. After 30 min at room temperature the reaction was stopped by washing 3 times with PBS. Binding of secondary antibody (FITC-conjugated sheep anti-mouse [BioSys, Compiégne, France]) was done as for the primary antibody. After 3 washes with PBS and one rinse with water the coverslip was allowed to dry before mounting in Moviol 4–88 (Hoechst, Frankfurt am Main, FRG) containing 2.5% DABCO (1,4-diazobicyclo-[2.2.2]-octane).

5. DNA procedures. Plasmids were grown in *Escherichia coli* DH5α (Bethesda Research Laboratories) [recA endA1 gyrA96 thi1 hsdR17 supE44 relA1 Δ(lacZYA-argF)U169 φ80dlacZΔ(M15)]. All basic DNA procedures were done essentially as described (39). DNA fragments were isolated from agarose gels by the freeze-thaw method (40) including 3 volumes of phenol during the freezing step to increase yield and purity. Fragments were purified by benzoyl-naphthoyl-DEAE (BND) cellulose (Serva Feinbiochemica, Heidelberg, FRG) chromatography (41). Plasmids used for production of infectious RNA were purified by sedimentation through 1M NaCl followed by banding in CsCl (39). In some cases plasmids were purified by Qiagen chromatography (Qiagen Gmbh, Düsseldorf, FRG).

6. Site-directed oligonucleotide mutagenesis. For oligonucleotide mutagenesis, relevant fragments of the SFV cDNA clone were subcloned into M13mp18 or mp 19 (42) and transformed (43) into DH5αFIQ [endA1 hsdR1 supE44 thi1 recA1 gyrA96 relA1 φ80dlacΔ(M15) Δ(lacZYA-argF) U169/F'proAB lacI$^q$ lacZΔ(M15) Tn 5] (Bethesda Research Laboratories). RF DNA from these constructs was transformed into RZ1032 (44) [Hfr KL16 dut1 ung1 thi1 relA1 supE44 zbd279:Tn10], and virus grown in the presence of uridine to incorporate uracil residues into the viral genome. Single stranded DNA was isolated by phenol extraction from PEG precipitated phage. Oligonucleotides were synthesized on an Applied Biosystems 380B synthesizer and purified by gel filtration over NAP-5 columns (Pharmacia). The oligonucleotides 5'-CGGCCAGTGAATTCTGATTGGATC CCGGGTAATTAATTGAATTACATCCCTACGCAAACG, (SEQ ID NO.:13) 5'-GCGCACTATTATAGCACCGGCTC CCGGGTAATTAATTGACGCAAACGTTT-TACGCCGC CGG (SEQ ID NO.:14) and 5'-GCGCACTATTATAGCACCATGGATCCGGGTAATTA ATTGACGTTTTACGGCCGCCGGTGGCG (SEQ ID NO.:15) were used to insert the new linker sites [BamHI-SmaI-XmaI] into the SFV cDNA clone. The oligonucleotides 5'-CGGCGGTCCTAGATTGGTGCG (SEQ ID NO.:16) and 5'-CGCGGGCGCCACCGGCGGCCG (SEQ ID NO.:17) were used as sequencing primers (SP1 and SP2) up- and downstream of the polylinker site. Phosphorylated oligonucleotides were used in mutagenesis with Sequenase (Unites States Biochemicals, Cleveland, Ohio) as described earlier (44, 45). In vitro made RF forms were transformed into DH5αFIQ and the resulting phage isolates analyzed for the presence of correct mutations by dideoxy sequencing according to the USB protocol for using Sequenase. Finally, mutant fragments were reinserted into the full-length SFV cDNA clone. Again, the presence of the appropriate mutations was verified by sequencing from the plasmid DNA. Deletion of the 6K region has been described elsewhere.

7. In vitro transcription. SpeI linearized plasmid DNA was used as template for in vitro transcription. RNA was synthesized at 37° C. for 1 h in 10–50 μl reactions containing 40 mM Tris-HCl (pH 7.6), 6 mM spermidine-HCl, 5 mM dithiothreitol (DTT), 100 μg/ml of nuclease free BSA, 1 mM each of ATP, CTP and UTP, 500 μM of GTP, 1 unit/μl of RNasin and 100–500 units/ml of SP6 RNA polymerase. For production of capped transcripts (46), the analogs m$^7$G(5') ppp(5')G or m$^7$G(5')ppp(5')A were included in the reaction at 1 mM. For quantitation of RNA production, trace amounts of [α-$^{32}$P]-UTP (Amersham) were included in the reactions and incorporation measured from trichloroacetic acid precipitates. When required, DNA or RNA was digested at 37° C. for 10 min by adding DNase 1 or RNase A at 10 units/μg template or 20 μg/ml respectively.

8. RNA transfection. Transfection of BHK monolayer cells by the DEAE-Dextran method was done as described previously (47). For transfection by electroporation, RNA was added either directly from the in vitro transcription reaction or diluted with transcription buffer containing 5 mM DTT and 1 unit/μl of RNasin. Cells were trypsinized, washed once with complete BHK-cell medium and once with ice-cold PBS (without MgCl$_2$ and CaCl$_2$) and finally resuspended in PBS to give 10$^7$ cells/ml. Cells were either used directly or stored (in BHK medium) on ice over night. For electroporation, 0.5 ml of cells were transferred to a 0.2 cm cuvette (BioRad), 10–50 μl of RNA solution added and the solution mixed by inverting the cuvette. Electroporation was performed at room temperature by two consecutive pulses at 1.5 kV/25 μF using a BioRad Gene Pulser apparatus with its pulse controller unit set at maximum resistance. After incubation for 10 min, the cells were diluted 1:20 in complete BHK-cell medium and transferred onto tissue culture plates. For plaque assays, the electroporated cells were plated together with about 3×10$^5$ fresh cells per ml and incubated at 37° C. for 2 h, then overlayed with 1.8% low melting point agarose in complete BHK-cell medium. After incubation at 37° C. for 48 h, plaques were visualized by staining with neutral red.

9. Gel electrophoresis. Samples for Sodium dodecyl sulfate-polyacrylamide gel electrophoresis (SDS-PAGE) were prepared and run on 12% separating gels with a 5% stacking gel as previously described (48). For resolving the 6K peptide, a 10%–20% linear acrylamide gradient gel was used. Gels were fixed in 10% acetic acid–30% methanol for 30 min before exposing to Kodak XAR-5 film. When a gel was prepared for fluorography (49), it was washed after fixation for 30 min in 30% methanol and then soaked in 1M sodium salicylate–30% methanol for 30 min before drying. Nucleic acids were run on agarose gels using 50 mM Tris-borate–2.5 mM Na$_2$EDTA as buffer. For staining 0.2 μg/ml of ethidium bromide was included in the buffer and gel during the run.

EXAMPLE 1

In this example a full-length SFV cDNA clone is prepared and placed in a plasmid containing the SP6 RNA polymerase promoter to allow in vitro transcription of full-length and infectious transcripts. This plasmid which is designated pSP6-SFV4 has been deposited on 28 Nov. 1991 at PHLS Centre for Applied Microbiology & Research European Collection of Animal Cell Cultures, Porton Down, Salisbury, Wiltshire, U.K:, and given the provisional accession number 91112826.

Figure 4A:
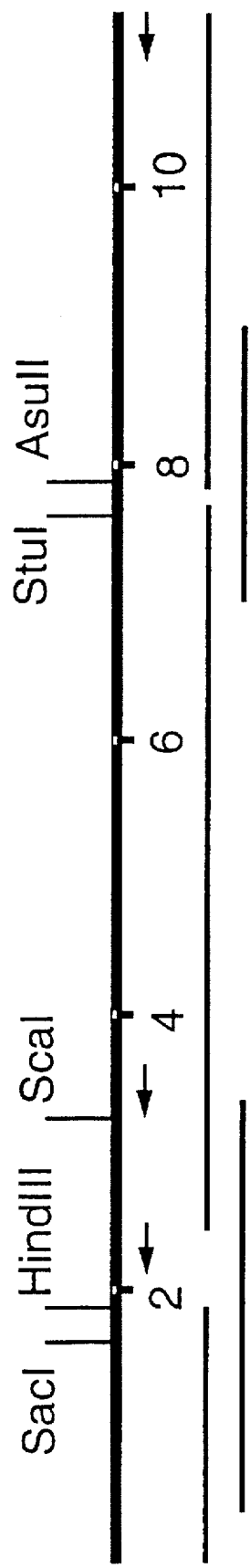
FIG. 4A shows a schematic restriction map of the SFV genome; primers used for initiating cDNA synthesis are indicated as arrows, and the cDNA inserts used to assemble the final clone are showed as bars.
Figure 4:
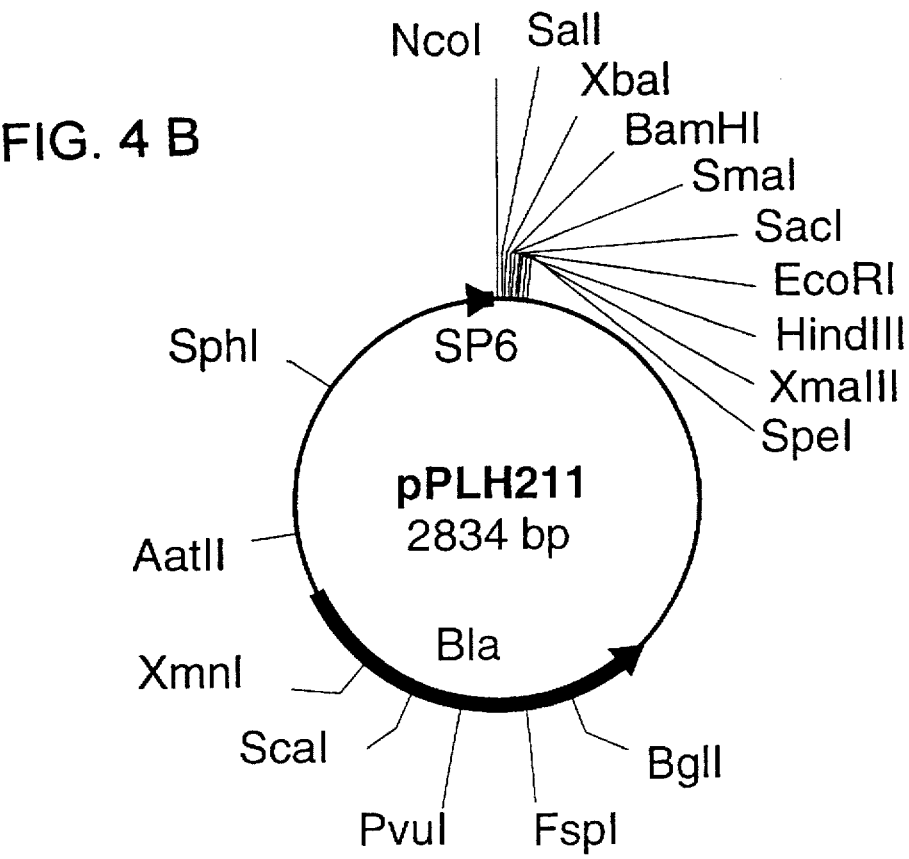
FIG. 4 A–D show the construction of full-length infectious clones of SFV.
Figure 4:
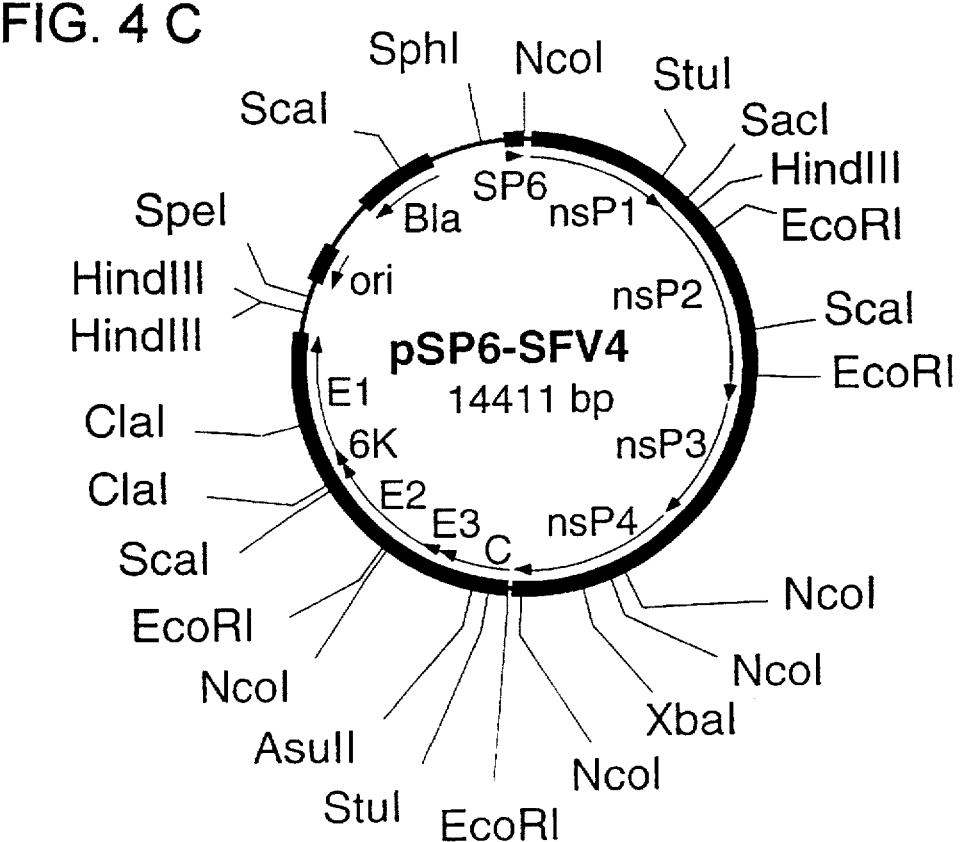
Figure 4D:
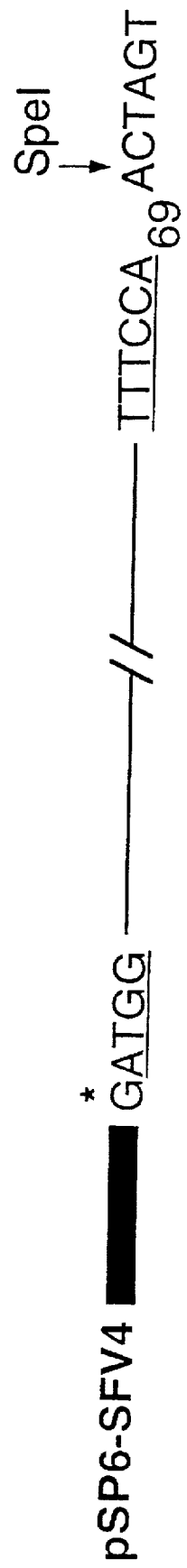
FIG. 4D shows the resulting plasmid pSP6-SFV4.
Figure 6:
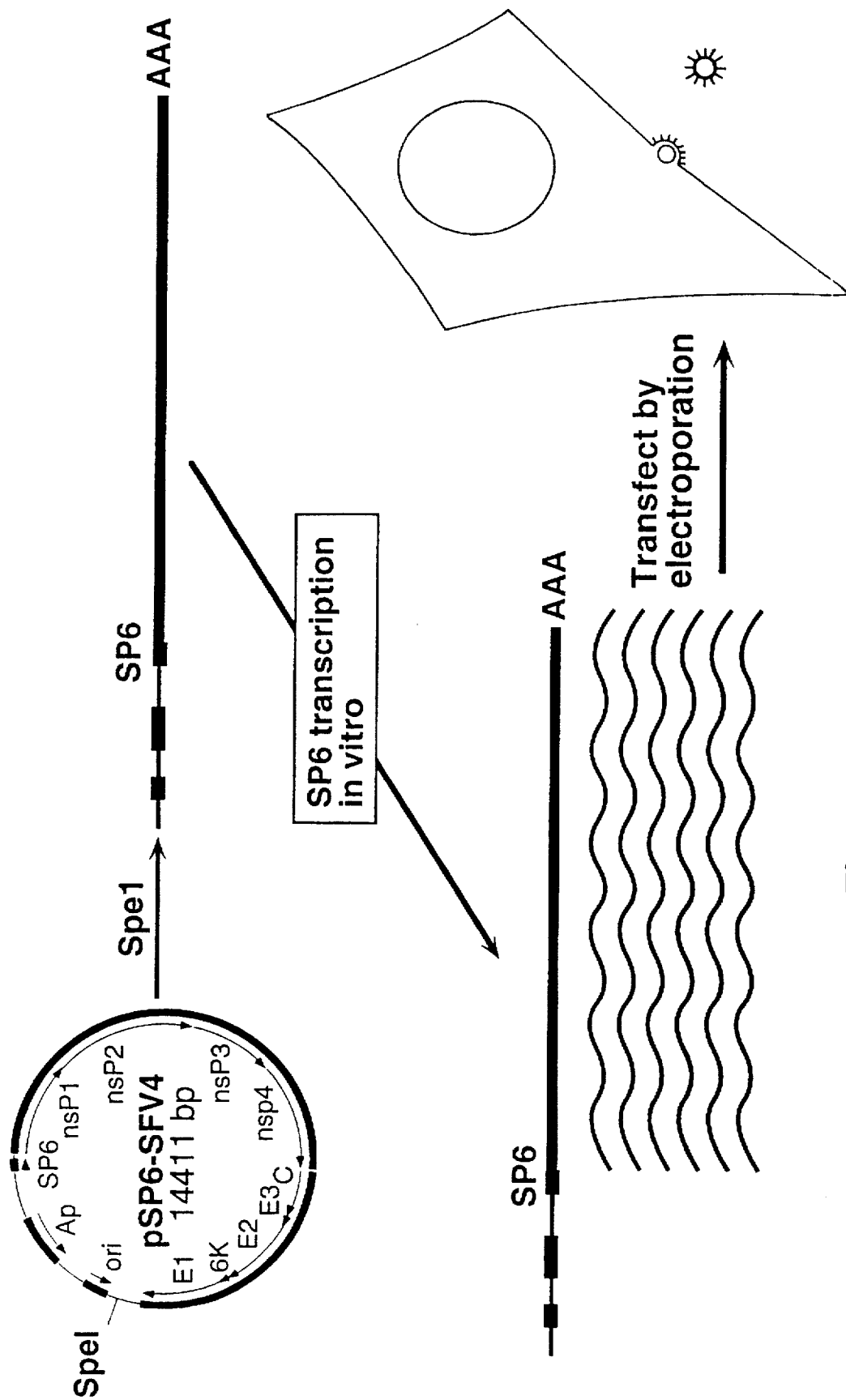
FIG. 6 shows an SFV cDNA expression system for the production of virus after transfection of in vitro made RNA into cell.

As illustrated in FIG. 4A–C the strategy for construction the SFV clone was to prime cDNA synthesis on several positions along the template RNA downstream of suitable restriction endonuclease sites defined by the known nucleotide sequence of the SFV RNA molecule. Virus RNA was isolated by phenol-chloroform extraction from purified virus (obtainable among others from the Arbovirus collection in Yale University, New Haven, USA) and used as template for cDNA synthesis as previously described (50). First strand synthesis was primed at three positions, using 5'-TTTCTCGTAGTTCTCCTCGTC (SEQ ID NO.:18) as primer-1 (SFV coordinate 2042–2062) and 5'-GTTATCCCAGTGGTTGTTCTCGTAATA (SEQ ID NO.:19) as primer-2 (SFV coordinate 3323–3349) and an oligo-dT$_{12-18}$ as primer -3 (3' end of SFV) FIG. 4A).

Second strand synthesis was preceded by hybridization of the oligonucleotide 5'-ATGGCGGATGTGTGACATACACGACGCC (SEQ ID NO.:20) identical to the 28 first bases of the genome sequence of SFV) to the first strand cDNA. After completion of second strand synthesis cDNA was trimmed and in all cases except in the case of the primer-1 reaction, the double-stranded adaptor 5'-AATTCAAGCTTGCGGCCGCACTAGT/ GTTCGAACGCCGGCGTGATCA-3' (SEQ. ID. NO.21) (5'-sticky-EcoRi-HindIII-NotI-XmaIII-SpeI-blunt-3') was added and the cDNA cloned into EcoR1 cleaved pTZ18R (Pharmacia, Sweden) as described (51). The cloning of the 5' end region was done in a different way. Since SFV contains a HindIII site at position 1947, cDNA primed with primer-1 should contain this area and therefore HindIII could be used to define the 3' end of that cDNA. To obtain a restriction site at the very 5' end of the SFV, cDNA was cloned into SmaI-HindIII cut pGEM1 (Promega Biotec., Madison, Wis.). Since the SFV genome starts with the sequence 5'-ATGG, ligation of this onto the blunt CCC-3' end of the SmaI site created an NcoI site C'CATGG. Although the SFV sequence contains 3 NcoI sites, none of these are within the region preceding the HindIII site, and thus these 5' end clones could be further subcloned as NcoI-HindIII fragments into a vector especially designed for this purpose (see below). The original cDNA clones in pGEM1 were screened by restriction analysis and all containing inserts bigger than 1500 bp were selected for further characterization by sequencing directly from the plasmid into both ends of the insert, using SP6 or T7 sequencing primers. The SFV 5'-end clones in pTZ18R were sequenced using lac sequencing primers. To drive in vitro synthesis of SFV RNA the SP6 promoter was used. Cloning of the SFV 5' end in front of this promoter without adding too many foreign nucleotides required that a derivative of pGEM1 had to be constructed. Hence, pGEM1 was opened at EcoRI and Ba131 deletions were created, the DNA blunted with T4 DNA polymerase and an NcoI oligonucleotide (5'-GCCATGGC, (SEQ ID NO.:22) added. The clones obtained were screened by colony hybridization (39) with the oligonucleotide 5'-GGTGACACTATAGCCATGGC (SEQ ID NO.:23) designed to pick up (at suitable stringency) the variants that had the NcoI sequence immediately at the transcription initiation site of the SP6 promoter (G underlined). Since the Bal31 deletion had removed all restriction sites of the multicloning site of the original plasmid, these were restored by cloning a PvuI-NcoI fragment from the new variant into another variant of pGEM1 (pDH101) that had an NcoI site inserted at its HindIII position in the polylinker. This created the plasmid pDH201. Finally, the adaptor used for cloning the SFV cDNA was inserted into pDH201 between the EcoRI and PvuII sites to create plasmid pPLH211 (FIG. 4B). This plasmid was then used as recipient for SFV cDNA fragments in the assembly of the full-length clone by combining independent overlapping subclones using these sites. The fragments and the relevant restriction sites used to assemble the full-length clone, pSP6-SFV4, are depicted in (FIG. 4A). For the 5'-end, the selected fragment contained the proper SFV sequence 5'-ATGG, with one additional G-residue in front. When this G-residue was removed it reduced transcription efficiency from SP6 but did not affect infectivity of the in vitro made RNA. Thus, the clone used for all subsequent work contains the G-residue at the 5' end. For the 3'-end of the clone, a cDNA fragment containing 69 A-residues was selected. By inclusion of the unique SpeI site at the 3'-end of the cDNa, the plasmid can be linearized to allow for runoff transcription in vitro giving RNA-carrying 70 A-residues. FIG. 4C shows the 5' and 3' border sequences of the SFV cDNA clone. The general outline how to obtain and demonstrate infectivity of the full-length SFV RNA is depicted in FIG. 6. The complete nucleotide sequence of the pSP6-SFV4 SP6 transcript together with the amino acid sequences of the nonstructural and the structural polyproteins is shown in FIG. 5.

Typically, about 5 μg of RNA per 100 ng of template was obtained using 10 units of polymerase, but the yield could be increased considerably by the use of more enzyme. The conditions slightly differ from those reported earlier for the production of infectious transcripts of alphaviruses (52) (47). A maximum production of RNA was obtained with rNTP concentrations at 1 mM. However, since infectivity also is dependent on the presence of a 5' cap structure optimal infectivity was obtained when the GTP concentration in the transcription reaction was halved. This drop had only a marginal effect on the amounts of RNA produced but raised the specific infectivity by a factor of 3 (data not shown).

The cDNA sequence shown in FIGS. 5A–5Q has been used in the following examples. However, sequences having one or a few nucleotides, which differ from those shown in FIGS. 5A–5Q, could also be useful as vectors, even if these might be less efficient as illustrated above with the SFV cDNA sequence lacking the first 5'-G nucleotide in FIG. 5A.

EXAMPLE 2

In this example the construction of SFV DNA expression vectors is disclosed.

The cDNA clone coding for the complete genome of SFV obtained in Example 1 was used to construct a SFV DNA expression vector by deletion of the coding region of the 26S structural genes to make way for heterologous inserts. However, the nonstructural coding region, which is required for the production of the nsP1–4 replicase complex is preserved. RNA replication is dependent on short 5' (nt 1–247) (53, 54, 55) and 3' (nt 11423–11441) sequence elements (56, 57), and therefore, also these had to be included in the vector construct, as had the 26S promoter just upstream of the C gene (17, 18).

As is shown in FIG. 7A–7C, first, the XbaI (6640)-NsiI (8927) fragment from the SFV cDNA clone pSP6-SFV4 from Example 1 was cloned into pGEM7Zf(+) (Promega Corp., Wis., USA) (Step A). From the resulting plasmid, pGEM7Zf(+)-SFV, the EcoRI fragment (SFV coordinates 7391 and 88746) was cloned into M13mp19 to insert a BamHI-XmaI-SmaI polylinker sequence immediately downstream from the 26S promoter site using site-directed mutagenesis (step B). Once the correct mutants had been verified by sequencing from M13 ssDNA (single stranded), the EcoRI fragments were reinserted into pGEM7Zf(+)-SFV (step C) and then cloned back as XbaI-Nsλ fragments into pSP6-SFV4 (step D). To delete the major part of the cDNA region coding for the structural proteins of SFV, these plasmids were then cut with AsuII (7783) and NdeI (11033), blunted using Klenow fragment in the presence of all four nucleotides, and religated to create the final vectors designated pSFV1, pSFV2 and pSFV3, respectively (step E). The vectors retain the promoter region of the 26S subgenomic RNA and the last 49 amino acids of the E1 protein as well as the complete non-coding 3' end of the SFV genome.

In the vectors the subgenomic (26S) protein coding portion has been replaced with a polylinker sequence allowing the insertional cloning of foreign cDNA sequences under the 26S promoter. As is shown in FIG. 8 these three vectors have the same basic cassette inserted downstream from the 26S promoter, i.e. a polylinker (BamHI-SmaI-XmaI) followed by a translational stop codon in all three reading frames. The vectors differ as to the position where the polylinker cassette has been inserted. In pSFV1 the cassette is situated 31 bases downstream of the 26S transcription initiation site. The initiation motif of the capsid gene translation is identical to the consensus sequence (58). Therefore, this motif has been provided for in pSFV2, where it is placed immediately after the motif of the capsid gene. Finally, pSFV3 has the cassette placed immediately after the initiation codon (AUG) of the capsid gene. Sequencing primers (SP) needed for checking both ends of an insert have been designed to hybridize either to the 26S promoter region (SP1), or to the region following the stop codon cassette (SP2).

Note that the 26S promoter overlaps with the 3'-end of the nsP4 coding region. For pSFV2, the cloning site is positioned immediately after the translation initiation site of the SFV capsid gene. For pSFV3, the cloning site is positioned three nucleotides further downstream, i.e. immediately following to the initial AUG codon of the SFV capsid gene. The three translation stop codons following the polylinker are boxed. The downstream sequencing primer (SP1) overlaps with the 26S promoter, and the upstream sequencing primer (Sp2) overlaps the XmaIII site.

EXAMPLE 3

In this example an in vivo packaging system encompassing helper virus vector constructs is prepared.

Figure 7A:
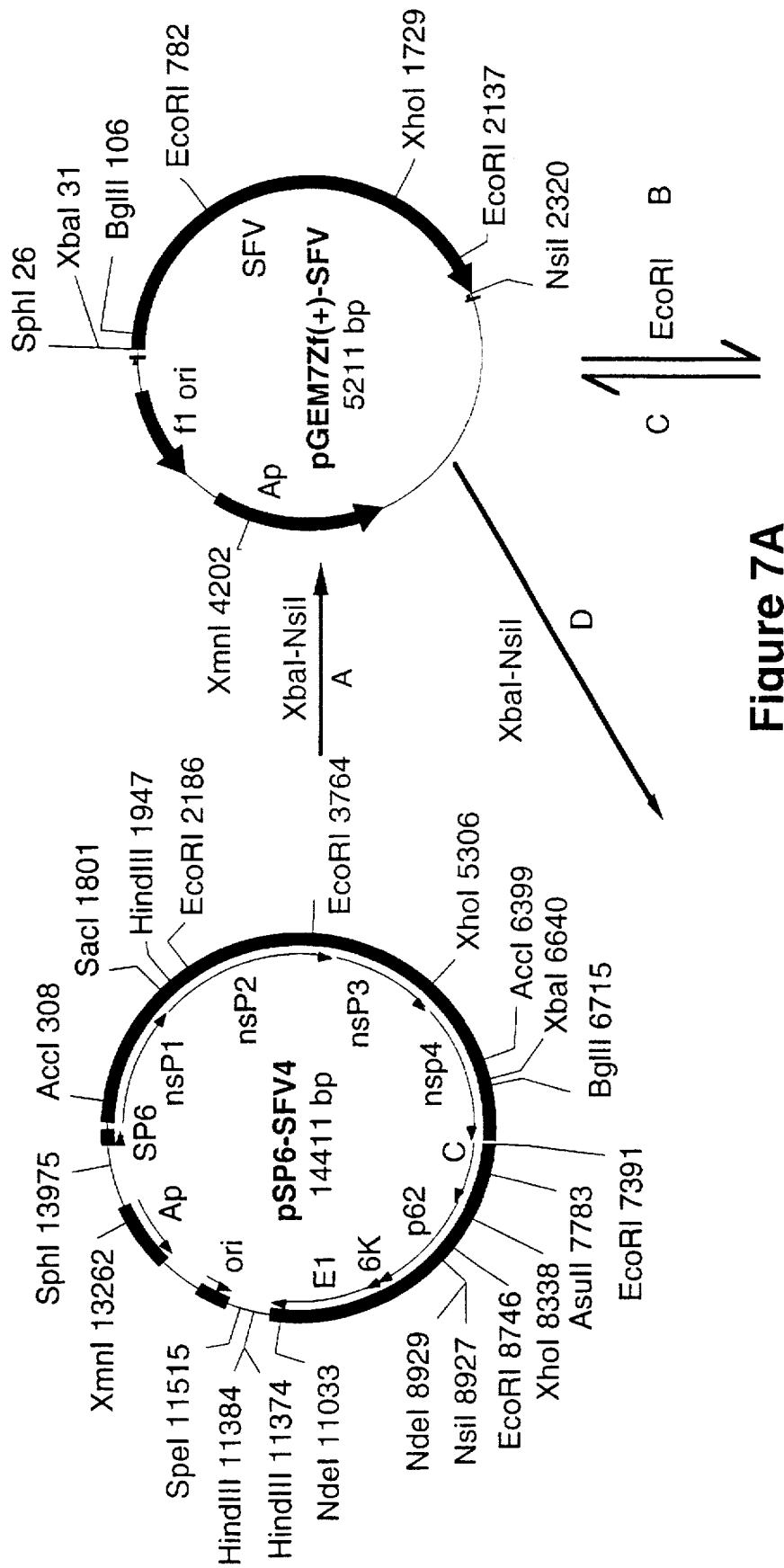
FIGS. 7A–7C show the construction of the SFV expression vectors pSFV1-3 and of the Helper 1.
Figure 7B:
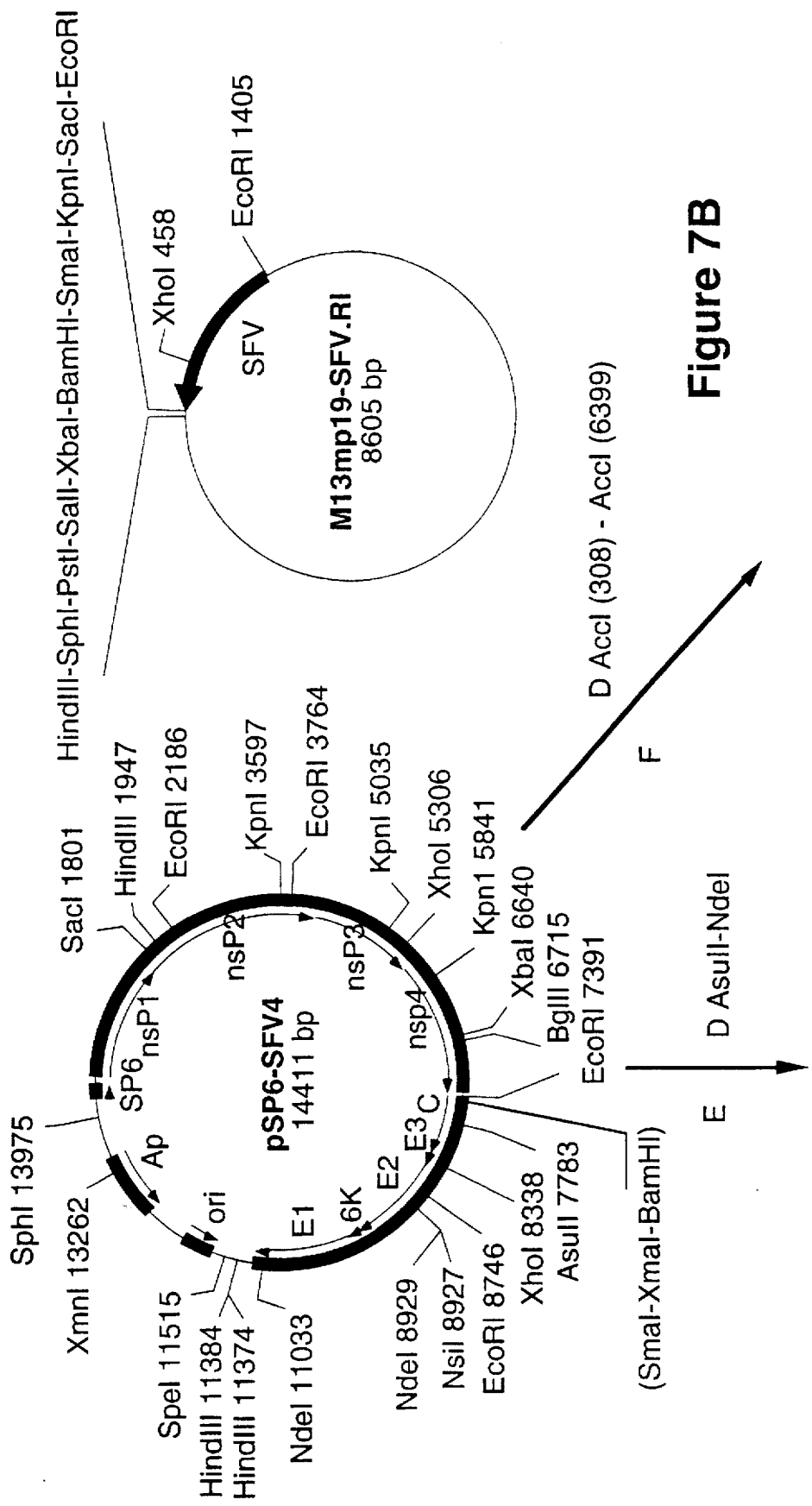
Figure 7C:
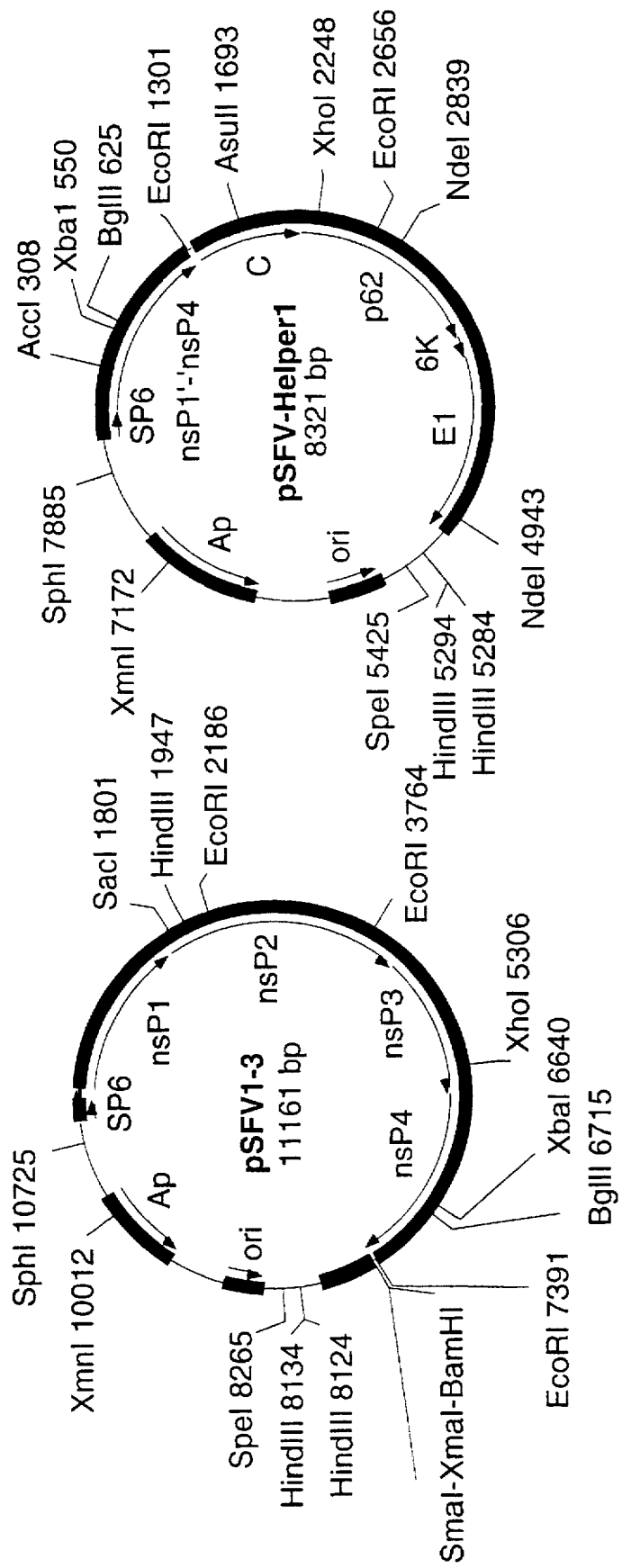
Figure 9:
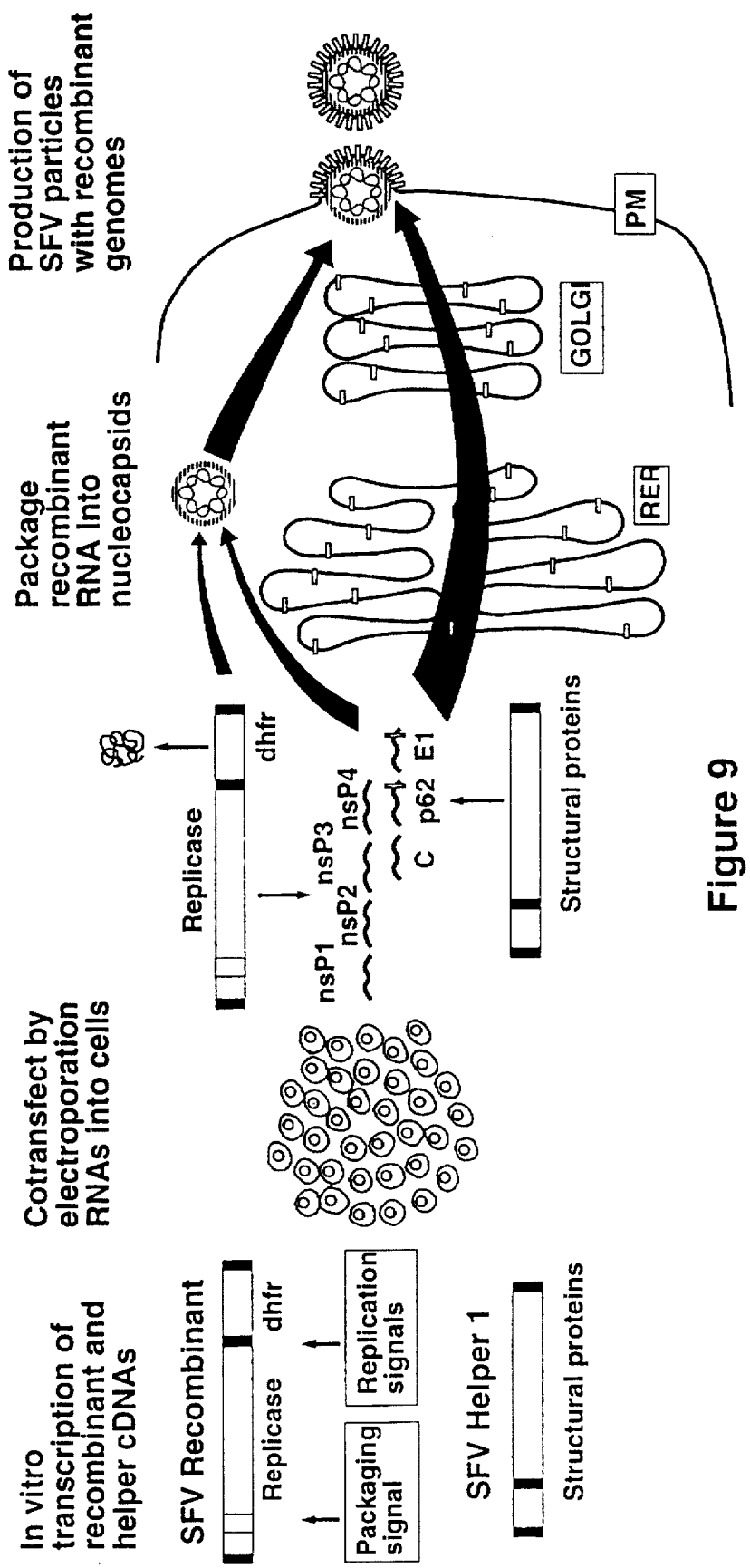
FIG. 9 is a schematic presentation of in vivo packaging of pSFV1-dhfr RNA into infectious particles using helper trans complementation; (dhfr means dihydrofolate reductase)

The system allows SFV variants defective in structural protein functions, or recombinant RNAs derived from the expression vector construct obtained in Example 2, to be packaged into infectious virus particles. Thus, this system allows recombinant RNAs to be introduced into cells by normal infection. The helper vector, called pSFV-Helper1, is constructed by deleting the region between the restriction endonuclease sites AccI (308) and AccI (6399) of pSP6-SFV4 obtained in Example 1 by cutting and religation as shown in FIG. 7B, step F. The vector retains the 5' and 3' signals needed for RNA replication. Since almost the complete nsP region of the Helper vector is deleted, RNA produced from this construct will not replicate in the cell due to the lack of a functional replicase complex. As is shown in FIG. 9, after transcription in vitro of pSFV1-recombinant and helper cDNAs, helper RNA is cotransfected with the pSFV1 - recombinant derivative, the helper construct providing the structural proteins needed to assemble new virus particles, and the recombinant providing the nonstructural proteins needed for RNA replication, SFV particles comprising recombinant genomes being produced. The cotransfection is preferably produced by electroporation as is disclosed in Example 6 and preferably BHK cells are used as host cells.

To package the RNA a region at the end of nsP1 is required, ah area which has been shown to bind capsid protein (57, 59). Since the Helper lacks this region, RNA derived from this vector will not be packaged and hence, transfections with recombinant and Helper produces only virus particles that carry recombinant-derived RNA. It follows that these viruses cannot be passaged further and thus provide a one-step virus stock. The advantage is that infections with these particles will not produce any viral structural proteins.

EXAMPLE 4

This example illustrates the construction of variants of the full-length SFV cDNA clone from Example 1 that allow insertion of foreign DNA sequences encoding foreign epitopes, and the production of recombinant (chimaeric) virus carrying said foreign epitopes as integral parts of the p62, E2 or E1 spike proteins.

To this end, a thorough knowledge of the function, topology and antigenic structure of the E2 and E1 envelope proteins has been of the essence. Earlier studies on the pathogenicity of alphaviruses have shown that antibodies against E2 are type-specific and have good neutralizing activity while those against E1 generally are group-specific and are nonneutralizing (5). However, not until recently have antigenic sites of the closely related alphaviruses SFV, Sindbis, and Ross River been mapped and correlated to the level of amino acid sequence (60, 61, 62, 63). These studies have shown that the most dominant sites in question are at amino acid positions 216, 234 and 246–251 of the SFV E2 spike protein. Interestingly, these three sites are exactly the same as the ones predicted by computer analysis. In the present example domain 246–251 was used, since this area has a highly conserved structure and hydropathy profile within the group of alpha-viruses. Insertion of a gene encoding a foreign epitope into the 246–251 region of the pSP6-SFV4 p62 protein yields particles with one new epitope on each heterodimer, i.e. 240 copies.

To create a unique restriction endonuclease site that would allow specific insertion of foreign epitopes into the E2 portion of the SFV genome, a BamHI site was inserted by site directed mutagenesis using the oligonucleotide 5'-GATCGGCCTAGGAGCCGAGAGCCC-3, (SEQ ID NO.:24)

EXAMPLE 5

In this example a conditionally lethal variant of SFV is constructed from the SFV cDNA obtained in Example 1, which variant carries a mutation in the p62 protein resulting in a noncleavable from of said protein, with the result that this variant as such cannot infect new host cells, unless first cleaved with exogenously added protease.

Figure 10:
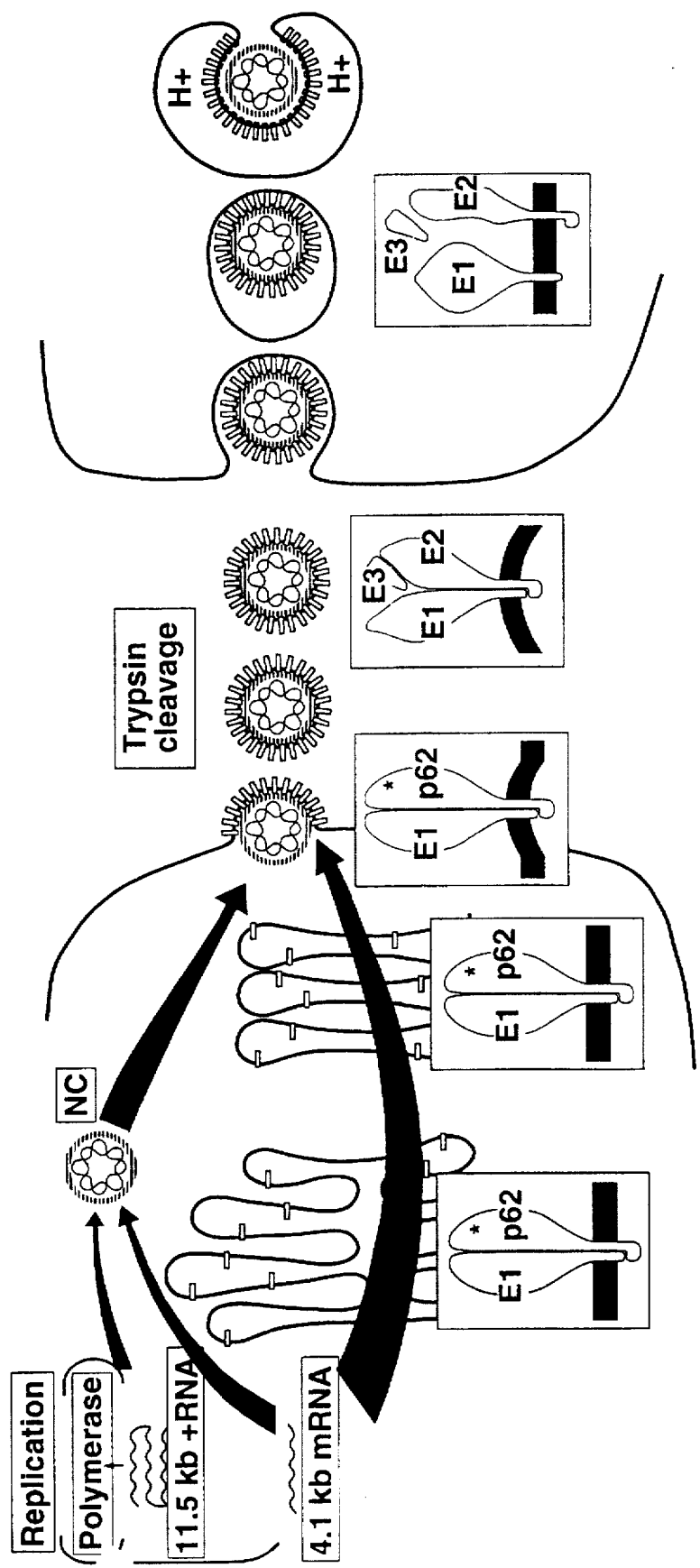
FIG. 10 shows the use of trypsin to convert p62-containing noninfectious virus particles to infectious particles by cleavage of p62 to E2 and E3.

As illustrated in FIG. 10, this construct can be advantageously used as a vaccine carrier for foreign epitopes, since this form of the virus cannot enter new host cells although assembled with wild type efficiency in transfected cells. The block can be overcome by trypsin treatment of inactive virus particles. This converts the particle into a fully entry-competent form which can be used for amplification of this virus variant stock.

Once activated the SFV variant will enter cells normally through the endocytic pathway and start infection. Viral proteins will be made and budding takes place at the plasma membrane. However, all virus particles produced will be of inactive form and the infection will thus cease after one round of infection. The reason for the block in infection proficiency is a mutation which has been introduced by site directed mutagenesis into the cleavage site of p62. This arginine to leucine substitution (at amino acid position 66 of the E3 portion of the p62 protein) changes the consensus features of the cleavage site so that it will not be recognized by the host cell proteinase that normally cleaves the p62 protein to the E2 and E3 polypeptides during transport to the cell surface. Instead, only exogenously added trypsin will be able to perform this cleavage, which in this case occurs at the arginine residue 65 immediately preceding the original cleavage site. As this cleavage regulates the activation of the entry function potential of the virus by controlling the binding of the entry spike subunit, the virus particle carrying only uncleaved p62 will be completely unable to enter new host cells.

The creation of the cleavage deficient mutation E2 has been described earlier (29). An AsuII-NsλI fragment spanning this region was then isolated and cloned into the full-length cDNA clonepSP6-SFV4.

EXAMPLE 6

In this example transfection of BHK cells with SFV RNA molecules transcribed in vitro from full-length cDNA from Example 1 or variants thereof or the SFV vectors from Example 2, which comprise exogenous DNA, is disclosed. The transfection is carried out by electroporation which is shown to be very efficient at optimized conditions.

BHK cells were transfected with the above SFV RNA molecules by electroporation and optimal conditions were determined by varying parameters like temperature, voltage, capacitance, and number of pulses. Optimal transfection was obtained by 2 consecutive pulses of 1.5 kV at 25 µF, under which negligible amounts of cells were killed. It was found that it was better to keep the cells at room temperature than at 0° C. during the whole procedure. Transfection by electroporation was also measured as a function of input RNA. As expected, an increase in transfection frequency was not linearly dependent on RNA concentration, and about 2 µg of cRNA were needed to obtain 100% transfection.

On comparison with conventional transfection, this is a great improvement. For example, with DEAE-Dextran transfection optimally, only 0.2% of the cells were transfected.

EXAMPLE 7

This example illustrates heterologous gene expression driven by the SFV vector, pSFV1 from Example 2, for genes encoding the 21 kD cytoplasmic mouse dihydrofolate reductase (dhfr), the 90 kD membrane protein human transferrin receptor (TR), and finally the 14 kD secretory protein chicken lysozyme. The dhfr gene was isolated from pGEM2-dhfr (64) as a BamHI-HindIII fragment blunted with Klenow fragment and inserted into SmaI-cut pSFV1. The transferrin receptor gene was first cloned from pGEM1-TR (64, 65) as an XbaI-EcoRI fragment into pGEM7ZF(+) and subsequently from there as a BamHI fragment into pSFV1. Finally, a BamHI fragment from pGEM2 carrying the lysozyme gene (21) was cloned into pSFV1.

To study the expression of the heterologous proteins, in vitro-made RNA of the dhfr and TR constructs was electroporated into BHK cells. RNA of wild type SFV was used as control. At different time points post electroporation (p.e.) cells were pulse-labeled for 10 min followed by a 10 min chase, whereafter the lysates were analyzed by gel electrophoresis and autoradiography. The results are shown in FIGS. 11A–11E. More specifically, BHK cells were transfected with RNAs of wild type SPV, and pSFV1-dhfr, and pSFV1-TR, pulse-labeled at 3, 6, 9, 12, 15 and 24 h p.e. Equal amounts of lysate were run on a 12% gel. The 9 h sample was also used in immunoprecipitation (IP) of the SFV, the dhfr and the transferrin receptor proteins. Cells transfected with pSFV1-lysozyme were pulse-labeled at 9 h p.e. and then chased for the times (hours) indicated. An equal portion of lysate or medium was loaded on the 13.5% gel. IP represents immunoprecipitation from the 1 h chase lysate sample. The U-lane is lysate of labeled but untransfected cells. At 3 h p.e. hardly any exogenous proteins were made, since the incoming RNA starts with minus strand synthesis which does not peak until about 4–5 h p.e. (5). At this time point, almost all labeled proteins were of host origin. In contrast, at 6 h p.e. the exogenous proteins were synthesized with great efficiency, and severe inhibition of host protein synthesis was evident. This was even more striking at 9 h p.e., when maximum shut down of host protein synthesis had been reached. Efficient production of the heterologous proteins continued up to 24 h p.e., after which production slowed down (data not shown), indicating that the cells had entered a stationary phase.

Figure 11A:
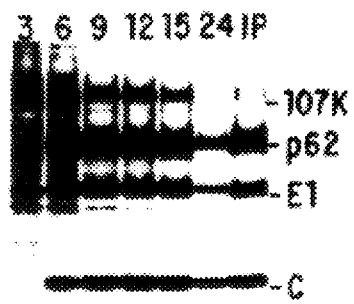
FIGS. 11A–11E show the expression of heterologous proteins in BHK cells upon RNA transfection by electroporation.
Figure 11B:
Figure 11C:
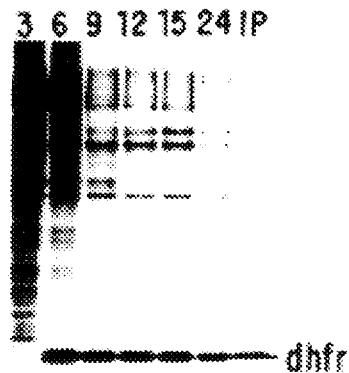
Figure 11D:
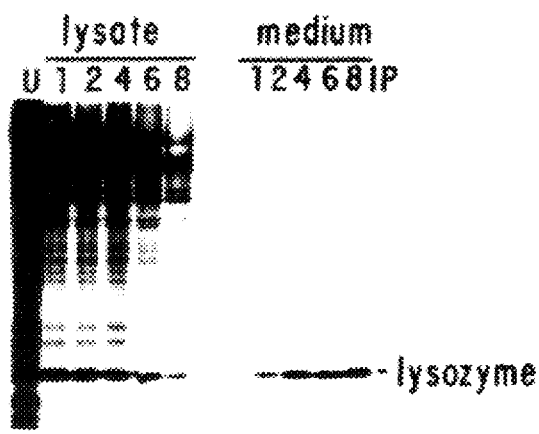

Since chicken lysozyme is a secretory protein, its expression was analyzed both from cell lysates and from the growth medium. Cells were pulse-labeled at 9 h p.e. and then chased up to 8 h. The results are shown in FIG. 11A–D. FIG. 11A shows the result of expression of wild-type viral proteins. FIG 11B shows the expression of human transferrin receptor. FIG. 11C shows the expression of mouse dihydrofolate reductase. FIG 11D shows the expression of chicken lysozyme. Although lysozyme was slowly secreted, almost all labeled material was secreted to the medium during the chase.

EXAMPLE 8

This example illustrates the present in vivo packaging system.

Figure 11E:
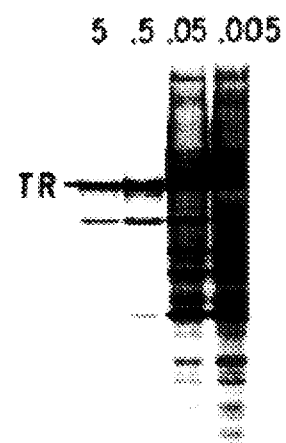

In vitro-made RNA of pSFV1-TR was mixed with Helper RNA at different ratios and these mixtures were co-transfected into BHK cells. Cells were grown for 24 h after which the culture medium was collected and the virus particles pelleted by ultracentrifugation. The number of infectious units (i.u.) was determined by immunofluorescence. It was found that a 1:1 ratio of Helper and recombinant most efficiently produced infectious particles, and on the average $5 \times 10^6$ cells yielded $2.5 \times 10^9$ i.u. The infectivity of the virus stock was tested by infecting BHK cells at different multiplicities of infection (m.o.i.). In FIG. 11E the results for expression of human transferrin receptor in BHK cells after infection by such in vivo packaged particles carrying pSFV1-TR recombinant RNA is shown to the lower right. 200 µl of virus diluted in MEM (including 0.5% BAS and 2 mM glutamine) was overlaid on cells to give m.o.i. values ranging from 5 to 0.005. After 1 h at 37° C., complete BHK medium was added and growth continued for 9 h, at which time a 10 min pulse (100 µCi $^{35}$S-methionine/ml) and 10 min chase was performed, and the cells dissolved in lysis buffer. 10 µl out of the 300 µl lysate (corresponding to 30,000 cells) was run on the 10% gel, and the dried gel was exposed for 2 h at –70° C. Due to the high expression level, only 3,000 cells are needed to obtain a distinct band on the autoradiograph with an overnight exposure.

Thus, it was found that efficient protein production and concomitant host protein shut-off occurred at about 1 i.u. per cell. Since one SFV infected cell produces on the average $10^8$ capsid protein molecules, it follows that a virus stock produced from a single electroporation can be used to produce $10^{17}$ protein molecules equaling about 50 mg of protein.

From the foregoing experimental results it is obvious that the present invention is related to very useful and efficient expression system which lacks several of the disadvantages of the hitherto existing expression system. The major advantages of the present system are shortly summarized as follows:

(1) High titre recombinant virus stocks can be produced in one day by one transfection experiment. There is no need for selection/screening, plaque purification and amplification steps. This is appreciated since an easy production of recombinant virus is especially important in experiments where the phenotypes of large series of mutants have to be characterized.

(2) The recombinant virus stock is free from helper virus since only the recombinant genome but not the helper genome contains a packaging signal.

(3) The recombinant virus can be used to infect the recombinant genome in a "natural" and non-leaky way into a large variety of cells including insect and most higher eucaryotic cell types. Such a wide host range is very useful for an expressions system especially when cell-type-specific posttranslational modification reactions are required for the activity of the expressed protein.

(4) The level of protein expression obtained is extremely high, the level corresponding to those of the viral proteins during infection. There is also a host cell protein shut-off which makes it possible to follow the foreign proteins clearly in cell lysates without the need for antibody mediated antigen concentration. This will facilitate DNA expression experiments in cell biology considerably. Furthermore, problems of interference by the endogenous counter part to an expressed protein (i.e. homo-oligomerization reactions) can be avoided.

EXAMPLE 9

This example illustrates epitope carriers. A very important example where vaccine development is of the utmost importance concerns the acquired immunodeficiency syndrome (AIDS) caused by the human immunodeficiency virus HIV-1 (66, 67). So far, all attempts to produce an efficient vaccine against HIV-1 have failed, although there was a very recent report that vaccination with disrupted SIV-1 (Simian immunodeficiency virus) to a certain extent may give protection against infections of that virus (68). However, development of safe and effective vaccine against HIV-1 will be very difficult due to the biological properties of the virus. In the present example one epitope of HIV-1 was inserted into an antigenic domain of the E2 protein of SFV. The epitope used is located in glycoprotein gp120 of HIV-1, spanning amino acids 309–325. This forms the variable loop of HIV-1 and is situated immediately after an N-glycosylated site.

Figure 12B:
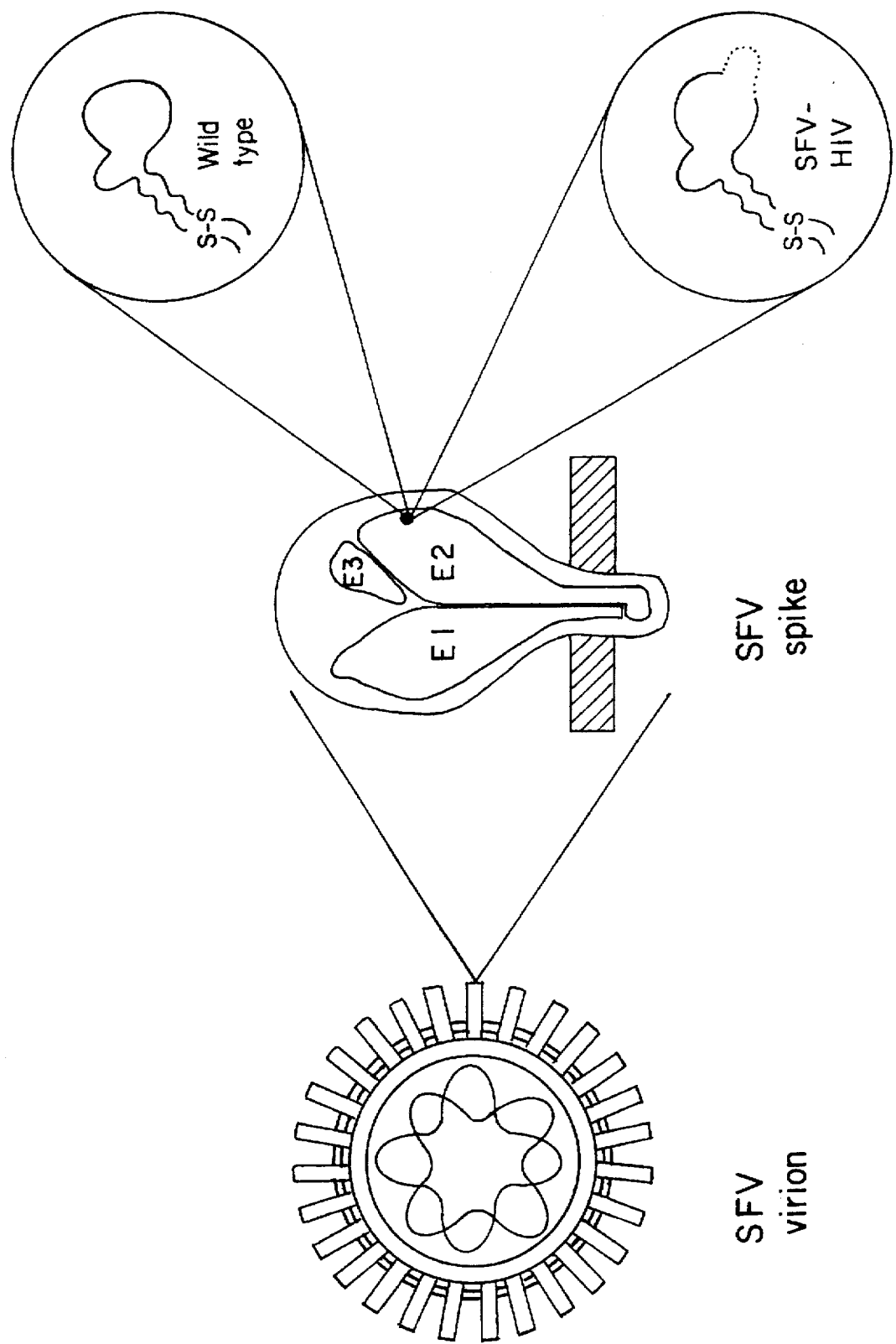

A chimaera was constructed where the 309–325 epitope of HIV was inserted into the BamHI site using cassette insertion of ready-made oligonucleotides encoding the HIV epitope. The required base substitutions at the BamHI site did not lead to any amino acid changes in the vector, although two amino acids (Asp and Glu) changed places. This change did not have any deleterious effect since in vitro made vector RNA induced cell infection with wild type efficiency. FIG. 12A shows the sequences in the area of interest in the epitope carrier. In preliminary experiments, it has been shown that chimaeric proteins were produced. The proteins can be immunoprecipitated with anti-HIV antibodies. It is to be expected that these are also used for production of chimaeric virus particles that can be used for vaccine preparation against HIV. Such particles are shown in FIG. 12B.

List of references

1) Bishop, D. H. L. (1990). Gene expression using insect cells and viruses. In current Opinion in Biotechnology, Vol. 1, Rosenberg, M., and Moss, B., eds. (London: Current Opinion Ltd.), pp. 62–67.
2) Moss, B. (1990). Regulation of Vaccinia virus transcription. Ann. Rev. Biochem. 59, 661–688.
3) Moss, B. and Flexner, C. (1989). Vaccinia virus expression vectors. Ann. N.Y. Acad Sci. 569, 86–103.
4) Garoff, H., Kondor-Koch, C., and Riedel, H. (1982). Structure and assembly of alphaviruses. Curr. Top. Microbiol. Immunol. 99, 1–50.
5) Strauss, E. G., and Strauss, J. H. (1986). Structure and replication of the alphavirus genome. In The Togaviridae and Flaviviridae, Vol. Schlesinger, S. S., and Schlesinger, M. J., eds (New York: Plenum Press), pp. 35–90.
6) Garoff, H., Frischauf, A.-M., Simons, K., Lehrach, H, and Delius, H. (1980). Nucleotide sequence of cDNA coding for Semliki Forest virus membrane glycoproteins. Nature 288, 236–241.
7) Takkinen, K. (1986). Complete nucleotide sequence of the nonstructural protein genes of Semliki forest virus. Nucl. Acids Res. 14, 5667–5682.
8) de Groot, R. J., Hardy, W. R., Shirako, Y., and Strauss, J. H. (1990). Cleavage-site preferences of Sindbis virus polyproteins containing the non-structural proteinase. Evidence for temporal regulation of polyprotein processing in vivo. EMBO J. 9, 2631–2638.
9) Hahn, Y. S., Strauss, E. G., and Strauss, J. H. (1989b). Mapping of RNA-temperature-sensitive mutants of Sindbis virus: assignment of complementation groups A, B, and G to nonstructural proteins. J. Virol. 63, 3142–3150.
10) Mi, S., Durbin, R., Huang, H. V., Rice, C. M., and Stollar, V. (1989). Association of the Sindbis virus RNA methyltransferase activity with the nonstructural protein nsP1. Virology 170, 385–391.
11) Ding, M., and Schlesinger, M. J. (1989). Evidence that Sindbis virus nsP2 is an autoprotease which processes the virus non-structural polyprotein. Virology 171, 280–284.
12) Hardy, W. R., and Strauss, J. H. (1989). Processing the nonstructural polyproteins of Sindbis virus: nonstructural proteinase is in the C-terminal half of nsP2 and functions both in cis and in trans. J. Virol. 63, 4653–4664.
13) Li, G., La Starza, M. W., Hardy, W. R., Strauss, J. H., and Rice, C. M. (1990). Phosphorylation of Sindbis virus nsP3 in vivo and in vitro.
14) Peränen, J., Takkinen, K., Kalkkinen, N., and Kääriäinen, L. (1988). Semliki Forest virus-specific nonstructural protein nsP3 is a phosphoprotein. J. Gen. Virol. 69, 2165–2178.
15) Hahn, Y. S., Grakoui, A., Rice, C. M., Strauss, E. G., and Strauss, J. H. (1989a). Mapping of RNA-temperature-sensitive mutants of Sindbis virus: complementation group F mutants have lesions in nsP4.
16) Sawicki, D. L., Barkhimer, D. B. Sawicki, S. G., Rice, C. M., and Schlesinger, S. (1990). Temperature sensitive shut-off of alphavirus minus strand RNA synthesis maps to a nonstructural protein, nsP4. Virology 174, 43–52.
17) Grakoui, A., Levis, R., Raju, R., Huang, H. V., and Rice, C. M. (1989). A cis-acting mutation in the Sindbis virus junction region which affects subgenomic RNA synthesis. J. Virol. 63, 5216–5227.
18) Levis, R., Schlesinger, S., and Huang, H. V. (1990). Promoter for Sindbis virus RNA-dependent subgenomic RNA transcription. J. Virol. 64, 1726–1733.
19) Schlesinger, S. S., and Schlesinger, M. J. (1986). Formation and assembly of alphavirus glycoproteins. In The Togaviridae and Flaviviridae, Vol. Schlesinger, S. S., and Schlesinger, M. J., eds. (New York: Plenum Press), pp.121–148.
20) Hahn, C. S., and Strauss, J. H. (1990). Site-directed mutagenesis of the proposed catalytic amino acids of the Sindbis virus capsid protein autoprotease. J. Virol. 64, 3069–3073.
21) Melancon, P., and Garoff, H. (1987). Processing of the Semliki Forest virus structural polyprotein; Role of the capsid protease. J. Virol. 61, 1301–1309.
22) Bonatti, S., Migliaccio, G., Blobel, G., and Walter, P (1984). Role of the signal recognition particle in the membrane assembly of Sindbis viral glycoprotein. Eur. J. Biochem. 140, 499–502.
23) Garoff, H., Simons, K., and Dobberstein, B. (1978). Assembly of Semliki Forest virus membrane glycoproteins in the membrane of the endoplasmic reticulum in vitro. J. Mol. Biol. 124, 587–600.

24) Garoff, H., Huylebroeck, D., Robinson, A., Tillman, U., and Liljeström, P. (1990). The signal sequence of the p62 protein of Semliki Forest virus is involved in initiation but not in completing chain translocation. J. Cell Biol. 111, 867–876.

25) Melancon, P., and Garoff, H. (1986). Reinitiation of translocation in the Semliki Forest virus structural polyprotein: Identification of the signal for the E1 glycoprotein. EMBO J. 5, 1551–1560.

26) Lobigs, M., Zhao, H., and Garoff, H. (1990b). Function of Semliki Forest virus E3 peptide in virus assembly: Replacement of E3 with an artificial signal peptide abolishes spike heterodimerization and surface expression of E1. J. Virol. 64, 4346–4355.

27) de Curtis, I., and Simons, K. (1988). Dissection of Semliki Forest virus glycoprotein delivery from the trans-Golgi network to the cell surface in permeabilized BHK cells. Proc. Natl. Acad. Sci. USA, 85, 8052–8056.

28) Helenius, A., Kielian, M., Mellman, I., and Schmid, S. (1989). Entry of enveloped viruses into their host cells. In Cell Biology of Virus Entry, Replication, and Pathogenesis, Vol. 90, Compans, R. W., Helenius, A., and Oldstone, M. B. A., eds. (New York: Alan R. Liss, Inc.), pp. 145–161.

29) Lobigs, M., and Garoff, H. (1990). Fusion function of the Semliki Forest virus spike is activated by proteolytic cleavage of the envelope glycoprotein p62. J. Virol. 64, 1233–1240.

30) Lobigs, M., Wahlberg, J. M., and Garoff, H. (1990a). Spike protein oligomerization control of Semliki Forest virus fusion. J. Virol. 64, 5214–5218.

31) Wahlberg, J. M., Boere, W. A., and Garoff, H. (1989). The heterodimeric association between the membrane proteins of Semliki Forest virus changes its sensitivity to mildly acidic pH during virus maturation. J. Virol. 63, 4991–4997.

32) Ziemiecki, A., Garoff, H., and Simons, K. (1980). Formation of the Semliki Forest virus membrane glycoprotein complexes in the infected cell. J. Gen. Virol. 50, 111–123.

33) Fuller, S. D. (1987). The T=4 envelope of Sindbis virus is organized by interactions with a complementary T=3 capsid. Cell 48, 923–934.

34) Wengler, G. (1980). Effects of alphaviruses on host cell macromolecular synthesis. In The Togaviruses, Vol. Schlesinger, R. W., eds. (New York: Academic Press, Inc.), pp. 459–472.

35) Stollar, V. (1980). Defective interfering alphaviruses. In The Togaviruses, Vol. Schlesinger, R. W., eds. (New York: Academic Press), pp. 427–457.

36) Boere, W. A. M., Harmsen, T., Vinje, J., Benaissa-Trouw, B. J., Kraaijeveld, C. A., and Snippe, H. (1984). Identification of distinct antigenic determinants on Semliki Forest virus by using monoclonal antibodies with different antiviral activities. J. Virol. 52, 575–582.

37) Greiser-Wilke, I., Moennig, V., Kaaden, O.-R., and Figueiredo, L. T. M. (1989). Most alphaviruses share a conserved epitopic region on their nucleocapsid protein. J. Gen. Virol. 70, 743–748.

38) Kondor, K. C., Bravo, R., Fuller, S. D., Cutler, D., and Garoff, H. (1985). Exocytotic pathways exist to both the apical and the basolateral cell surface of the polarized epithelial cell MDCK. Cell 43, 297–306.

39) Sambrook, J., Fritsch, E. F., and Maniatis, T. (1989). Molecular Cloning. A Laboratory Manual. (Cold Spring Harbor: Cold spring Harbor Laboratory Press).

40) Benson, S. A. (1984). A rapid procedure for isolation of DNA fragments from agarose gels. Bio Techniques 2, 66–68.

41) Silhavy, T. J., Berman, M. L., and Enquist, L. W. (1984). Experiments with Gene Fusions. (New York: Cold Spring Harbor Laboratory Press).

42) Yanisch-Perron, C., Vieira, J., and Messing, J. (1985). Improved M13 phage cloning vectors and host strains: nucleotide sequences of the M13mp18 and pUC19 vectors. Gene 33, 103–119.

43) Chung, C. T., and Miller, R. T. (1988). A rapid and convenient method for the preparation and storage of competent bacterial cells. Nucl. Acids Res. 16, 3580.

44) Kunkel, T. A., Roberts, J. D., and Zakour, R. A. (1987). Rapid and efficient site-specific mutagenesis without phenotypic selection. Meth. Enzymol. 154, 367–382.

45) Su, T.-Z., and E1-Gewely, M. R. (1988). A multisite-directed mutagenesis using T7 DNA polymerase: application for reconstructing a mammalian gene. Gen 69, 81–89.

46) Krieg, P. A., and Melton, D. A. (1987). In vitro RNA synthesis with SP6 RNA polymerase. Meth. Enzymol. 155, 397–415.

47) Rice, C. M., Levis, R., Strauss, J. H., and Huang, H. V. (1987). Production of infectious RNA transcripts from Sindbis virus cDNA clones: Mapping of lethal mutations, rescue of a temperature-sensitive marker, and in vitro mutagenesis to generate defined mutants. J. Virol. 61, 3809–3819.

48) Cutler, D. F., and Garoff, H. (1986). Mutants of the membrane-binding region of Semliki Forest virus E2 protein. I. Cell surface transport and fusogenic activity. J. Cell Biol. 102, 889–901.

49) Chamberlain, J. P. (1979). Fluorographic detection of radioactivity in polyacrylamide gels with watersoluble fluor, sodium salicylate. Anal. Biochem. 98, 132–135.

50) Gubler, U., and Hoffman, B. J. (1983). A simple and very efficient method for generating cDNA libraries. Gene 25, 263–269.

51) Haymerle, H., Herz, J., Bressan, G. M., Frank, R., and Stanley, K. K. (1986). Efficient construction of cDNA libraries in plasmid expression vectors using an adaptor strategy. Nucl. Acids Res. 14, 8615–8124.

52) Davis, N. L., Willis, L. V., Smith, J. F., and Johnston, R. E. (1989). In vitro synthesis of infectious Venezuelan Equine Encephalitis virus RNA from a cDNA clone: Analysis of a viable deletion mutant. Virology 171, 189–204.

53) Niesters, H. G., and Strauss, J. H. (1990a). Defined mutations in the 5' nontranslated sequence of Sindbis virus RNA. J. Virol. 64, 4162–4168.

54) Niesters, H. G. M., and Strauss, J. H. (1990b). Mutagenesis of the conserved 51 nucleotide region of Sindbis virus. J. Virol. 64, 1639–1647.

55) Tsiang, M., Weiss, B. G., and Schlesinger, S. (1988). Effects of 5'-terminal modifications on the biological activity of defective interfering RNAs of Sindbis virus. J. Virol. 62, 47–53.

56) Kuhn, R. J., Hong, Z., and Strauss, J. H. (1990). Mutagenesis of the 3' nontranslated region of Sindbis virus RNA. J. Virol. 64, 1465–1476.

57) Levis, R., Weiss, B. G., Tsiang, M., Huang, H., and Schlesinger, S. (1986). Deletion mapping of Sindbis virus DI RNAs derived from cDNAs defines the sequences essential for replication and packaging. Cell 44, 137–145.

58) Kozak, M. (1989). The scanning model for translation: an update. J. Cell Biol. 108, 229–241.

59) Weiss, B., Nitschko, H., Ghattas, I., Wright, R., and Schlesinger, S. (1989). Evidence for specificity in the encapsidation of Sindbis virus RNAs. J. Virol. 63, 5310–5318.

60) Davis N. L., Pence D. F., Meyer W. J., Schmaljohn A. L. and Johston R. E. (1987). Alternative forms of a strain-specific neutralizing antigenic site on the Sindbis virus E2 glycoprotein. Virology 161:101–108.
61) Mendoza Q. P., Stanley J. and Griffin D. E. (1988). Monoclonal antibodies to the E1 and E2 glycoproteins of Sindbis virus: Definition of epitopes and efficiency of protection from fatal encephalitis. J. Gen. Virol. 70:3015–3022.
62) Vrati S., Fernon C. A., Dalgarno L. and Weir R. C. (1988). Location of a major antigenic site involved in Ross River virus neutralization. Virology 162:346–353.
63) Grosfeld H., Velan B., Leitner M. Cohen S., Lustig S., Lachmi B. and Shafferman A. (1989). Semliki Forest virus E2 envelope epitopes induce a nonneutralizing humoral response which protects mice against lethal challenge. J. Virol. 63:3416–3422.
64) Zerial, M., Melancon, P., Schneider, C., and Garoff, H. (1986). The transmembrane segment of the human transferrin receptor functions as a signal peptide. EMBO J. 5, 1543–1550.
65) Schneider, C., Owen, M. J., Banville, D., and Williams, J. G. (1984). Primary structure of human transferrin receptor deduced from the mRNA sequence. Nature 311, 675–678.
66) Ratner L., Haseltine W., Patarca R., Livak K. J., Starcich B., Josephs S. F., Doran E. R., Rafalki J. A., Whitehorn E. A., Baumeister K., Ivanoff L., Petteway S. R., Pearson M. L., Lautenberger J. A., Papas T. S., Ghrayeb J., Chang N. T., Gallo R. C. and Wong-Staal F. (1985). Complete nucleotide sequence of the AIDS virus, HTLVIII. Nature 313:277–284.
67) AIDS (1988). Sci. Am. 259. A single-topic issue on HIV biology.
68) Desrosiers R. C., Wyand M. S., Kodama T., Ringler D. J., Arthur L. O., Sehgal P. K., Letvin N. L., King N. W. and Daniel M. D. (1989). Vaccine protection against simian immunodeficiency virus infection.
69) Ginsberg H., Brown F., Lerner R. A. and Chanoch R. M. (1988). Vaccines 1988. New chemical and genetic approaches to vaccination, Cold Spring Harbor Laboratory, 396 pp.
70) Burke K. L., Dunn G., Ferguson M., Minor P. D. and Almond J. W. (1988). Antigen chimeras of poliovirus as potential new vaccines. Nature 332:81–82.
71) Colbere-Garapin F., Christodoulou C., Crainic R., Garapin A.-C. and Candrea A. (1988). Addition of a foreign oligopeptide to the major capsid protein of poliovirus. Proc. Natl. Acad. Sci. USA 85:8668–8672.
72) Evans D. J., McKeating J., Meredith J. M., Burke K. L., Katrak K., John A., Ferguson M., Minor P. D., Weiss R. A. and Almond J. W. (1989). An engineered poliovirus chimaera elicits broadly reactive HIV-1 neutralizing antibodies. Nature 339:385–388.

---

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 11517 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( v i ) ORIGINAL SOURCE:
        ( A ) ORGANISM: Semliki Forest Virus ( i x ) FEATURE:
        ( A ) NAME/KEY: -
        ( B ) LOCATION: 1..11517
        ( D ) OTHER INFORMATION: /label=genome
        / note="Semliki Forest Virus complete nucleotide sequence, presented as a cloned DNA sequence; see Figure 5."

( i x ) FEATURE:
        ( A ) NAME/KEY: CDS
        ( B ) LOCATION: 87..7379
        ( D ) OTHER INFORMATION: /product="SFV polyprotein"

( i x ) FEATURE:
        ( A ) NAME/KEY: CDS
        ( B ) LOCATION: 7421..11179
        ( D ) OTHER INFORMATION: /product="SFV polyprotein"

( x i ) SEQUENCE DESCRIPTION: SEQ ID NO:1:

```
GATGGCGGAT GTGTGACATA CACGACGCCA AAAGATTTTG TTCCAGCTCC TGCCACCTCC              60

GCTACGCGAG AGATTAACCA CCCACG ATG GCC GCC AAA GTG CAT GTT GAT ATT             113
                             Met Ala Ala Lys Val His Val Asp Ile
                              1               5

GAG GCT GAC AGC CCA TTC ATC AAG TCT TTG CAG AAG GCA TTT CCG TCG              161
Glu Ala Asp Ser Pro Phe Ile Lys Ser Leu Gln Lys Ala Phe Pro Ser
 10              15                  20                  25

TTC GAG GTG GAG TCA TTG CAG GTC ACA CCA AAT GAC CAT GCA AAT GCC              209
Phe Glu Val Glu Ser Leu Gln Val Thr Pro Asn Asp His Ala Asn Ala
                 30                  35                  40

AGA GCA TTT TCG CAC CTG GCT ACC AAA TTG ATC GAG CAG GAG ACT GAC              257
Arg Ala Phe Ser His Leu Ala Thr Lys Leu Ile Glu Gln Glu Thr Asp
             45                  50                  55

AAA GAC ACA CTC ATC TTG GAT ATC GGC AGT GCG CCT TCC AGG AGA ATG              305
Lys Asp Thr Leu Ile Leu Asp Ile Gly Ser Ala Pro Ser Arg Arg Met
         60                  65                  70

ATG TCT ACG CAC AAA TAC CAC TGC GTA TGC CCT ATG CGC AGC GCA GAA              353
Met Ser Thr His Lys Tyr His Cys Val Cys Pro Met Arg Ser Ala Glu
     75                  80                  85

GAC CCC GAA AGG CTC GAT AGC TAC GCA AAG AAA CTG GCA GCG GCC TCC              401
Asp Pro Glu Arg Leu Asp Ser Tyr Ala Lys Lys Leu Ala Ala Ala Ser
 90                  95                 100                 105

GGG AAG GTG CTG GAT AGA GAG ATC GCA GGA AAA ATC ACC GAC CTG CAG              449
Gly Lys Val Leu Asp Arg Glu Ile Ala Gly Lys Ile Thr Asp Leu Gln
                110                 115                 120

ACC GTC ATG GCT ACG CCA GAC GCT GAA TCT CCT ACC TTT TGC CTG CAT              497
Thr Val Met Ala Thr Pro Asp Ala Glu Ser Pro Thr Phe Cys Leu His
             125                 130                 135

ACA GAC GTC ACG TGT CGT ACG GCA GCC GAA GTG GCC GTA TAC CAG GAC              545
Thr Asp Val Thr Cys Arg Thr Ala Ala Glu Val Ala Val Tyr Gln Asp
         140                 145                 150

GTG TAT GCT GTA CAT GCA CCA ACA TCG CTG TAC CAT CAG GCG ATG AAA              593
Val Tyr Ala Val His Ala Pro Thr Ser Leu Tyr His Gln Ala Met Lys
     155                 160                 165

GGT GTC AGA ACG GCG TAT TGG ATT GGG TTT GAC ACC ACC CCG TTT ATG              641
Gly Val Arg Thr Ala Tyr Trp Ile Gly Phe Asp Thr Thr Pro Phe Met
170                 175                 180                 185

TTT GAC GCG CTA GCA GGC GCG TAT CCA ACC TAC GCC ACA AAC TGG GCC              689
Phe Asp Ala Leu Ala Gly Ala Tyr Pro Thr Tyr Ala Thr Asn Trp Ala
                190                 195                 200

GAC GAG CAG GTG TTA CAG GCC AGG AAC ATA GGA CTG TGT GCA GCA TCC              737
Asp Glu Gln Val Leu Gln Ala Arg Asn Ile Gly Leu Cys Ala Ala Ser
             205                 210                 215

TTG ACT GAG GGA AGA CTC GGC AAA CTG TCC ATT CTC CGC AAG AAG CAA              785
Leu Thr Glu Gly Arg Leu Gly Lys Leu Ser Ile Leu Arg Lys Lys Gln
         220                 225                 230

TTG AAA CCT TGC GAC ACA GTC ATG TTC TCG GTA GGA TCT ACA TTG TAC              833
Leu Lys Pro Cys Asp Thr Val Met Phe Ser Val Gly Ser Thr Leu Tyr
     235                 240                 245

ACT GAG AGC AGA AAG CTA CTG AGG AGC TGG CAC TTA CCC TCC GTA TTC              881
Thr Glu Ser Arg Lys Leu Leu Arg Ser Trp His Leu Pro Ser Val Phe
250                 255                 260                 265

CAC CTG AAA GGT AAA CAA TCC TTT ACC TGT AGG TGC GAT ACC ATC GTA              929
His Leu Lys Gly Lys Gln Ser Phe Thr Cys Arg Cys Asp Thr Ile Val
                270                 275                 280

TCA TGT GAA GGG TAC GTA GTT AAG AAA ATC ACT ATG TGC CCC GGC CTG              977
Ser Cys Glu Gly Tyr Val Val Lys Lys Ile Thr Met Cys Pro Gly Leu
             285                 290                 295

TAC GGT AAA ACG GTA GGG TAC GCC GTG ACG TAT CAC GCG GAG GGA TTC             1025
Tyr Gly Lys Thr Val Gly Tyr Ala Val Thr Tyr His Ala Glu Gly Phe
```

-continued

|     | 300 |     |     |     | 305 |     |     |     | 310 |     |     |     |     |     |      |
|-----|-----|-----|-----|-----|-----|-----|-----|-----|-----|-----|-----|-----|-----|-----|------|
| CTA | GTG | TGC | AAG | ACC | ACA | GAC | ACT | GTC | AAA | GGA | GAA | AGA | GTC | TCA | TTC | 1073 |
| Leu | Val | Cys | Lys | Thr | Thr | Asp | Thr | Val | Lys | Gly | Glu | Arg | Val | Ser | Phe |      |
|     | 315 |     |     |     | 320 |     |     |     | 325 |     |     |     |     |     |     |      |

| CCT | GTA | TGC | ACC | TAC | GTC | CCC | TCA | ACC | ATC | TGT | GAT | CAA | ATG | ACT | GGC | 1121 |
| Pro | Val | Cys | Thr | Tyr | Val | Pro | Ser | Thr | Ile | Cys | Asp | Gln | Met | Thr | Gly |      |
| 330 |     |     |     |     | 335 |     |     |     | 340 |     |     |     |     |     | 345 |      |

| ATA | CTA | GCG | ACC | GAC | GTC | ACA | CCG | GAG | GAC | GCA | CAG | AAG | TTG | TTA | GTG | 1169 |
| Ile | Leu | Ala | Thr | Asp | Val | Thr | Pro | Glu | Asp | Ala | Gln | Lys | Leu | Leu | Val |      |
|     |     |     |     | 350 |     |     |     |     | 355 |     |     |     |     | 360 |     |      |

| GGA | TTG | AAT | CAG | AGG | ATA | GTT | GTG | AAC | GGA | AGA | ACA | CAG | CGA | AAC | ACT | 1217 |
| Gly | Leu | Asn | Gln | Arg | Ile | Val | Val | Asn | Gly | Arg | Thr | Gln | Arg | Asn | Thr |      |
|     |     |     | 365 |     |     |     |     | 370 |     |     |     |     | 375 |     |     |      |

| AAC | ACG | ATG | AAG | AAC | TAT | CTG | CTT | CCG | ATT | GTG | GCC | GTC | GCA | TTT | AGC | 1265 |
| Asn | Thr | Met | Lys | Asn | Tyr | Leu | Leu | Pro | Ile | Val | Ala | Val | Ala | Phe | Ser |      |
|     |     | 380 |     |     |     |     | 385 |     |     |     |     | 390 |     |     |     |      |

| AAG | TGG | GCG | AGG | GAA | TAC | AAG | GCA | GAC | CTT | GAT | GAT | GAA | AAA | CCT | CTG | 1313 |
| Lys | Trp | Ala | Arg | Glu | Tyr | Lys | Ala | Asp | Leu | Asp | Asp | Glu | Lys | Pro | Leu |      |
|     | 395 |     |     |     |     | 400 |     |     |     |     | 405 |     |     |     |     |      |

| GGT | GTC | CGA | GAG | AGG | TCA | CTT | ACT | TGC | TGC | TGC | TTG | TGG | GCA | TTT | AAA | 1361 |
| Gly | Val | Arg | Glu | Arg | Ser | Leu | Thr | Cys | Cys | Cys | Leu | Trp | Ala | Phe | Lys |      |
| 410 |     |     |     |     | 415 |     |     |     |     | 420 |     |     |     |     | 425 |      |

| ACG | AGG | AAG | ATG | CAC | ACC | ATG | TAC | AAG | AAA | CCA | GAC | ACC | CAG | ACA | ATA | 1409 |
| Thr | Arg | Lys | Met | His | Thr | Met | Tyr | Lys | Lys | Pro | Asp | Thr | Gln | Thr | Ile |      |
|     |     |     |     | 430 |     |     |     |     | 435 |     |     |     |     | 440 |     |      |

| GTG | AAG | GTG | CCT | TCA | GAG | TTT | AAC | TCG | TTC | GTC | ATC | CCG | AGC | CTA | TGG | 1457 |
| Val | Lys | Val | Pro | Ser | Glu | Phe | Asn | Ser | Phe | Val | Ile | Pro | Ser | Leu | Trp |      |
|     |     |     | 445 |     |     |     |     | 450 |     |     |     |     | 455 |     |     |      |

| TCT | ACA | GGC | CTC | GCA | ATC | CCA | GTC | AGA | TCA | CGC | ATT | AAG | ATG | CTT | TTG | 1505 |
| Ser | Thr | Gly | Leu | Ala | Ile | Pro | Val | Arg | Ser | Arg | Ile | Lys | Met | Leu | Leu |      |
|     |     | 460 |     |     |     |     | 465 |     |     |     |     | 470 |     |     |     |      |

| GCC | AAG | AAG | ACC | AAG | CGA | GAG | TTA | ATA | CCT | GTT | CTC | GAC | GCG | TCG | TCA | 1553 |
| Ala | Lys | Lys | Thr | Lys | Arg | Glu | Leu | Ile | Pro | Val | Leu | Asp | Ala | Ser | Ser |      |
|     | 475 |     |     |     |     | 480 |     |     |     |     | 485 |     |     |     |     |      |

| GCC | AGG | GAT | GCT | GAA | CAA | GAG | GAG | AAG | GAG | AGG | TTG | GAG | GCC | GAG | CTG | 1601 |
| Ala | Arg | Asp | Ala | Glu | Gln | Glu | Glu | Lys | Glu | Arg | Leu | Glu | Ala | Glu | Leu |      |
| 490 |     |     |     |     | 495 |     |     |     |     | 500 |     |     |     |     | 505 |      |

| ACT | AGA | GAA | GCC | TTA | CCA | CCC | CTC | GTC | CCC | ATC | GCG | CCG | GCG | GAG | ACG | 1649 |
| Thr | Arg | Glu | Ala | Leu | Pro | Pro | Leu | Val | Pro | Ile | Ala | Pro | Ala | Glu | Thr |      |
|     |     |     |     | 510 |     |     |     |     | 515 |     |     |     |     | 520 |     |      |

| GGA | GTC | GTC | GAC | GTC | GAC | GTT | GAA | GAA | CTA | GAG | TAT | CAC | GCA | GGT | GCA | 1697 |
| Gly | Val | Val | Asp | Val | Asp | Val | Glu | Glu | Leu | Glu | Tyr | His | Ala | Gly | Ala |      |
|     |     |     | 525 |     |     |     |     | 530 |     |     |     |     | 535 |     |     |      |

| GGG | GTC | GTG | GAA | ACA | CCT | CGC | AGC | GCG | TTG | AAA | GTC | ACC | GCA | CAG | CCG | 1745 |
| Gly | Val | Val | Glu | Thr | Pro | Arg | Ser | Ala | Leu | Lys | Val | Thr | Ala | Gln | Pro |      |
|     |     | 540 |     |     |     |     | 545 |     |     |     |     | 550 |     |     |     |      |

| AAC | GAC | GTA | CTA | CTA | GGA | AAT | TAC | GTA | GTT | CTG | TCC | CCG | CAG | ACC | GTG | 1793 |
| Asn | Asp | Val | Leu | Leu | Gly | Asn | Tyr | Val | Val | Leu | Ser | Pro | Gln | Thr | Val |      |
|     | 555 |     |     |     |     | 560 |     |     |     |     | 565 |     |     |     |     |      |

| CTC | AAG | AGC | TCC | AAG | TTG | GCC | CCC | GTG | CAC | CCT | CTA | GCA | GAG | CAG | GTG | 1841 |
| Leu | Lys | Ser | Ser | Lys | Leu | Ala | Pro | Val | His | Pro | Leu | Ala | Glu | Gln | Val |      |
| 570 |     |     |     |     | 575 |     |     |     |     | 580 |     |     |     |     | 585 |      |

| AAA | ATA | ATA | ACA | CAT | AAC | GGG | AGG | GCC | GGC | GGT | TAC | CAG | GTC | GAC | GGA | 1889 |
| Lys | Ile | Ile | Thr | His | Asn | Gly | Arg | Ala | Gly | Gly | Tyr | Gln | Val | Asp | Gly |      |
|     |     |     |     | 590 |     |     |     |     | 595 |     |     |     |     | 600 |     |      |

| TAT | GAC | GGC | AGG | GTC | CTA | CTA | CCA | TGT | GGA | TCG | GCC | ATT | CCG | GTC | CCT | 1937 |
| Tyr | Asp | Gly | Arg | Val | Leu | Leu | Pro | Cys | Gly | Ser | Ala | Ile | Pro | Val | Pro |      |
|     |     |     | 605 |     |     |     |     | 610 |     |     |     |     | 615 |     |     |      |

| GAG | TTT | CAA | GCT | TTG | AGC | GAG | AGC | GCC | ACT | ATG | GTG | TAC | AAC | GAA | AGG | 1985 |
| Glu | Phe | Gln | Ala | Leu | Ser | Glu | Ser | Ala | Thr | Met | Val | Tyr | Asn | Glu | Arg |      |

|   |   |   |   |   | 620 |   |   |   |   | 625 |   |   |   |   | 630 |   |   |   |
|---|---|---|---|---|---|---|---|---|---|---|---|---|---|---|---|---|---|---|

| GAG | TTC | GTC | AAC | AGG | AAA | CTA | TAC | CAT | ATT | GCC | GTT | CAC | GGA | CCG | TCG | 2033 |
|-----|-----|-----|-----|-----|-----|-----|-----|-----|-----|-----|-----|-----|-----|-----|-----|------|
| Glu | Phe | Val | Asn | Arg | Lys | Leu | Tyr | His | Ile | Ala | Val | His | Gly | Pro | Ser |      |
|     | 635 |     |     |     |     | 640 |     |     |     |     |     | 645 |     |     |     |      |

| CTG | AAC | ACC | GAC | GAG | GAG | AAC | TAC | GAG | AAA | GTC | AGA | GCT | GAA | AGA | ACT | 2081 |
| Leu | Asn | Thr | Asp | Glu | Glu | Asn | Tyr | Glu | Lys | Val | Arg | Ala | Glu | Arg | Thr |      |
| 650 |     |     |     |     | 655 |     |     |     |     | 660 |     |     |     |     | 665 |      |

| GAC | GCC | GAG | TAC | GTG | TTC | GAC | GTA | GAT | AAA | AAA | TGC | TGC | GTC | AAG | AGA | 2129 |
| Asp | Ala | Glu | Tyr | Val | Phe | Asp | Val | Asp | Lys | Lys | Cys | Cys | Val | Lys | Arg |      |
|     |     |     |     | 670 |     |     |     |     | 675 |     |     |     |     | 680 |     |      |

| GAG | GAA | GCG | TCG | GGT | TTG | GTG | TTG | GTG | GGA | GAG | CTA | ACC | AAC | CCC | CCG | 2177 |
| Glu | Glu | Ala | Ser | Gly | Leu | Val | Leu | Val | Gly | Glu | Leu | Thr | Asn | Pro | Pro |      |
|     |     |     | 685 |     |     |     |     | 690 |     |     |     |     | 695 |     |     |      |

| TTC | CAT | GAA | TTC | GCC | TAC | GAA | GGG | CTG | AAG | ATC | AGG | CCG | TCG | GCA | CCA | 2225 |
| Phe | His | Glu | Phe | Ala | Tyr | Glu | Gly | Leu | Lys | Ile | Arg | Pro | Ser | Ala | Pro |      |
|     |     | 700 |     |     |     |     | 705 |     |     |     |     | 710 |     |     |     |      |

| TAT | AAG | ACT | ACA | GTA | GTA | GGA | GTC | TTT | GGG | GTT | CCG | GGA | TCA | GGC | AAG | 2273 |
| Tyr | Lys | Thr | Thr | Val | Val | Gly | Val | Phe | Gly | Val | Pro | Gly | Ser | Gly | Lys |      |
|     | 715 |     |     |     |     | 720 |     |     |     |     | 725 |     |     |     |     |      |

| TCT | GCT | ATT | ATT | AAG | AGC | CTC | GTG | ACC | AAA | CAC | GAT | CTG | GTC | ACC | AGC | 2321 |
| Ser | Ala | Ile | Ile | Lys | Ser | Leu | Val | Thr | Lys | His | Asp | Leu | Val | Thr | Ser |      |
| 730 |     |     |     |     | 735 |     |     |     |     | 740 |     |     |     |     | 745 |      |

| GGC | AAG | AAG | GAG | AAC | TGC | CAG | GAA | ATA | GTT | AAC | GAC | GTG | AAG | AAG | CAC | 2369 |
| Gly | Lys | Lys | Glu | Asn | Cys | Gln | Glu | Ile | Val | Asn | Asp | Val | Lys | Lys | His |      |
|     |     |     |     | 750 |     |     |     |     | 755 |     |     |     |     | 760 |     |      |

| CGC | GGG | AAG | GGG | ACA | AGT | AGG | GAA | AAC | AGT | GAC | TCC | ATC | CTG | CTA | AAC | 2417 |
| Arg | Gly | Lys | Gly | Thr | Ser | Arg | Glu | Asn | Ser | Asp | Ser | Ile | Leu | Leu | Asn |      |
|     |     |     | 765 |     |     |     |     | 770 |     |     |     |     | 775 |     |     |      |

| GGG | TGT | CGT | CGT | GCC | GTG | GAC | ATC | CTA | TAT | GTG | GAC | GAG | GCT | TTC | GCT | 2465 |
| Gly | Cys | Arg | Arg | Ala | Val | Asp | Ile | Leu | Tyr | Val | Asp | Glu | Ala | Phe | Ala |      |
|     |     | 780 |     |     |     |     | 785 |     |     |     |     | 790 |     |     |     |      |

| TGC | CAT | TCC | GGT | ACT | CTG | CTG | GCC | CTA | ATT | GCT | CTT | GTT | AAA | CCT | CGG | 2513 |
| Cys | His | Ser | Gly | Thr | Leu | Leu | Ala | Leu | Ile | Ala | Leu | Val | Lys | Pro | Arg |      |
| 795 |     |     |     |     | 800 |     |     |     |     | 805 |     |     |     |     |     |      |

| AGC | AAA | GTG | GTG | TTA | TGC | GGA | GAC | CCC | AAG | CAA | TGC | GGA | TTC | TTC | AAT | 2561 |
| Ser | Lys | Val | Val | Leu | Cys | Gly | Asp | Pro | Lys | Gln | Cys | Gly | Phe | Phe | Asn |      |
| 810 |     |     |     |     | 815 |     |     |     |     | 820 |     |     |     |     | 825 |      |

| ATG | ATG | CAG | CTT | AAG | GTG | AAC | TTC | AAC | CAC | AAC | ATC | TGC | ACT | GAA | GTA | 2609 |
| Met | Met | Gln | Leu | Lys | Val | Asn | Phe | Asn | His | Asn | Ile | Cys | Thr | Glu | Val |      |
|     |     |     |     | 830 |     |     |     |     | 835 |     |     |     |     | 840 |     |      |

| TGT | CAT | AAA | AGT | ATA | TCC | AGA | CGT | TGC | ACG | CGT | CCA | GTC | ACG | GCC | ATC | 2657 |
| Cys | His | Lys | Ser | Ile | Ser | Arg | Arg | Cys | Thr | Arg | Pro | Val | Thr | Ala | Ile |      |
|     |     |     | 845 |     |     |     |     | 850 |     |     |     |     | 855 |     |     |      |

| GTG | TCT | ACG | TTG | CAC | TAC | GGA | GGC | AAG | ATG | CGC | ACG | ACC | AAC | CCG | TGC | 2705 |
| Val | Ser | Thr | Leu | His | Tyr | Gly | Gly | Lys | Met | Arg | Thr | Thr | Asn | Pro | Cys |      |
|     |     | 860 |     |     |     |     | 865 |     |     |     |     | 870 |     |     |     |      |

| AAC | AAA | CCC | ATA | ATC | ATA | GAC | ACC | ACA | GGA | CAG | ACC | AAG | CCC | AAG | CCA | 2753 |
| Asn | Lys | Pro | Ile | Ile | Ile | Asp | Thr | Thr | Gly | Gln | Thr | Lys | Pro | Lys | Pro |      |
|     | 875 |     |     |     |     | 880 |     |     |     |     | 885 |     |     |     |     |      |

| GGA | GAC | ATC | GTG | TTA | ACA | TGC | TTC | CGA | GGC | TGG | GCA | AAG | CAG | CTG | CAG | 2801 |
| Gly | Asp | Ile | Val | Leu | Thr | Cys | Phe | Arg | Gly | Trp | Ala | Lys | Gln | Leu | Gln |      |
| 890 |     |     |     |     | 895 |     |     |     |     | 900 |     |     |     |     | 905 |      |

| TTG | GAC | TAC | CGT | GGA | CAC | GAA | GTC | ATG | ACA | GCA | GCA | GCA | TCT | CAG | GGC | 2849 |
| Leu | Asp | Tyr | Arg | Gly | His | Glu | Val | Met | Thr | Ala | Ala | Ala | Ser | Gln | Gly |      |
|     |     |     |     | 910 |     |     |     |     | 915 |     |     |     |     | 920 |     |      |

| CTC | ACC | CGC | AAA | GGG | GTA | TAC | GCC | GTA | AGG | CAG | AAG | GTG | AAT | GAA | AAT | 2897 |
| Leu | Thr | Arg | Lys | Gly | Val | Tyr | Ala | Val | Arg | Gln | Lys | Val | Asn | Glu | Asn |      |
|     |     |     | 925 |     |     |     |     | 930 |     |     |     |     | 935 |     |     |      |

| CCC | TTG | TAT | GCC | CCT | GCG | TCG | GAG | CAC | GTG | AAT | GTA | CTG | CTG | ACG | CGC | 2945 |
| Pro | Leu | Tyr | Ala | Pro | Ala | Ser | Glu | His | Val | Asn | Val | Leu | Leu | Thr | Arg |      |

-continued

| | | | | | | | | | | | | | | | | |
|---|---|---|---|---|---|---|---|---|---|---|---|---|---|---|---|---|
| | | 940 | | | | | 945 | | | | | 950 | | | | |
| ACT | GAG | GAT | AGG | CTG | GTG | TGG | AAA | ACG | CTG | GCC | GGC | GAT | CCC | TGG | ATT | 2993 |
| Thr | Glu | Asp | Arg | Leu | Val | Trp | Lys | Thr | Leu | Ala | Gly | Asp | Pro | Trp | Ile | |
| | | 955 | | | | | 960 | | | | | 965 | | | | |
| AAG | GTC | CTA | TCA | AAC | ATT | CCA | CAG | GGT | AAC | TTT | ACG | GCC | ACA | TTG | GAA | 3041 |
| Lys | Val | Leu | Ser | Asn | Ile | Pro | Gln | Gly | Asn | Phe | Thr | Ala | Thr | Leu | Glu | |
| 970 | | | | | 975 | | | | | 980 | | | | | 985 | |
| GAA | TGG | CAA | GAA | GAA | CAC | GAC | AAA | ATA | ATG | AAG | GTG | ATT | GAA | GGA | CCG | 3089 |
| Glu | Trp | Gln | Glu | Glu | His | Asp | Lys | Ile | Met | Lys | Val | Ile | Glu | Gly | Pro | |
| | | | | 990 | | | | | 995 | | | | | 1000 | | |
| GCT | GCG | CCT | GTG | GAC | GCG | TTC | CAG | AAC | AAA | GCG | AAC | GTG | TGT | TGG | GCG | 3137 |
| Ala | Ala | Pro | Val | Asp | Ala | Phe | Gln | Asn | Lys | Ala | Asn | Val | Cys | Trp | Ala | |
| | | | 1005 | | | | | 1010 | | | | | 1015 | | | |
| AAA | AGC | CTG | GTG | CCT | GTC | CTG | GAC | ACT | GCC | GGA | ATC | AGA | TTG | ACA | GCA | 3185 |
| Lys | Ser | Leu | Val | Pro | Val | Leu | Asp | Thr | Ala | Gly | Ile | Arg | Leu | Thr | Ala | |
| | | | 1020 | | | | | 1025 | | | | | 1030 | | | |
| GAG | GAG | TGG | AGC | ACC | ATA | ATT | ACA | GCA | TTT | AAG | GAG | GAC | AGA | GCT | TAC | 3233 |
| Glu | Glu | Trp | Ser | Thr | Ile | Ile | Thr | Ala | Phe | Lys | Glu | Asp | Arg | Ala | Tyr | |
| | | | 1035 | | | | | 1040 | | | | | 1045 | | | |
| TCT | CCA | GTG | GTG | GCC | TTG | AAT | GAA | ATT | TGC | ACC | AAG | TAC | TAT | GGA | GTT | 3281 |
| Ser | Pro | Val | Val | Ala | Leu | Asn | Glu | Ile | Cys | Thr | Lys | Tyr | Tyr | Gly | Val | |
| 1050 | | | | | 1055 | | | | | 1060 | | | | | 1065 | |
| GAC | CTG | GAC | AGT | GGC | CTG | TTT | TCT | GCC | CCG | AAG | GTG | TCC | CTG | TAT | TAC | 3329 |
| Asp | Leu | Asp | Ser | Gly | Leu | Phe | Ser | Ala | Pro | Lys | Val | Ser | Leu | Tyr | Tyr | |
| | | | | 1070 | | | | | 1075 | | | | | 1080 | | |
| GAG | AAC | AAC | CAC | TGG | GAT | AAC | AGA | CCT | GGT | GGA | AGG | ATG | TAT | GGA | TTC | 3377 |
| Glu | Asn | Asn | His | Trp | Asp | Asn | Arg | Pro | Gly | Gly | Arg | Met | Tyr | Gly | Phe | |
| | | | | 1085 | | | | | 1090 | | | | | 1095 | | |
| AAT | GCC | GCA | ACA | GCT | GCC | AGG | CTG | GAA | GCT | AGA | CAT | ACC | TTC | CTG | AAG | 3425 |
| Asn | Ala | Ala | Thr | Ala | Ala | Arg | Leu | Glu | Ala | Arg | His | Thr | Phe | Leu | Lys | |
| | | | 1100 | | | | | 1105 | | | | | 1110 | | | |
| GGG | CAG | TGG | CAT | ACG | GGC | AAG | CAG | GCA | GTT | ATC | GCA | GAA | AGA | AAA | ATC | 3473 |
| Gly | Gln | Trp | His | Thr | Gly | Lys | Gln | Ala | Val | Ile | Ala | Glu | Arg | Lys | Ile | |
| | | | 1115 | | | | | 1120 | | | | | 1125 | | | |
| CAA | CCG | CTT | TCT | GTG | CTG | GAC | AAT | GTA | ATT | CCT | ATC | AAC | CGC | AGG | CTG | 3521 |
| Gln | Pro | Leu | Ser | Val | Leu | Asp | Asn | Val | Ile | Pro | Ile | Asn | Arg | Arg | Leu | |
| 1130 | | | | | 1135 | | | | | 1140 | | | | | 1145 | |
| CCG | CAC | GCC | CTG | GTG | GCT | GAG | TAC | AAG | ACG | GTT | AAA | GGC | AGT | AGG | GTT | 3569 |
| Pro | His | Ala | Leu | Val | Ala | Glu | Tyr | Lys | Thr | Val | Lys | Gly | Ser | Arg | Val | |
| | | | | 1150 | | | | | 1155 | | | | | 1160 | | |
| GAG | TGG | CTG | GTC | AAT | AAA | GTA | AGA | GGG | TAC | CAC | GTC | CTG | CTG | GTG | AGT | 3617 |
| Glu | Trp | Leu | Val | Asn | Lys | Val | Arg | Gly | Tyr | His | Val | Leu | Leu | Val | Ser | |
| | | | | 1165 | | | | | 1170 | | | | | 1175 | | |
| GAG | TAC | AAC | CTG | GCT | TTG | CCT | CGA | CGC | AGG | GTC | ACT | TGG | TTG | TCA | CCG | 3665 |
| Glu | Tyr | Asn | Leu | Ala | Leu | Pro | Arg | Arg | Arg | Val | Thr | Trp | Leu | Ser | Pro | |
| | | | 1180 | | | | | 1185 | | | | | 1190 | | | |
| CTG | AAT | GTC | ACA | GGC | GCC | GAT | AGG | TGC | TAC | GAC | CTA | AGT | TTA | GGA | CTG | 3713 |
| Leu | Asn | Val | Thr | Gly | Ala | Asp | Arg | Cys | Tyr | Asp | Leu | Ser | Leu | Gly | Leu | |
| | | | 1195 | | | | | 1200 | | | | | 1205 | | | |
| CCG | GCT | GAC | GCC | GGC | AGG | TTC | GAC | TTG | GTC | TTT | GTG | AAC | ATT | CAC | ACG | 3761 |
| Pro | Ala | Asp | Ala | Gly | Arg | Phe | Asp | Leu | Val | Phe | Val | Asn | Ile | His | Thr | |
| 1210 | | | | | 1215 | | | | | 1220 | | | | | 1225 | |
| GAA | TTC | AGA | ATC | CAC | CAC | TAC | CAG | CAG | TGT | GTC | GAC | CAC | GCC | ATG | AAG | 3809 |
| Glu | Phe | Arg | Ile | His | His | Tyr | Gln | Gln | Cys | Val | Asp | His | Ala | Met | Lys | |
| | | | 1230 | | | | | 1235 | | | | | 1240 | | | |
| CTG | CAG | ATG | CTT | GGG | GGA | GAT | GCG | CTA | CGA | CTG | CTA | AAA | CCC | GGC | GGC | 3857 |
| Leu | Gln | Met | Leu | Gly | Gly | Asp | Ala | Leu | Arg | Leu | Leu | Lys | Pro | Gly | Gly | |
| | | | 1245 | | | | | 1250 | | | | | 1255 | | | |
| ATC | TTG | ATG | AGA | GCT | TAC | GGA | TAC | GCC | GAT | AAA | ATC | AGC | GAA | GCC | GTT | 3905 |
| Ile | Leu | Met | Arg | Ala | Tyr | Gly | Tyr | Ala | Asp | Lys | Ile | Ser | Glu | Ala | Val | |

```
                    1260                              1265                              1270
GTT  TCC  TCC  TTA  AGC  AGA  AAG  TTC  TCG  TCT  GCA  AGA  GTG  TTG  CGC  CCG         3953
Val  Ser  Ser  Leu  Ser  Arg  Lys  Phe  Ser  Ser  Ala  Arg  Val  Leu  Arg  Pro
     1275                          1280                          1285

GAT  TGT  GTC  ACC  AGC  AAT  ACA  GAA  GTG  TTC  TTG  CTG  TTC  TCC  AAC  TTT         4001
Asp  Cys  Val  Thr  Ser  Asn  Thr  Glu  Val  Phe  Leu  Leu  Phe  Ser  Asn  Phe
1290                          1295                          1300                 1305

GAC  AAC  GGA  AAG  AGA  CCC  TCT  ACG  CTA  CAC  CAG  ATG  AAT  ACC  AAG  CTG         4049
Asp  Asn  Gly  Lys  Arg  Pro  Ser  Thr  Leu  His  Gln  Met  Asn  Thr  Lys  Leu
                         1310                     1315                     1320

AGT  GCC  GTG  TAT  GCC  GGA  GAA  GCC  ATG  CAC  ACG  GCC  GGG  TGT  GCA  CCA         4097
Ser  Ala  Val  Tyr  Ala  Gly  Glu  Ala  Met  His  Thr  Ala  Gly  Cys  Ala  Pro
               1325                     1330                     1335

TCC  TAC  AGA  GTT  AAG  AGA  GCA  GAC  ATA  GCC  ACG  TGC  ACA  GAA  GCG  GCT         4145
Ser  Tyr  Arg  Val  Lys  Arg  Ala  Asp  Ile  Ala  Thr  Cys  Thr  Glu  Ala  Ala
          1340                     1345                     1350

GTG  GTT  AAC  GCA  GCT  AAC  GCC  CGT  GGA  ACT  GTA  GGG  GAT  GGC  GTA  TGC         4193
Val  Val  Asn  Ala  Ala  Asn  Ala  Arg  Gly  Thr  Val  Gly  Asp  Gly  Val  Cys
     1355                     1360                     1365

AGG  GCC  GTG  GCG  AAG  AAA  TGG  CCG  TCA  GCC  TTT  AAG  GGA  GCA  GCA  ACA         4241
Arg  Ala  Val  Ala  Lys  Lys  Trp  Pro  Ser  Ala  Phe  Lys  Gly  Ala  Ala  Thr
1370                     1375                     1380                     1385

CCA  GTG  GGC  ACA  ATT  AAA  ACA  GTC  ATG  TGC  GGC  TCG  TAC  CCC  GTC  ATC         4289
Pro  Val  Gly  Thr  Ile  Lys  Thr  Val  Met  Cys  Gly  Ser  Tyr  Pro  Val  Ile
                    1390                     1395                     1400

CAC  GCT  GTA  GCG  CCT  AAT  TTC  TCT  GCC  ACG  ACT  GAA  GCG  GAA  GGG  GAC         4337
His  Ala  Val  Ala  Pro  Asn  Phe  Ser  Ala  Thr  Thr  Glu  Ala  Glu  Gly  Asp
               1405                     1410                     1415

CGC  GAA  TTG  GCC  GCT  GTC  TAC  CGG  GCA  GTG  GCC  GCC  GAA  GTA  AAC  AGA         4385
Arg  Glu  Leu  Ala  Ala  Val  Tyr  Arg  Ala  Val  Ala  Ala  Glu  Val  Asn  Arg
          1420                     1425                     1430

CTG  TCA  CTG  AGC  AGC  GTA  GCC  ATC  CCG  CTG  CTG  TCC  ACA  GGA  GTG  TTC         4433
Leu  Ser  Leu  Ser  Ser  Val  Ala  Ile  Pro  Leu  Leu  Ser  Thr  Gly  Val  Phe
     1435                     1440                     1445

AGC  GGC  GGA  AGA  GAT  AGG  CTG  CAG  CAA  TCC  CTC  AAC  CAT  CTA  TTC  ACA         4481
Ser  Gly  Gly  Arg  Asp  Arg  Leu  Gln  Gln  Ser  Leu  Asn  His  Leu  Phe  Thr
1450                     1455                     1460                     1465

GCA  ATG  GAC  GCC  ACG  GAC  GCT  GAC  GTG  ACC  ATC  TAC  TGC  AGA  GAC  AAA         4529
Ala  Met  Asp  Ala  Thr  Asp  Ala  Asp  Val  Thr  Ile  Tyr  Cys  Arg  Asp  Lys
                    1470                     1475                     1480

AGT  TGG  GAG  AAG  AAA  ATC  CAG  GAA  GCC  ATT  GAC  ATG  AGG  ACG  GCT  GTG         4577
Ser  Trp  Glu  Lys  Lys  Ile  Gln  Glu  Ala  Ile  Asp  Met  Arg  Thr  Ala  Val
               1485                     1490                     1495

GAG  TTG  CTC  AAT  GAT  GAC  GTG  GAG  CTG  ACC  ACA  GAC  TTG  GTG  AGA  GTG         4625
Glu  Leu  Leu  Asn  Asp  Asp  Val  Glu  Leu  Thr  Thr  Asp  Leu  Val  Arg  Val
          1500                     1505                     1510

CAC  CCG  GAC  AGC  AGC  CTG  GTG  GGT  CGT  AAG  GGC  TAC  AGT  ACC  ACT  GAC         4673
His  Pro  Asp  Ser  Ser  Leu  Val  Gly  Arg  Lys  Gly  Tyr  Ser  Thr  Thr  Asp
     1515                     1520                     1525

GGG  TCG  CTG  TAC  TCG  TAC  TTT  GAA  GGT  ACG  AAA  TTC  AAC  CAG  GCT  GCT         4721
Gly  Ser  Leu  Tyr  Ser  Tyr  Phe  Glu  Gly  Thr  Lys  Phe  Asn  Gln  Ala  Ala
1530                     1535                     1540                     1545

ATT  GAT  ATG  GCA  GAG  ATA  CTG  ACG  TTG  TGG  CCC  AGA  CTG  CAA  GAG  GCA         4769
Ile  Asp  Met  Ala  Glu  Ile  Leu  Thr  Leu  Trp  Pro  Arg  Leu  Gln  Glu  Ala
                    1550                     1555                     1560

AAC  GAA  CAG  ATA  TGC  CTA  TAC  GCG  CTG  GGC  GAA  ACA  ATG  GAC  AAC  ATC         4817
Asn  Glu  Gln  Ile  Cys  Leu  Tyr  Ala  Leu  Gly  Glu  Thr  Met  Asp  Asn  Ile
               1565                     1570                     1575

AGA  TCC  AAA  TGT  CCG  GTG  AAC  GAT  TCC  GAT  TCA  TCA  ACA  CCT  CCC  AGG         4865
Arg  Ser  Lys  Cys  Pro  Val  Asn  Asp  Ser  Asp  Ser  Ser  Thr  Pro  Pro  Arg
```

|      | 1580 |      |      |      | 1585 |      |      |      |      | 1590 |      |      |      |      |
|------|------|------|------|------|------|------|------|------|------|------|------|------|------|------|

```
ACA  GTG  CCC  TGC  CTG  TGC  CGC  TAC  GCA  ATG  ACA  GCA  GAA  CGG  ATC  GCC    4913
Thr  Val  Pro  Cys  Leu  Cys  Arg  Tyr  Ala  Met  Thr  Ala  Glu  Arg  Ile  Ala
     1595                     1600                    1605

CGC  CTT  AGG  TCA  CAC  CAA  GTT  AAA  AGC  ATG  GTG  GTT  TGC  TCA  TCT  TTT    4961
Arg  Leu  Arg  Ser  His  Gln  Val  Lys  Ser  Met  Val  Val  Cys  Ser  Ser  Phe
1610                    1615                    1620                    1625

CCC  CTC  CCG  AAA  TAC  CAT  GTA  GAT  GGG  GTG  CAG  AAG  GTA  AAG  TGC  GAG    5009
Pro  Leu  Pro  Lys  Tyr  His  Val  Asp  Gly  Val  Gln  Lys  Val  Lys  Cys  Glu
                         1630                    1635                    1640

AAG  GTT  CTC  CTG  TTC  GAC  CCG  ACG  GTA  CCT  TCA  GTG  GTT  AGT  CCG  CGG    5057
Lys  Val  Leu  Leu  Phe  Asp  Pro  Thr  Val  Pro  Ser  Val  Val  Ser  Pro  Arg
               1645                    1650                    1655

AAG  TAT  GCC  GCA  TCT  ACG  ACG  GAC  CAC  TCA  GAT  CGG  TCG  TTA  CGA  GGG    5105
Lys  Tyr  Ala  Ala  Ser  Thr  Thr  Asp  His  Ser  Asp  Arg  Ser  Leu  Arg  Gly
          1660                    1665                    1670

TTT  GAC  TTG  GAC  TGG  ACC  ACC  GAC  TCG  TCT  TCC  ACT  GCC  AGC  GAT  ACC    5153
Phe  Asp  Leu  Asp  Trp  Thr  Thr  Asp  Ser  Ser  Ser  Thr  Ala  Ser  Asp  Thr
1675                    1680                    1685

ATG  TCG  CTA  CCC  AGT  TTG  CAG  TCG  TGT  GAC  ATC  GAC  TCG  ATC  TAC  GAG    5201
Met  Ser  Leu  Pro  Ser  Leu  Gln  Ser  Cys  Asp  Ile  Asp  Ser  Ile  Tyr  Glu
1690                    1695                    1700                    1705

CCA  ATG  GCT  CCC  ATA  GTA  GTG  ACG  GCT  GAC  GTA  CAC  CCT  GAA  CCC  GCA    5249
Pro  Met  Ala  Pro  Ile  Val  Val  Thr  Ala  Asp  Val  His  Pro  Glu  Pro  Ala
                         1710                    1715                    1720

GGC  ATC  GCG  GAC  CTG  GCG  GCA  GAT  GTG  CAC  CCT  GAA  CCC  GCA  GAC  CAT    5297
Gly  Ile  Ala  Asp  Leu  Ala  Ala  Asp  Val  His  Pro  Glu  Pro  Ala  Asp  His
          1725                    1730                    1735

GTG  GAC  CTC  GAG  AAC  CCG  ATT  CCT  CCA  CCG  CGC  CCG  AAG  AGA  GCT  GCA    5345
Val  Asp  Leu  Glu  Asn  Pro  Ile  Pro  Pro  Pro  Arg  Pro  Lys  Arg  Ala  Ala
               1740                    1745                    1750

TAC  CTT  GCC  TCC  CGC  GCG  GCG  GAG  CGA  CCG  GTG  CCG  GCG  CCG  AGA  AAG    5393
Tyr  Leu  Ala  Ser  Arg  Ala  Ala  Glu  Arg  Pro  Val  Pro  Ala  Pro  Arg  Lys
     1755                    1760                    1765

CCG  ACG  CCT  GCC  CCA  AGG  ACT  GCG  TTT  AGG  AAC  AAG  CTG  CCT  TTG  ACG    5441
Pro  Thr  Pro  Ala  Pro  Arg  Thr  Ala  Phe  Arg  Asn  Lys  Leu  Pro  Leu  Thr
1770                    1775                    1780                    1785

TTC  GGC  GAC  TTT  GAC  GAG  CAC  GAG  GTC  GAT  GCG  TTG  GCC  TCC  GGG  ATT    5489
Phe  Gly  Asp  Phe  Asp  Glu  His  Glu  Val  Asp  Ala  Leu  Ala  Ser  Gly  Ile
                         1790                    1795                    1800

ACT  TTC  GGA  GAC  TTC  GAC  GAC  GTC  CTG  CGA  CTA  GGC  CGC  GCG  GGT  GCA    5537
Thr  Phe  Gly  Asp  Phe  Asp  Asp  Val  Leu  Arg  Leu  Gly  Arg  Ala  Gly  Ala
          1805                    1810                    1815

TAT  ATT  TTC  TCC  TCG  GAC  ACT  GGC  AGC  GGA  CAT  TTA  CAA  CAA  AAA  TCC    5585
Tyr  Ile  Phe  Ser  Ser  Asp  Thr  Gly  Ser  Gly  His  Leu  Gln  Gln  Lys  Ser
               1820                    1825                    1830

GTT  AGG  CAG  CAC  AAT  CTC  CAG  TGC  GCA  CAA  CTG  GAT  GCG  GTC  CAG  GAG    5633
Val  Arg  Gln  His  Asn  Leu  Gln  Cys  Ala  Gln  Leu  Asp  Ala  Val  Gln  Glu
1835                    1840                    1845

GAG  AAA  ATG  TAC  CCG  CCA  AAA  TTG  GAT  ACT  GAG  AGG  GAG  AAG  CTG  TTG    5681
Glu  Lys  Met  Tyr  Pro  Pro  Lys  Leu  Asp  Thr  Glu  Arg  Glu  Lys  Leu  Leu
1850                    1855                    1860                    1865

CTG  CTG  AAA  ATG  CAG  ATG  CAC  CCA  TCG  GAG  GCT  AAT  AAG  AGT  CGA  TAC    5729
Leu  Leu  Lys  Met  Gln  Met  His  Pro  Ser  Glu  Ala  Asn  Lys  Ser  Arg  Tyr
                         1870                    1875                    1880

CAG  TCT  CGC  AAA  GTG  GAG  AAC  ATG  AAA  GCC  ACG  GTG  GTG  GAC  AGG  CTC    5777
Gln  Ser  Arg  Lys  Val  Glu  Asn  Met  Lys  Ala  Thr  Val  Val  Asp  Arg  Leu
          1885                    1890                    1895

ACA  TCG  GGG  GCC  AGA  TTG  TAC  ACG  GGA  GCG  GAC  GTA  GGC  CGC  ATA  CCA    5825
Thr  Ser  Gly  Ala  Arg  Leu  Tyr  Thr  Gly  Ala  Asp  Val  Gly  Arg  Ile  Pro
```

```
               1900                    1905                     1910
ACA  TAC  GCG  GTT  CGG  TAC  CCC  CGC  CCC  GTG  TAC  TCC  CCT  ACC  GTG  ATC        5873
Thr  Tyr  Ala  Val  Arg  Tyr  Pro  Arg  Pro  Val  Tyr  Ser  Pro  Thr  Val  Ile
1915                     1920                    1925

GAA  AGA  TTC  TCA  AGC  CCC  GAT  GTA  GCA  ATC  GCA  GCG  TGC  AAC  GAA  TAC        5921
Glu  Arg  Phe  Ser  Ser  Pro  Asp  Val  Ala  Ile  Ala  Ala  Cys  Asn  Glu  Tyr
1930                     1935                    1940                     1945

CTA  TCC  AGA  AAT  TAC  CCA  ACA  GTG  GCG  TCG  TAC  CAG  ATA  ACA  GAT  GAA        5969
Leu  Ser  Arg  Asn  Tyr  Pro  Thr  Val  Ala  Ser  Tyr  Gln  Ile  Thr  Asp  Glu
                    1950                    1955                    1960

TAC  GAC  GCA  TAC  TTG  GAC  ATG  GTT  GAC  GGG  TCG  GAT  AGT  TGC  TTG  GAC        6017
Tyr  Asp  Ala  Tyr  Leu  Asp  Met  Val  Asp  Gly  Ser  Asp  Ser  Cys  Leu  Asp
               1965                    1970                    1975

AGA  GCG  ACA  TTC  TGC  CCG  GCG  AAG  CTC  CGG  TGC  TAC  CCG  AAA  CAT  CAT        6065
Arg  Ala  Thr  Phe  Cys  Pro  Ala  Lys  Leu  Arg  Cys  Tyr  Pro  Lys  His  His
1980                     1985                    1990

GCG  TAC  CAC  CAG  CCG  ACT  GTA  CGC  AGT  GCC  GTC  CCG  TCA  CCC  TTT  CAG        6113
Ala  Tyr  His  Gln  Pro  Thr  Val  Arg  Ser  Ala  Val  Pro  Ser  Pro  Phe  Gln
1995                     2000                    2005

AAC  ACA  CTA  CAG  AAC  GTG  CTA  GCG  GCC  GCC  ACC  AAG  AGA  AAC  TGC  AAC        6161
Asn  Thr  Leu  Gln  Asn  Val  Leu  Ala  Ala  Ala  Thr  Lys  Arg  Asn  Cys  Asn
2010                     2015                    2020                     2025

GTC  ACG  CAA  ATG  CGA  GAA  CTA  CCC  ACC  ATG  GAC  TCG  GCA  GTG  TTC  AAC        6209
Val  Thr  Gln  Met  Arg  Glu  Leu  Pro  Thr  Met  Asp  Ser  Ala  Val  Phe  Asn
                    2030                    2035                    2040

GTG  GAG  TGC  TTC  AAG  CGC  TAT  GCC  TGC  TCC  GGA  GAA  TAT  TGG  GAA  GAA        6257
Val  Glu  Cys  Phe  Lys  Arg  Tyr  Ala  Cys  Ser  Gly  Glu  Tyr  Trp  Glu  Glu
               2045                    2050                    2055

TAT  GCT  AAA  CAA  CCT  ATC  CGG  ATA  ACC  ACT  GAG  AAC  ATC  ACT  ACC  TAT        6305
Tyr  Ala  Lys  Gln  Pro  Ile  Arg  Ile  Thr  Thr  Glu  Asn  Ile  Thr  Thr  Tyr
2060                     2065                    2070

GTG  ACC  AAA  TTG  AAA  GGC  CCG  AAA  GCT  GCT  GCC  TTG  TTC  GCT  AAG  ACC        6353
Val  Thr  Lys  Leu  Lys  Gly  Pro  Lys  Ala  Ala  Ala  Leu  Phe  Ala  Lys  Thr
2075                     2080                    2085

CAC  AAC  TTG  GTT  CCG  CTG  CAG  GAG  GTT  CCC  ATG  GAC  AGA  TTC  ACG  GTC        6401
His  Asn  Leu  Val  Pro  Leu  Gln  Glu  Val  Pro  Met  Asp  Arg  Phe  Thr  Val
2090                     2095                    2100                     2105

GAC  ATG  AAA  CGA  GAT  GTC  AAA  GTC  ACT  CCA  GGG  ACG  AAA  CAC  ACA  GAG        6449
Asp  Met  Lys  Arg  Asp  Val  Lys  Val  Thr  Pro  Gly  Thr  Lys  His  Thr  Glu
                    2110                    2115                    2120

GAA  AGA  CCC  AAA  GTC  CAG  GTA  ATT  CAA  GCA  GCG  GAG  CCA  TTG  GCG  ACC        6497
Glu  Arg  Pro  Lys  Val  Gln  Val  Ile  Gln  Ala  Ala  Glu  Pro  Leu  Ala  Thr
               2125                    2130                    2135

GCT  TAC  CTG  TGC  GGC  ATC  CAC  AGG  GAA  TTA  GTA  AGG  AGA  CTA  AAT  GCT        6545
Ala  Tyr  Leu  Cys  Gly  Ile  His  Arg  Glu  Leu  Val  Arg  Arg  Leu  Asn  Ala
               2140                    2145                    2150

GTG  TTA  CGC  CCT  AAC  GTG  CAC  ACA  TTG  TTT  GAT  ATG  TCG  GCC  GAA  GAC        6593
Val  Leu  Arg  Pro  Asn  Val  His  Thr  Leu  Phe  Asp  Met  Ser  Ala  Glu  Asp
               2155                    2160                    2165

TTT  GAC  GCG  ATC  ATC  GCC  TCT  CAC  TTC  CAC  CCA  GGA  GAC  CCG  GTT  CTA        6641
Phe  Asp  Ala  Ile  Ile  Ala  Ser  His  Phe  His  Pro  Gly  Asp  Pro  Val  Leu
2170                     2175                    2180                     2185

GAG  ACG  GAC  ATT  GCA  TCA  TTC  GAC  AAA  AGC  CAG  GAC  GAC  TCC  TTG  GCT        6689
Glu  Thr  Asp  Ile  Ala  Ser  Phe  Asp  Lys  Ser  Gln  Asp  Asp  Ser  Leu  Ala
                    2190                    2195                    2200

CTT  ACA  GGT  TTA  ATG  ATC  CTC  GAA  GAT  CTA  GGG  GTG  GAT  CAG  TAC  CTG        6737
Leu  Thr  Gly  Leu  Met  Ile  Leu  Glu  Asp  Leu  Gly  Val  Asp  Gln  Tyr  Leu
               2205                    2210                    2215

CTG  GAC  TTG  ATC  GAG  GCA  GCC  TTT  GGG  GAA  ATA  TCC  AGC  TGT  CAC  CTA        6785
Leu  Asp  Leu  Ile  Glu  Ala  Ala  Phe  Gly  Glu  Ile  Ser  Ser  Cys  His  Leu
```

|  |  |  |  |  |  |  |  |  |  |  |  |  |  |  |  |
|---|---|---|---|---|---|---|---|---|---|---|---|---|---|---|---|
| | | 2220 | | | | | 2225 | | | | | 2230 | | | |

```
CCA  ACT  GGC  ACG  CGC  TTC  AAG  TTC  GGA  GCT  ATG  ATG  AAA  TCG  GGC  ATG         6833
Pro  Thr  Gly  Thr  Arg  Phe  Lys  Phe  Gly  Ala  Met  Met  Lys  Ser  Gly  Met
     2235                2240                     2245

TTT  CTG  ACT  TTG  TTT  ATT  AAC  ACT  GTT  TTG  AAC  ATC  ACC  ATA  GCA  AGC         6881
Phe  Leu  Thr  Leu  Phe  Ile  Asn  Thr  Val  Leu  Asn  Ile  Thr  Ile  Ala  Ser
2250                2255                     2260                     2265

AGG  GTA  CTG  GAG  CAG  AGA  CTC  ACT  GAC  TCC  GCC  TGT  GCG  GCC  TTC  ATC         6929
Arg  Val  Leu  Glu  Gln  Arg  Leu  Thr  Asp  Ser  Ala  Cys  Ala  Ala  Phe  Ile
               2270                     2275                     2280

GGC  GAC  GAC  AAC  ATC  GTT  CAC  GGA  GTG  ATC  TCC  GAC  AAG  CTG  ATG  GCG         6977
Gly  Asp  Asp  Asn  Ile  Val  His  Gly  Val  Ile  Ser  Asp  Lys  Leu  Met  Ala
          2285                     2290                     2295

GAG  AGG  TGC  GCG  TCG  TGG  GTC  AAC  ATG  GAG  GTG  AAG  ATC  ATT  GAC  GCT         7025
Glu  Arg  Cys  Ala  Ser  Trp  Val  Asn  Met  Glu  Val  Lys  Ile  Ile  Asp  Ala
     2300                     2305                     2310

GTC  ATG  GGC  GAA  AAA  CCC  CCA  TAT  TTT  TGT  GGG  GGA  TTC  ATA  GTT  TTT         7073
Val  Met  Gly  Glu  Lys  Pro  Pro  Tyr  Phe  Cys  Gly  Gly  Phe  Ile  Val  Phe
2315                     2320                     2325

GAC  AGC  GTC  ACA  CAG  ACC  GCC  TGC  CGT  GTT  TCA  GAC  CCA  CTT  AAG  CGC         7121
Asp  Ser  Val  Thr  Gln  Thr  Ala  Cys  Arg  Val  Ser  Asp  Pro  Leu  Lys  Arg
2330                2335                     2340                     2345

CTG  TTC  AAG  TTG  GGT  AAG  CCG  CTA  ACA  GCT  GAA  GAC  AAG  CAG  GAC  GAA         7169
Leu  Phe  Lys  Leu  Gly  Lys  Pro  Leu  Thr  Ala  Glu  Asp  Lys  Gln  Asp  Glu
               2350                     2355                     2360

GAC  AGG  CGA  CGA  GCA  CTG  AGT  GAC  GAG  GTT  AGC  AAG  TGG  TTC  CGG  ACA         7217
Asp  Arg  Arg  Arg  Ala  Leu  Ser  Asp  Glu  Val  Ser  Lys  Trp  Phe  Arg  Thr
          2365                     2370                     2375

GGC  TTG  GGG  GCC  GAA  CTG  GAG  GTG  GCA  CTA  ACA  TCT  AGG  TAT  GAG  GTA         7265
Gly  Leu  Gly  Ala  Glu  Leu  Glu  Val  Ala  Leu  Thr  Ser  Arg  Tyr  Glu  Val
     2380                     2385                     2390

GAG  GGC  TGC  AAA  AGT  ATC  CTC  ATA  GCC  ATG  ACC  ACC  TTG  GCG  AGG  GAC         7313
Glu  Gly  Cys  Lys  Ser  Ile  Leu  Ile  Ala  Met  Thr  Thr  Leu  Ala  Arg  Asp
2395                     2400                     2405

ATT  AAG  GCG  TTT  AAG  AAA  TTG  AGA  GGA  CCT  GTT  ATA  CAC  CTC  TAC  GGC         7361
Ile  Lys  Ala  Phe  Lys  Lys  Leu  Arg  Gly  Pro  Val  Ile  His  Leu  Tyr  Gly
2410                2415                     2420                     2425

GGT  CCT  AGA  TTG  GTG  CGT  TAATACACAG  AATTCTGATT  ATAGCGCACT                       7409
Gly  Pro  Arg  Leu  Val  Arg
               2430

ATTATAGCAC C ATG  AAT  TAC  ATC  CCT  ACG  CAA  ACG  TTT  TAC  GGC  CGC  CGG          7459
           Met  Asn  Tyr  Ile  Pro  Thr  Gln  Thr  Phe  Tyr  Gly  Arg  Arg
           1                5                          10

TGG  CGC  CCG  CGC  CCG  GCG  GCC  CGT  CCT  TGG  CCG  TTG  CAG  GCC  ACT  CCG         7507
Trp  Arg  Pro  Arg  Pro  Ala  Ala  Arg  Pro  Trp  Pro  Leu  Gln  Ala  Thr  Pro
     15                      20                      25

GTG  GCT  CCC  GTC  GTC  CCC  GAC  TTC  CAG  GCC  CAG  CAG  ATG  CAG  CAA  CTC         7555
Val  Ala  Pro  Val  Val  Pro  Asp  Phe  Gln  Ala  Gln  Gln  Met  Gln  Gln  Leu
30                      35                      40                      45

ATC  AGC  GCC  GTA  AAT  GCG  CTG  ACA  ATG  AGA  CAG  AAC  GCA  ATT  GCT  CCT         7603
Ile  Ser  Ala  Val  Asn  Ala  Leu  Thr  Met  Arg  Gln  Asn  Ala  Ile  Ala  Pro
               50                      55                      60

GCT  AGG  CCT  CCC  AAA  CCA  AAG  AAG  AAG  ACA  ACC  AAA  CCA  AAG  CCG               7651
Ala  Arg  Pro  Pro  Lys  Pro  Lys  Lys  Lys  Thr  Thr  Lys  Pro  Lys  Pro
          65                      70                      75

AAA  ACG  CAG  CCC  AAG  AAG  ATC  AAC  GGA  AAA  ACG  CAG  CAG  CAA  AAG  AAG         7699
Lys  Thr  Gln  Pro  Lys  Lys  Ile  Asn  Gly  Lys  Thr  Gln  Gln  Gln  Lys  Lys
               80                      85                      90

AAA  GAC  AAG  CAA  GCC  GAC  AAG  AAG  AAG  AAG  AAA  CCC  GGA  AAA  AGA  GAA         7747
Lys  Asp  Lys  Gln  Ala  Asp  Lys  Lys  Lys  Lys  Lys  Pro  Gly  Lys  Arg  Glu
```

-continued

|  |  |  | 95 |  |  |  |  | 100 |  |  |  |  | 105 |  |  |  |
|---|---|---|---|---|---|---|---|---|---|---|---|---|---|---|---|---|
| AGA | ATG | TGC | ATG | AAG | ATT | GAA | AAT | GAC | TGT | ATC | TTC | GAA | GTC | AAA | CAC | 7795 |
| Arg | Met | Cys | Met | Lys | Ile | Glu | Asn | Asp | Cys | Ile | Phe | Glu | Val | Lys | His |  |
| 110 |  |  |  | 115 |  |  |  |  | 120 |  |  |  |  | 125 |  |  |
| GAA | GGA | AAG | GTC | ACT | GGG | TAC | GCC | TGC | CTG | GTG | GGC | GAC | AAA | GTC | ATG | 7843 |
| Glu | Gly | Lys | Val | Thr | Gly | Tyr | Ala | Cys | Leu | Val | Gly | Asp | Lys | Val | Met |  |
|  |  |  |  | 130 |  |  |  |  | 135 |  |  |  |  | 140 |  |  |
| AAA | CCT | GCC | CAC | GTG | AAA | GGA | GTC | ATC | GAC | AAC | GCG | GAC | CTG | GCA | AAG | 7891 |
| Lys | Pro | Ala | His | Val | Lys | Gly | Val | Ile | Asp | Asn | Ala | Asp | Leu | Ala | Lys |  |
|  |  |  | 145 |  |  |  |  | 150 |  |  |  |  | 155 |  |  |  |
| CTA | GCT | TTC | AAG | AAA | TCG | AGC | AAG | TAT | GAC | CTT | GAG | TGT | GCC | CAG | ATA | 7939 |
| Leu | Ala | Phe | Lys | Lys | Ser | Ser | Lys | Tyr | Asp | Leu | Glu | Cys | Ala | Gln | Ile |  |
|  |  | 160 |  |  |  |  | 165 |  |  |  |  | 170 |  |  |  |  |
| CCA | GTT | CAC | ATG | AGG | TCG | GAT | GCC | TCA | AAG | TAC | ACG | CAT | GAG | AAG | CCC | 7987 |
| Pro | Val | His | Met | Arg | Ser | Asp | Ala | Ser | Lys | Tyr | Thr | His | Glu | Lys | Pro |  |
|  | 175 |  |  |  |  | 180 |  |  |  |  | 185 |  |  |  |  |  |
| GAG | GGA | CAC | TAT | AAC | TGG | CAC | CAC | GGG | GCT | GTT | CAG | TAC | AGC | GGA | GGT | 8035 |
| Glu | Gly | His | Tyr | Asn | Trp | His | His | Gly | Ala | Val | Gln | Tyr | Ser | Gly | Gly |  |
| 190 |  |  |  |  | 195 |  |  |  |  | 200 |  |  |  |  | 205 |  |
| AGG | TTC | ACT | ATA | CCG | ACA | GGA | GCG | GGC | AAA | CCG | GGA | GAC | AGT | GGC | CGG | 8083 |
| Arg | Phe | Thr | Ile | Pro | Thr | Gly | Ala | Gly | Lys | Pro | Gly | Asp | Ser | Gly | Arg |  |
|  |  |  |  | 210 |  |  |  |  | 215 |  |  |  |  | 220 |  |  |
| CCC | ATC | TTT | GAC | AAC | AAG | GGG | AGG | GTA | GTC | GCT | ATC | GTC | CTG | GGC | GGG | 8131 |
| Pro | Ile | Phe | Asp | Asn | Lys | Gly | Arg | Val | Val | Ala | Ile | Val | Leu | Gly | Gly |  |
|  |  |  | 225 |  |  |  |  | 230 |  |  |  |  | 235 |  |  |  |
| GCC | AAC | GAG | GGC | TCA | CGC | ACA | GCA | CTG | TCG | GTG | GTC | ACC | TGG | AAC | AAA | 8179 |
| Ala | Asn | Glu | Gly | Ser | Arg | Thr | Ala | Leu | Ser | Val | Val | Thr | Trp | Asn | Lys |  |
|  |  | 240 |  |  |  |  | 245 |  |  |  |  | 250 |  |  |  |  |
| GAT | ATG | GTG | ACT | AGA | GTG | ACC | CCC | GAG | GGG | TCC | GAA | GAG | TGG | TCC | GCC | 8227 |
| Asp | Met | Val | Thr | Arg | Val | Thr | Pro | Glu | Gly | Ser | Glu | Glu | Trp | Ser | Ala |  |
|  | 255 |  |  |  |  | 260 |  |  |  |  | 265 |  |  |  |  |  |
| CCG | CTG | ATT | ACT | GCC | ATG | TGT | GTC | CTT | GCC | AAT | GCT | ACC | TTC | CCG | TGC | 8275 |
| Pro | Leu | Ile | Thr | Ala | Met | Cys | Val | Leu | Ala | Asn | Ala | Thr | Phe | Pro | Cys |  |
| 270 |  |  |  |  | 275 |  |  |  |  | 280 |  |  |  |  | 285 |  |
| TTC | CAG | CCC | CCG | TGT | GTA | CCT | TGC | TGC | TAT | GAA | AAC | AAC | GCA | GAG | GCC | 8323 |
| Phe | Gln | Pro | Pro | Cys | Val | Pro | Cys | Cys | Tyr | Glu | Asn | Asn | Ala | Glu | Ala |  |
|  |  |  |  | 290 |  |  |  |  | 295 |  |  |  |  | 300 |  |  |
| ACA | CTA | CGG | ATG | CTC | GAG | GAT | AAC | GTG | GAT | AGG | CCA | GGG | TAC | TAC | GAC | 8371 |
| Thr | Leu | Arg | Met | Leu | Glu | Asp | Asn | Val | Asp | Arg | Pro | Gly | Tyr | Tyr | Asp |  |
|  |  |  | 305 |  |  |  |  | 310 |  |  |  |  | 315 |  |  |  |
| CTC | CTT | CAG | GCA | GCC | TTG | ACG | TGC | CGA | AAC | GGA | ACA | AGA | CAC | CGG | CGC | 8419 |
| Leu | Leu | Gln | Ala | Ala | Leu | Thr | Cys | Arg | Asn | Gly | Thr | Arg | His | Arg | Arg |  |
|  |  | 320 |  |  |  |  | 325 |  |  |  |  | 330 |  |  |  |  |
| AGC | GTG | TCG | CAA | CAC | TTC | AAC | GTG | TAT | AAG | GCT | ACA | CGC | CCT | TAC | ATC | 8467 |
| Ser | Val | Ser | Gln | His | Phe | Asn | Val | Tyr | Lys | Ala | Thr | Arg | Pro | Tyr | Ile |  |
|  | 335 |  |  |  |  | 340 |  |  |  |  | 345 |  |  |  |  |  |
| GCG | TAC | TGC | GCC | GAC | TGC | GGA | GCA | GGG | CAC | TCG | TGT | CAT | AGC | CCC | GTA | 8515 |
| Ala | Tyr | Cys | Ala | Asp | Cys | Gly | Ala | Gly | His | Ser | Cys | His | Ser | Pro | Val |  |
| 350 |  |  |  |  | 355 |  |  |  |  | 360 |  |  |  |  | 365 |  |
| GCA | ATT | GAA | GCG | GTC | AGG | TCC | GAA | GCT | ACC | GAC | GGG | ATG | CTG | AAG | ATT | 8563 |
| Ala | Ile | Glu | Ala | Val | Arg | Ser | Glu | Ala | Thr | Asp | Gly | Met | Leu | Lys | Ile |  |
|  |  |  |  | 370 |  |  |  |  | 375 |  |  |  |  | 380 |  |  |
| CAG | TTC | TCG | GCA | CAA | ATT | GGC | ATA | GAT | AAG | AGT | GAC | AAT | CAT | GAC | TAC | 8611 |
| Gln | Phe | Ser | Ala | Gln | Ile | Gly | Ile | Asp | Lys | Ser | Asp | Asn | His | Asp | Tyr |  |
|  |  |  | 385 |  |  |  |  | 390 |  |  |  |  | 395 |  |  |  |
| ACG | AAG | ATA | AGG | TAC | GCA | GAC | GGG | CAC | GCC | ATT | GAG | AAT | GCC | GTC | CGG | 8659 |
| Thr | Lys | Ile | Arg | Tyr | Ala | Asp | Gly | His | Ala | Ile | Glu | Asn | Ala | Val | Arg |  |
|  |  | 400 |  |  |  |  | 405 |  |  |  |  | 410 |  |  |  |  |
| TCA | TCT | TTG | AAG | GTA | GCC | ACC | TCC | GGA | GAC | TGT | TTC | GTC | CAT | GGC | ACA | 8707 |
| Ser | Ser | Leu | Lys | Val | Ala | Thr | Ser | Gly | Asp | Cys | Phe | Val | His | Gly | Thr |  |

|     |     |     |     |     |     |     |     |     |     |     |     |     |     |     |     |
|-----|-----|-----|-----|-----|-----|-----|-----|-----|-----|-----|-----|-----|-----|-----|-----|
|     |     |     | 415 |     |     |     | 420 |     |     |     |     | 425 |     |     |     |
| ATG | GGA | CAT | TTC | ATA | CTG | GCA | AAG | TGC | CCA | CCG | GGT | GAA | TTC | CTG | CAG |
| Met | Gly | His | Phe | Ile | Leu | Ala | Lys | Cys | Pro | Pro | Gly | Glu | Phe | Leu | Gln |
| 430 |     |     |     |     | 435 |     |     |     |     | 440 |     |     |     |     | 445 |
| GTC | TCG | ATC | CAG | GAC | ACC | AGA | AAC | GCG | GTC | CGT | GCC | TGC | AGA | ATA | CAA |
| Val | Ser | Ile | Gln | Asp | Thr | Arg | Asn | Ala | Val | Arg | Ala | Cys | Arg | Ile | Gln |
|     |     |     |     | 450 |     |     |     |     | 455 |     |     |     |     | 460 |     |
| TAT | CAT | CAT | GAC | CCT | CAA | CCG | GTG | GGT | AGA | GAA | AAA | TTT | ACA | ATT | AGA |
| Tyr | His | His | Asp | Pro | Gln | Pro | Val | Gly | Arg | Glu | Lys | Phe | Thr | Ile | Arg |
|     |     |     | 465 |     |     |     | 470 |     |     |     |     | 475 |     |     |     |
| CCA | CAC | TAT | GGA | AAA | GAG | ATC | CCT | TGC | ACC | ACT | TAT | CAA | CAG | ACC | ACA |
| Pro | His | Tyr | Gly | Lys | Glu | Ile | Pro | Cys | Thr | Thr | Tyr | Gln | Gln | Thr | Thr |
|     |     | 480 |     |     |     |     | 485 |     |     |     |     | 490 |     |     |     |
| GCG | AAG | ACC | GTG | GAG | GAA | ATC | GAC | ATG | CAT | ATG | CCG | CCA | GAT | ACG | CCG |
| Ala | Lys | Thr | Val | Glu | Glu | Ile | Asp | Met | His | Met | Pro | Pro | Asp | Thr | Pro |
|     | 495 |     |     |     |     | 500 |     |     |     |     | 505 |     |     |     |     |
| GAC | AGG | ACG | TTG | CTA | TCA | CAG | CAA | TCT | GGC | AAT | GTA | AAG | ATC | ACA | GTC |
| Asp | Arg | Thr | Leu | Leu | Ser | Gln | Gln | Ser | Gly | Asn | Val | Lys | Ile | Thr | Val |
| 510 |     |     |     |     | 515 |     |     |     |     | 520 |     |     |     |     | 525 |
| GGA | GGA | AAG | AAG | GTG | AAA | TAC | AAC | TGC | ACC | TGT | GGA | ACC | GGA | AAC | GTT |
| Gly | Gly | Lys | Lys | Val | Lys | Tyr | Asn | Cys | Thr | Cys | Gly | Thr | Gly | Asn | Val |
|     |     |     |     | 530 |     |     |     |     | 535 |     |     |     |     | 540 |     |
| GGC | ACT | ACT | AAT | TCG | GAC | ATG | ACG | ATC | AAC | ACG | TGT | CTA | ATA | GAG | CAG |
| Gly | Thr | Thr | Asn | Ser | Asp | Met | Thr | Ile | Asn | Thr | Cys | Leu | Ile | Glu | Gln |
|     |     |     | 545 |     |     |     | 550 |     |     |     |     | 555 |     |     |     |
| TGC | CAC | GTC | TCA | GTG | ACG | GAC | CAT | AAG | AAA | TGG | CAG | TTC | AAC | TCA | CCT |
| Cys | His | Val | Ser | Val | Thr | Asp | His | Lys | Lys | Trp | Gln | Phe | Asn | Ser | Pro |
|     |     | 560 |     |     |     |     | 565 |     |     |     |     | 570 |     |     |     |
| TTC | GTC | CCG | AGA | GCC | GAC | GAA | CCG | GCT | AGA | AAA | GGC | AAA | GTC | CAT | ATC |
| Phe | Val | Pro | Arg | Ala | Asp | Glu | Pro | Ala | Arg | Lys | Gly | Lys | Val | His | Ile |
|     | 575 |     |     |     |     | 580 |     |     |     |     | 585 |     |     |     |     |
| CCA | TTC | CCG | TTG | GAC | AAC | ATC | ACA | TGC | AGA | GTT | CCA | ATG | GCG | CGC | GAA |
| Pro | Phe | Pro | Leu | Asp | Asn | Ile | Thr | Cys | Arg | Val | Pro | Met | Ala | Arg | Glu |
| 590 |     |     |     |     | 595 |     |     |     |     | 600 |     |     |     |     | 605 |
| CCA | ACC | GTC | ATC | CAC | GGC | AAA | AGA | GAA | GTG | ACA | CTG | CAC | CTT | CAC | CCA |
| Pro | Thr | Val | Ile | His | Gly | Lys | Arg | Glu | Val | Thr | Leu | His | Leu | His | Pro |
|     |     |     |     | 610 |     |     |     |     | 615 |     |     |     |     | 620 |     |
| GAT | CAT | CCC | ACG | CTC | TTT | TCC | TAC | CGC | ACA | CTG | GGT | GAG | GAC | CCG | CAG |
| Asp | His | Pro | Thr | Leu | Phe | Ser | Tyr | Arg | Thr | Leu | Gly | Glu | Asp | Pro | Gln |
|     |     |     | 625 |     |     |     | 630 |     |     |     |     | 635 |     |     |     |
| TAT | CAC | GAG | GAA | TGG | GTG | ACA | GCG | GCG | GTG | GAA | CGG | ACC | ATA | CCC | GTA |
| Tyr | His | Glu | Glu | Trp | Val | Thr | Ala | Ala | Val | Glu | Arg | Thr | Ile | Pro | Val |
|     |     | 640 |     |     |     |     | 645 |     |     |     |     | 650 |     |     |     |
| CCA | GTG | GAC | GGG | ATG | GAG | TAC | CAC | TGG | GGA | AAC | AAC | GAC | CCA | GTG | AGG |
| Pro | Val | Asp | Gly | Met | Glu | Tyr | His | Trp | Gly | Asn | Asn | Asp | Pro | Val | Arg |
|     | 655 |     |     |     |     | 660 |     |     |     |     | 665 |     |     |     |     |
| CTT | TGG | TCT | CAA | CTC | ACC | ACT | GAA | GGG | AAA | CCG | CAC | GGC | TGG | CCG | CAT |
| Leu | Trp | Ser | Gln | Leu | Thr | Thr | Glu | Gly | Lys | Pro | His | Gly | Trp | Pro | His |
| 670 |     |     |     |     | 675 |     |     |     |     | 680 |     |     |     |     | 685 |
| CAG | ATC | GTA | CAG | TAC | TAC | TAT | GGG | CTT | TAC | CCG | GCC | GCT | ACA | GTA | TCC |
| Gln | Ile | Val | Gln | Tyr | Tyr | Tyr | Gly | Leu | Tyr | Pro | Ala | Ala | Thr | Val | Ser |
|     |     |     |     | 690 |     |     |     |     | 695 |     |     |     |     | 700 |     |
| GCG | GTC | GTC | GGG | ATG | AGC | TTA | CTG | GCG | TTG | ATA | TCG | ATC | TTC | GCG | TCG |
| Ala | Val | Val | Gly | Met | Ser | Leu | Leu | Ala | Leu | Ile | Ser | Ile | Phe | Ala | Ser |
|     |     |     | 705 |     |     |     | 710 |     |     |     |     | 715 |     |     |     |
| TGC | TAC | ATG | CTG | GTT | GCG | GCC | CGC | AGT | AAG | TGC | TTG | ACC | CCT | TAT | GCT |
| Cys | Tyr | Met | Leu | Val | Ala | Ala | Arg | Ser | Lys | Cys | Leu | Thr | Pro | Tyr | Ala |
|     |     | 720 |     |     |     |     | 725 |     |     |     |     | 730 |     |     |     |
| TTA | ACA | CCA | GGA | GCT | GCA | GTT | CCG | TGG | ACG | CTG | GGG | ATA | CTC | TGC | TGC |
| Leu | Thr | Pro | Gly | Ala | Ala | Val | Pro | Trp | Thr | Leu | Gly | Ile | Leu | Cys | Cys |

8755
8803
8851
8899
8947
8995
9043
9091
9139
9187
9235
9283
9331
9379
9427
9475
9523
9571
9619
9667

-continued

```
        735                           740                           745
GCC CCG CGG GCG CAC GCA GCT AGT GTG GCA GAG ACT ATG GCC TAC TTG           9715
Ala Pro Arg Ala His Ala Ala Ser Val Ala Glu Thr Met Ala Tyr Leu
750                 755                 760                 765
TGG GAC CAA AAC CAA GCG TTG TTC TGG TTG GAG TTT GCG GCC CCT GTT           9763
Trp Asp Gln Asn Gln Ala Leu Phe Trp Leu Glu Phe Ala Ala Pro Val
                    770                 775                 780
GCC TGC ATC CTC ATC ATC ACG TAT TGC CTC AGA AAC GTG CTG TGT TGC           9811
Ala Cys Ile Leu Ile Ile Thr Tyr Cys Leu Arg Asn Val Leu Cys Cys
                785                 790                 795
TGT AAG AGC CTT TCT TTT TTA GTG CTA CTG AGC CTC GGG GCA ACC GCC           9859
Cys Lys Ser Leu Ser Phe Leu Val Leu Leu Ser Leu Gly Ala Thr Ala
        800                 805                 810
AGA GCT TAC GAA CAT TCG ACA GTA ATG CCG AAC GTG GTG GGG TTC CCG           9907
Arg Ala Tyr Glu His Ser Thr Val Met Pro Asn Val Val Gly Phe Pro
        815                 820                 825
TAT AAG GCT CAC ATT GAA AGG CCA GGA TAT AGC CCC CTC ACT TTG CAG           9955
Tyr Lys Ala His Ile Glu Arg Pro Gly Tyr Ser Pro Leu Thr Leu Gln
830                 835                 840                 845
ATG CAG GTT GTT GAA ACC AGC CTC GAA CCA ACC CTT AAT TTG GAA TAC          10003
Met Gln Val Val Glu Thr Ser Leu Glu Pro Thr Leu Asn Leu Glu Tyr
                850                 855                 860
ATA ACC TGT GAG TAC AAG ACG GTC GTC CCG TCG CCG TAC GTG AAG TGC          10051
Ile Thr Cys Glu Tyr Lys Thr Val Val Pro Ser Pro Tyr Val Lys Cys
                865                 870                 875
TGC GGC GCC TCA GAG TGC TCC ACT AAA GAG AAG CCT GAC TAC CAA TGC          10099
Cys Gly Ala Ser Glu Cys Ser Thr Lys Glu Lys Pro Asp Tyr Gln Cys
                880                 885                 890
AAG GTT TAC ACA GGC GTG TAC CCG TTC ATG TGG GGA GGG GCA TAT TGC          10147
Lys Val Tyr Thr Gly Val Tyr Pro Phe Met Trp Gly Gly Ala Tyr Cys
        895                 900                 905
TTC TGC GAC TCA GAA AAC ACG CAA CTC AGC GAG GCG TAC GTC GAT CGA          10195
Phe Cys Asp Ser Glu Asn Thr Gln Leu Ser Glu Ala Tyr Val Asp Arg
910                 915                 920                 925
TCG GAC GTA TGC AGG CAT GAT CAC GCA TCT GCT TAC AAA GCC CAT ACA          10243
Ser Asp Val Cys Arg His Asp His Ala Ser Ala Tyr Lys Ala His Thr
                930                 935                 940
GCA TCG CTG AAG GCC AAA GTG AGG GTT ATG TAC GGC AAC GTA AAC CAG          10291
Ala Ser Leu Lys Ala Lys Val Arg Val Met Tyr Gly Asn Val Asn Gln
                945                 950                 955
ACT GTG GAT GTT TAC GTG AAC GGA GAC CAT GCC GTC ACG ATA GGG GGT          10339
Thr Val Asp Val Tyr Val Asn Gly Asp His Ala Val Thr Ile Gly Gly
                960                 965                 970
ACT CAG TTC ATA TTC GGG CCG CTG TCA TCG GCC TGG ACC CCG TTC GAC          10387
Thr Gln Phe Ile Phe Gly Pro Leu Ser Ser Ala Trp Thr Pro Phe Asp
        975                 980                 985
AAC AAG ATA GTC GTG TAC AAA GAC GAA GTG TTC AAT CAG GAC TTC CCG          10435
Asn Lys Ile Val Val Tyr Lys Asp Glu Val Phe Asn Gln Asp Phe Pro
990                 995                 1000                1005
CCG TAC GGA TCT GGG CAA CCA GGG CGC TTC GGC GAC ATC CAA AGC AGA          10483
Pro Tyr Gly Ser Gly Gln Pro Gly Arg Phe Gly Asp Ile Gln Ser Arg
                1010                1015                1020
ACA GTG GAG AGT AAC GAC CTG TAC GCG AAC ACG GCA CTG AAG CTG GCA          10531
Thr Val Glu Ser Asn Asp Leu Tyr Ala Asn Thr Ala Leu Lys Leu Ala
                1025                1030                1035
CGC CCT TCA CCC GGC ATG GTC CAT GTA CCG TAC ACA CAG ACA CCT TCA          10579
Arg Pro Ser Pro Gly Met Val His Val Pro Tyr Thr Gln Thr Pro Ser
                1040                1045                1050
GGG TTC AAA TAT TGG CTA AAG GAA AAA GGG ACA GCC CTA AAT ACG AAG          10627
Gly Phe Lys Tyr Trp Leu Lys Glu Lys Gly Thr Ala Leu Asn Thr Lys
```

```
          1055                    1060                    1065
GCT CCT TTT GGC TGC CAA ATC AAA ACG AAC CCT GTC AGG GCC ATG AAC      10675
Ala Pro Phe Gly Cys Gln Ile Lys Thr Asn Pro Val Arg Ala Met Asn
1070                1075                    1080                1085

TGC GCC GTG GGA AAC ATC CCT GTC TCC ATG AAT TTG CCT GAC AGC GCC      10723
Cys Ala Val Gly Asn Ile Pro Val Ser Met Asn Leu Pro Asp Ser Ala
                1090                    1095                1100

TTT ACC CGC ATT GTC GAG GCG CCG ACC ATC ATT GAC CTG ACT TGC ACA      10771
Phe Thr Arg Ile Val Glu Ala Pro Thr Ile Ile Asp Leu Thr Cys Thr
            1105                    1110                1115

GTG GCT ACC TGT ACG CAC TCC TCG GAT TTC GGC GGC GTC TTG ACA CTG      10819
Val Ala Thr Cys Thr His Ser Ser Asp Phe Gly Gly Val Leu Thr Leu
        1120                    1125                1130

ACG TAC AAG ACC AAC AAG AAC GGG GAC TGC TCT GTA CAC TCG CAC TCT      10867
Thr Tyr Lys Thr Asn Lys Asn Gly Asp Cys Ser Val His Ser His Ser
    1135                    1140                    1145

AAC GTA GCT ACT CTA CAG GAG GCC ACA GCA AAA GTG AAG ACA GCA GGT      10915
Asn Val Ala Thr Leu Gln Glu Ala Thr Ala Lys Val Lys Thr Ala Gly
1150                    1155                    1160                1165

AAG GTG ACC TTA CAC TTC TCC ACG GCA AGC GCA TCA CCT TCT TTT GTG      10963
Lys Val Thr Leu His Phe Ser Thr Ala Ser Ala Ser Pro Ser Phe Val
                1170                    1175                1180

GTG TCG CTA TGC AGT GCT AGG GCC ACC TGT TCA GCG TCG TGT GAG CCC      11011
Val Ser Leu Cys Ser Ala Arg Ala Thr Cys Ser Ala Ser Cys Glu Pro
            1185                    1190                1195

CCG AAA GAC CAC ATA GTC CCA TAT GCG GCT AGC CAC AGT AAC GTA GTG      11059
Pro Lys Asp His Ile Val Pro Tyr Ala Ala Ser His Ser Asn Val Val
        1200                    1205                1210

TTT CCA GAC ATG TCG GGC ACC GCA CTA TCA TGG GTG CAG AAA ATC TCG      11107
Phe Pro Asp Met Ser Gly Thr Ala Leu Ser Trp Val Gln Lys Ile Ser
    1215                    1220                    1225

GGT GGT CTG GGG GCC TTC GCA ATC GGC GCT ATC CTG GTG CTG GTT GTG      11155
Gly Gly Leu Gly Ala Phe Ala Ile Gly Ala Ile Leu Val Leu Val Val
1230                    1235                    1240                1245

GTC ACT TGC ATT GGG CTC CGC AGA TAAGTTAGGG TAGGCAATGG CATTGATATA     11209
Val Thr Cys Ile Gly Leu Arg Arg
                1250

GCAAGAAAAT TGAAACAGA AAAAGTTAGG GTAAGCAATG GCATATAACC ATAACTGTAT     11269

AACTTGTAAC AAAGCGCAAC AAGACCTGCG CAATTGGCCC CGTGGTCCGC CTCACGGAAA    11329

CTCGGGGCAA CTCATATTGA CACATTAATT GGCAATAATT GGAAGCTTAC ATAAGCTTAA    11389

TTCGACGAAT AATTGGATTT TTATTTTATT TTGCAATTGG TTTTAATAT TTCCAAAAAA     11449

AAAAAAAAAA AAAAAAAAAA AAAAAAAAAA AAAAAAAAAA AAAAAAAAAA AAAAAAAAAA    11509

AAAACTAG                                                             11517
```

( 2 ) INFORMATION FOR SEQ ID NO:2:

( i ) SEQUENCE CHARACTERISTICS:
        ( A ) LENGTH: 2431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Ala Lys Val His Val Asp Ile Glu Ala Asp Ser Pro Phe Ile
1               5                   10                  15

Lys Ser Leu Gln Lys Ala Phe Pro Ser Phe Glu Val Glu Ser Leu Gln
            20                  25                  30
```

| | | | | | | | | | | | | | | |
|---|---|---|---|---|---|---|---|---|---|---|---|---|---|---|
| Val | Thr | Pro 35 | Asn | Asp | His | Ala | Asn 40 | Ala | Arg | Ala | Phe | Ser 45 | His | Leu | Ala |
| Thr | Lys 50 | Leu | Ile | Glu | Gln | Glu 55 | Thr | Asp | Lys | Asp | Thr 60 | Leu | Ile | Leu | Asp |
| Ile 65 | Gly | Ser | Ala | Pro | Ser 70 | Arg | Arg | Met | Met | Ser 75 | Thr | His | Lys | Tyr | His 80 |
| Cys | Val | Cys | Pro | Met 85 | Arg | Ser | Ala | Glu | Asp 90 | Pro | Glu | Arg | Leu | Asp 95 | Ser |
| Tyr | Ala | Lys | Lys 100 | Leu | Ala | Ala | Ala | Ser 105 | Gly | Lys | Val | Leu | Asp 110 | Arg | Glu |
| Ile | Ala | Gly 115 | Lys | Ile | Thr | Asp | Leu 120 | Gln | Thr | Val | Met | Ala 125 | Thr | Pro | Asp |
| Ala | Glu 130 | Ser | Pro | Thr | Phe | Cys 135 | Leu | His | Thr | Asp | Val 140 | Thr | Cys | Arg | Thr |
| Ala 145 | Ala | Glu | Val | Ala | Val 150 | Tyr | Gln | Asp | Val | Tyr 155 | Ala | Val | His | Ala | Pro 160 |
| Thr | Ser | Leu | Tyr | His 165 | Gln | Ala | Met | Lys | Gly 170 | Val | Arg | Thr | Ala | Tyr 175 | Trp |
| Ile | Gly | Phe | Asp 180 | Thr | Thr | Pro | Phe | Met 185 | Phe | Asp | Ala | Leu | Ala 190 | Gly | Ala |
| Tyr | Pro | Thr 195 | Tyr | Ala | Thr | Asn | Trp 200 | Ala | Asp | Glu | Gln | Val 205 | Leu | Gln | Ala |
| Arg | Asn 210 | Ile | Gly | Leu | Cys | Ala 215 | Ala | Ser | Leu | Thr | Glu 220 | Gly | Arg | Leu | Gly |
| Lys 225 | Leu | Ser | Ile | Leu | Arg 230 | Lys | Lys | Gln | Leu | Lys 235 | Pro | Cys | Asp | Thr | Val 240 |
| Met | Phe | Ser | Val | Gly 245 | Ser | Thr | Leu | Tyr | Thr 250 | Glu | Ser | Arg | Lys | Leu 255 | Leu |
| Arg | Ser | Trp | His 260 | Leu | Pro | Ser | Val | Phe 265 | His | Leu | Lys | Gly | Lys 270 | Gln | Ser |
| Phe | Thr | Cys 275 | Arg | Cys | Asp | Thr | Ile 280 | Val | Ser | Cys | Glu | Gly 285 | Tyr | Val | Val |
| Lys | Lys 290 | Ile | Thr | Met | Cys | Pro 295 | Gly | Leu | Tyr | Gly | Lys 300 | Thr | Val | Gly | Tyr |
| Ala 305 | Val | Thr | Tyr | His | Ala 310 | Glu | Gly | Phe | Leu | Val 315 | Cys | Lys | Thr | Thr | Asp 320 |
| Thr | Val | Lys | Gly | Glu 325 | Arg | Val | Ser | Phe | Pro 330 | Val | Cys | Thr | Tyr | Val 335 | Pro |
| Ser | Thr | Ile | Cys 340 | Asp | Gln | Met | Thr | Gly 345 | Ile | Leu | Ala | Thr | Asp 350 | Val | Thr |
| Pro | Glu | Asp 355 | Ala | Gln | Lys | Leu | Leu 360 | Val | Gly | Leu | Asn | Gln 365 | Arg | Ile | Val |
| Val | Asn 370 | Gly | Arg | Thr | Gln | Arg 375 | Asn | Thr | Asn | Thr | Met 380 | Lys | Asn | Tyr | Leu |
| Leu 385 | Pro | Ile | Val | Ala | Val 390 | Ala | Phe | Ser | Lys | Trp 395 | Ala | Arg | Glu | Tyr | Lys 400 |
| Ala | Asp | Leu | Asp | Asp 405 | Glu | Lys | Pro | Leu | Gly 410 | Val | Arg | Glu | Arg | Ser 415 | Leu |
| Thr | Cys | Cys | Cys 420 | Leu | Trp | Ala | Phe | Lys 425 | Thr | Arg | Lys | Met | His 430 | Thr | Met |
| Tyr | Lys | Lys 435 | Pro | Asp | Thr | Gln | Thr 440 | Ile | Val | Lys | Val | Pro 445 | Ser | Glu | Phe |
| Asn | Ser 450 | Phe | Val | Ile | Pro | Ser 455 | Leu | Trp | Ser | Thr | Gly 460 | Leu | Ala | Ile | Pro |

| Val | Arg | Ser | Arg | Ile | Lys | Met | Leu | Leu | Ala | Lys | Lys | Thr | Lys | Arg | Glu |
| 465 | | | | 470 | | | | | 475 | | | | | | 480 |
| Leu | Ile | Pro | Val | Leu | Asp | Ala | Ser | Ser | Arg | Asp | Ala | Glu | Gln | Glu |
| | | | | 485 | | | | | 490 | | | | | 495 |
| Glu | Lys | Glu | Arg | Leu | Glu | Ala | Glu | Leu | Thr | Arg | Glu | Ala | Leu | Pro | Pro |
| | | | 500 | | | | | 505 | | | | | 510 | |
| Leu | Val | Pro | Ile | Ala | Pro | Ala | Glu | Thr | Gly | Val | Val | Asp | Val | Asp | Val |
| | | | 515 | | | | 520 | | | | | 525 | | | |
| Glu | Glu | Leu | Glu | Tyr | His | Ala | Gly | Ala | Gly | Val | Val | Glu | Thr | Pro | Arg |
| | 530 | | | | | 535 | | | | | 540 | | | | |
| Ser | Ala | Leu | Lys | Val | Thr | Ala | Gln | Pro | Asn | Asp | Val | Leu | Leu | Gly | Asn |
| 545 | | | | | 550 | | | | 555 | | | | | | 560 |
| Tyr | Val | Val | Leu | Ser | Pro | Gln | Thr | Val | Leu | Lys | Ser | Ser | Lys | Leu | Ala |
| | | | | 565 | | | | | 570 | | | | | 575 | |
| Pro | Val | His | Pro | Leu | Ala | Glu | Gln | Val | Lys | Ile | Ile | Thr | His | Asn | Gly |
| | | | 580 | | | | | 585 | | | | | 590 | | |
| Arg | Ala | Gly | Gly | Tyr | Gln | Val | Asp | Gly | Tyr | Asp | Gly | Arg | Val | Leu | Leu |
| | | 595 | | | | | 600 | | | | | 605 | | | |
| Pro | Cys | Gly | Ser | Ala | Ile | Pro | Val | Pro | Glu | Phe | Gln | Ala | Leu | Ser | Glu |
| | 610 | | | | | 615 | | | | | 620 | | | | |
| Ser | Ala | Thr | Met | Val | Tyr | Asn | Glu | Arg | Glu | Phe | Val | Asn | Arg | Lys | Leu |
| 625 | | | | | 630 | | | | | 635 | | | | | 640 |
| Tyr | His | Ile | Ala | Val | His | Gly | Pro | Ser | Leu | Asn | Thr | Asp | Glu | Glu | Asn |
| | | | | 645 | | | | | 650 | | | | | 655 | |
| Tyr | Glu | Lys | Val | Arg | Ala | Glu | Arg | Thr | Asp | Ala | Glu | Tyr | Val | Phe | Asp |
| | | | 660 | | | | 665 | | | | | 670 | | | |
| Val | Asp | Lys | Lys | Cys | Cys | Val | Lys | Arg | Glu | Glu | Ala | Ser | Gly | Leu | Val |
| | | 675 | | | | | 680 | | | | | 685 | | | |
| Leu | Val | Gly | Glu | Leu | Thr | Asn | Pro | Pro | Phe | His | Glu | Phe | Ala | Tyr | Glu |
| | 690 | | | | | 695 | | | | | 700 | | | | |
| Gly | Leu | Lys | Ile | Arg | Pro | Ser | Ala | Pro | Tyr | Lys | Thr | Thr | Val | Val | Gly |
| 705 | | | | | 710 | | | | | 715 | | | | | 720 |
| Val | Phe | Gly | Val | Pro | Gly | Ser | Gly | Lys | Ser | Ala | Ile | Ile | Lys | Ser | Leu |
| | | | | 725 | | | | | 730 | | | | | 735 | |
| Val | Thr | Lys | His | Asp | Leu | Val | Thr | Ser | Gly | Lys | Lys | Glu | Asn | Cys | Gln |
| | | | 740 | | | | | 745 | | | | | 750 | | |
| Glu | Ile | Val | Asn | Asp | Val | Lys | Lys | His | Arg | Gly | Lys | Gly | Thr | Ser | Arg |
| | | 755 | | | | | 760 | | | | | 765 | | | |
| Glu | Asn | Ser | Asp | Ser | Ile | Leu | Leu | Asn | Gly | Cys | Arg | Arg | Ala | Val | Asp |
| | 770 | | | | | 775 | | | | | 780 | | | | |
| Ile | Leu | Tyr | Val | Asp | Glu | Ala | Phe | Ala | Cys | His | Ser | Gly | Thr | Leu | Leu |
| 785 | | | | | 790 | | | | | 795 | | | | | 800 |
| Ala | Leu | Ile | Ala | Leu | Val | Lys | Pro | Arg | Ser | Lys | Val | Val | Leu | Cys | Gly |
| | | | | 805 | | | | | 810 | | | | | 815 | |
| Asp | Pro | Lys | Gln | Cys | Gly | Phe | Phe | Asn | Met | Met | Gln | Leu | Lys | Val | Asn |
| | | | 820 | | | | | 825 | | | | | 830 | | |
| Phe | Asn | His | Asn | Ile | Cys | Thr | Glu | Val | Cys | His | Lys | Ser | Ile | Ser | Arg |
| | | 835 | | | | | 840 | | | | | 845 | | | |
| Arg | Cys | Thr | Arg | Pro | Val | Thr | Ala | Ile | Val | Ser | Thr | Leu | His | Tyr | Gly |
| | 850 | | | | | 855 | | | | | 860 | | | | |
| Gly | Lys | Met | Arg | Thr | Thr | Asn | Pro | Cys | Asn | Lys | Pro | Ile | Ile | Ile | Asp |
| 865 | | | | | 870 | | | | | 875 | | | | | 880 |
| Thr | Thr | Gly | Gln | Thr | Lys | Pro | Lys | Pro | Gly | Asp | Ile | Val | Leu | Thr | Cys |

-continued

|  |  |  | 885 |  |  |  | 890 |  |  |  | 895 |  |  |
|---|---|---|---|---|---|---|---|---|---|---|---|---|---|

Phe Arg Gly Trp Ala Lys Gln Leu Gln Leu Asp Tyr Arg Gly His Glu
            900                     905                     910

Val Met Thr Ala Ala Ser Gln Gly Leu Thr Arg Lys Gly Val Tyr
            915                     920                     925

Ala Val Arg Gln Lys Val Asn Glu Asn Pro Leu Tyr Ala Pro Ala Ser
            930                     935                     940

Glu His Val Asn Val Leu Leu Thr Arg Thr Glu Asp Arg Leu Val Trp
945                     950                     955                     960

Lys Thr Leu Ala Gly Asp Pro Trp Ile Lys Val Leu Ser Asn Ile Pro
                        965                     970                     975

Gln Gly Asn Phe Thr Ala Thr Leu Glu Glu Trp Gln Glu His Asp
            980                     985                     990

Lys Ile Met Lys Val Ile Glu Gly Pro Ala Ala Pro Val Asp Ala Phe
            995                     1000                    1005

Gln Asn Lys Ala Asn Val Cys Trp Ala Lys Ser Leu Val Pro Val Leu
            1010                    1015                    1020

Asp Thr Ala Gly Ile Arg Leu Thr Ala Glu Glu Trp Ser Thr Ile Ile
1025                    1030                    1035                    1040

Thr Ala Phe Lys Glu Asp Arg Ala Tyr Ser Pro Val Val Ala Leu Asn
            1045                    1050                    1055

Glu Ile Cys Thr Lys Tyr Tyr Gly Val Asp Leu Asp Ser Gly Leu Phe
            1060                    1065                    1070

Ser Ala Pro Lys Val Ser Leu Tyr Tyr Glu Asn Asn His Trp Asp Asn
            1075                    1080                    1085

Arg Pro Gly Gly Arg Met Tyr Gly Phe Asn Ala Ala Thr Ala Ala Arg
            1090                    1095                    1100

Leu Glu Ala Arg His Thr Phe Leu Lys Gly Gln Trp His Thr Gly Lys
1105                    1110                    1115                    1120

Gln Ala Val Ile Ala Glu Arg Lys Ile Gln Pro Leu Ser Val Leu Asp
            1125                    1130                    1135

Asn Val Ile Pro Ile Asn Arg Arg Leu Pro His Ala Leu Val Ala Glu
            1140                    1145                    1150

Tyr Lys Thr Val Lys Gly Ser Arg Val Glu Trp Leu Val Asn Lys Val
            1155                    1160                    1165

Arg Gly Tyr His Val Leu Leu Val Ser Glu Tyr Asn Leu Ala Leu Pro
            1170                    1175                    1180

Arg Arg Arg Val Thr Trp Leu Ser Pro Leu Asn Val Thr Gly Ala Asp
1185                    1190                    1195                    1200

Arg Cys Tyr Asp Leu Ser Leu Gly Leu Pro Ala Asp Ala Gly Arg Phe
            1205                    1210                    1215

Asp Leu Val Phe Val Asn Ile His Thr Glu Phe Arg Ile His His Tyr
            1220                    1225                    1230

Gln Gln Cys Val Asp His Ala Met Lys Leu Gln Met Leu Gly Gly Asp
            1235                    1240                    1245

Ala Leu Arg Leu Leu Lys Pro Gly Gly Ile Leu Met Arg Ala Tyr Gly
            1250                    1255                    1260

Tyr Ala Asp Lys Ile Ser Glu Ala Val Val Ser Ser Leu Ser Arg Lys
1265                    1270                    1275                    1280

Phe Ser Ser Ala Arg Val Leu Arg Pro Asp Cys Val Thr Ser Asn Thr
            1285                    1290                    1295

Glu Val Phe Leu Leu Phe Ser Asn Phe Asp Asn Gly Lys Arg Pro Ser
            1300                    1305                    1310

```
Thr Leu His Gln Met Asn Thr Lys Leu Ser Ala Val Tyr Ala Gly Glu
        1315                1320                1325
Ala Met His Thr Ala Gly Cys Ala Pro Ser Tyr Arg Val Lys Arg Ala
        1330                1335                1340
Asp Ile Ala Thr Cys Thr Glu Ala Ala Val Val Asn Ala Ala Asn Ala
1345                    1350                1355                1360
Arg Gly Thr Val Gly Asp Gly Val Cys Arg Ala Val Ala Lys Lys Trp
                1365                1370                1375
Pro Ser Ala Phe Lys Gly Ala Ala Thr Pro Val Gly Thr Ile Lys Thr
        1380                1385                1390
Val Met Cys Gly Ser Tyr Pro Val Ile His Ala Val Ala Pro Asn Phe
        1395                1400                1405
Ser Ala Thr Thr Glu Ala Glu Gly Asp Arg Glu Leu Ala Ala Val Tyr
        1410                1415                1420
Arg Ala Val Ala Ala Glu Val Asn Arg Leu Ser Leu Ser Ser Val Ala
1425                    1430                1435                1440
Ile Pro Leu Leu Ser Thr Gly Val Phe Ser Gly Gly Arg Asp Arg Leu
                1445                1450                1455
Gln Gln Ser Leu Asn His Leu Phe Thr Ala Met Asp Ala Thr Asp Ala
        1460                1465                1470
Asp Val Thr Ile Tyr Cys Arg Asp Lys Ser Trp Glu Lys Lys Ile Gln
        1475                1480                1485
Glu Ala Ile Asp Met Arg Thr Ala Val Glu Leu Leu Asn Asp Asp Val
        1490                1495                1500
Glu Leu Thr Thr Asp Leu Val Arg Val His Pro Asp Ser Ser Leu Val
1505                    1510                1515                1520
Gly Arg Lys Gly Tyr Ser Thr Thr Asp Gly Ser Leu Tyr Ser Tyr Phe
                1525                1530                1535
Glu Gly Thr Lys Phe Asn Gln Ala Ala Ile Asp Met Ala Glu Ile Leu
        1540                1545                1550
Thr Leu Trp Pro Arg Leu Gln Glu Ala Asn Glu Gln Ile Cys Leu Tyr
        1555                1560                1565
Ala Leu Gly Glu Thr Met Asp Asn Ile Arg Ser Lys Cys Pro Val Asn
        1570                1575                1580
Asp Ser Asp Ser Ser Thr Pro Pro Arg Thr Val Pro Cys Leu Cys Arg
1585                    1590                1595                1600
Tyr Ala Met Thr Ala Glu Arg Ile Ala Arg Leu Arg Ser His Gln Val
                1605                1610                1615
Lys Ser Met Val Val Cys Ser Ser Phe Pro Leu Pro Lys Tyr His Val
        1620                1625                1630
Asp Gly Val Gln Lys Val Lys Cys Glu Lys Val Leu Leu Phe Asp Pro
        1635                1640                1645
Thr Val Pro Ser Val Val Ser Pro Arg Lys Tyr Ala Ala Ser Thr Thr
        1650                1655                1660
Asp His Ser Asp Arg Ser Leu Arg Gly Phe Asp Leu Asp Trp Thr Thr
1665                    1670                1675                1680
Asp Ser Ser Ser Thr Ala Ser Asp Thr Met Ser Leu Pro Ser Leu Gln
                1685                1690                1695
Ser Cys Asp Ile Asp Ser Ile Tyr Glu Pro Met Ala Pro Ile Val Val
        1700                1705                1710
Thr Ala Asp Val His Pro Glu Pro Ala Gly Ile Ala Asp Leu Ala Ala
        1715                1720                1725
Asp Val His Pro Glu Pro Ala Asp His Val Asp Leu Glu Asn Pro Ile
        1730                1735                1740
```

```
Pro Pro Pro Arg Pro Lys Arg Ala Ala Tyr Leu Ala Ser Arg Ala Ala
1745             1750            1755                1760
Glu Arg Pro Val Pro Ala Pro Arg Lys Pro Thr Pro Ala Pro Arg Thr
                1765            1770            1775
Ala Phe Arg Asn Lys Leu Pro Leu Thr Phe Gly Asp Phe Asp Glu His
            1780            1785            1790
Glu Val Asp Ala Leu Ala Ser Gly Ile Thr Phe Gly Asp Phe Asp Asp
            1795            1800            1805
Val Leu Arg Leu Gly Arg Ala Gly Ala Tyr Ile Phe Ser Ser Asp Thr
        1810            1815            1820
Gly Ser Gly His Leu Gln Gln Lys Ser Val Arg Gln His Asn Leu Gln
1825            1830            1835                1840
Cys Ala Gln Leu Asp Ala Val Gln Glu Glu Lys Met Tyr Pro Pro Lys
                1845            1850            1855
Leu Asp Thr Glu Arg Glu Lys Leu Leu Leu Leu Lys Met Gln Met His
            1860            1865            1870
Pro Ser Glu Ala Asn Lys Ser Arg Tyr Gln Ser Arg Lys Val Glu Asn
            1875            1880            1885
Met Lys Ala Thr Val Val Asp Arg Leu Thr Ser Gly Ala Arg Leu Tyr
        1890            1895            1900
Thr Gly Ala Asp Val Gly Arg Ile Pro Thr Tyr Ala Val Arg Tyr Pro
1905            1910            1915                1920
Arg Pro Val Tyr Ser Pro Thr Val Ile Glu Arg Phe Ser Ser Pro Asp
            1925            1930            1935
Val Ala Ile Ala Ala Cys Asn Glu Tyr Leu Ser Arg Asn Tyr Pro Thr
            1940            1945            1950
Val Ala Ser Tyr Gln Ile Thr Asp Glu Tyr Asp Ala Tyr Leu Asp Met
        1955            1960            1965
Val Asp Gly Ser Asp Ser Cys Leu Asp Arg Ala Thr Phe Cys Pro Ala
        1970            1975            1980
Lys Leu Arg Cys Tyr Pro Lys His His Ala Tyr His Gln Pro Thr Val
1985            1990            1995                2000
Arg Ser Ala Val Pro Ser Pro Phe Gln Asn Thr Leu Gln Asn Val Leu
            2005            2010            2015
Ala Ala Ala Thr Lys Arg Asn Cys Asn Val Thr Gln Met Arg Glu Leu
        2020            2025            2030
Pro Thr Met Asp Ser Ala Val Phe Asn Val Glu Cys Phe Lys Arg Tyr
        2035            2040            2045
Ala Cys Ser Gly Glu Tyr Trp Glu Glu Tyr Ala Lys Gln Pro Ile Arg
2050            2055            2060
Ile Thr Thr Glu Asn Ile Thr Thr Tyr Val Thr Lys Leu Lys Gly Pro
2065            2070            2075                2080
Lys Ala Ala Ala Leu Phe Ala Lys Thr His Asn Leu Val Pro Leu Gln
            2085            2090            2095
Glu Val Pro Met Asp Arg Phe Thr Val Asp Met Lys Arg Asp Val Lys
            2100            2105            2110
Val Thr Pro Gly Thr Lys His Thr Glu Glu Arg Pro Lys Val Gln Val
        2115            2120            2125
Ile Gln Ala Ala Glu Pro Leu Ala Thr Ala Tyr Leu Cys Gly Ile His
        2130            2135            2140
Arg Glu Leu Val Arg Arg Leu Asn Ala Val Leu Arg Pro Asn Val His
2145            2150            2155                2160
Thr Leu Phe Asp Met Ser Ala Glu Asp Phe Asp Ala Ile Ile Ala Ser
```

|   |   |   |   |   | 2165 |   |   |   |   | 2170 |   |   |   |   | 2175 |   |
|---|---|---|---|---|------|---|---|---|---|------|---|---|---|---|------|---|

His Phe His Pro Gly Asp Pro Val Leu Glu Thr Asp Ile Ala Ser Phe
              2180                2185              2190

Asp Lys Ser Gln Asp Asp Ser Leu Ala Leu Thr Gly Leu Met Ile Leu
              2195                2200              2205

Glu Asp Leu Gly Val Asp Gln Tyr Leu Leu Asp Leu Ile Glu Ala Ala
              2210                2215              2220

Phe Gly Glu Ile Ser Ser Cys His Leu Pro Thr Gly Thr Arg Phe Lys
2225               2230               2235                2240

Phe Gly Ala Met Met Lys Ser Gly Met Phe Leu Thr Leu Phe Ile Asn
              2245                2250              2255

Thr Val Leu Asn Ile Thr Ile Ala Ser Arg Val Leu Glu Gln Arg Leu
              2260                2265              2270

Thr Asp Ser Ala Cys Ala Ala Phe Ile Gly Asp Asp Asn Ile Val His
              2275                2280              2285

Gly Val Ile Ser Asp Lys Leu Met Ala Glu Arg Cys Ala Ser Trp Val
              2290                2295              2300

Asn Met Glu Val Lys Ile Ile Asp Ala Val Met Gly Glu Lys Pro Pro
2305               2310               2315                2320

Tyr Phe Cys Gly Gly Phe Ile Val Phe Asp Ser Val Thr Gln Thr Ala
              2325                2330              2335

Cys Arg Val Ser Asp Pro Leu Lys Arg Leu Phe Lys Leu Gly Lys Pro
              2340                2345              2350

Leu Thr Ala Glu Asp Lys Gln Asp Glu Asp Arg Arg Arg Ala Leu Ser
              2355                2360              2365

Asp Glu Val Ser Lys Trp Phe Arg Thr Gly Leu Gly Ala Glu Leu Glu
              2370                2375              2380

Val Ala Leu Thr Ser Arg Tyr Glu Val Glu Gly Cys Lys Ser Ile Leu
2385               2390               2395                2400

Ile Ala Met Thr Thr Leu Ala Arg Asp Ile Lys Ala Phe Lys Lys Leu
              2405                2410              2415

Arg Gly Pro Val Ile His Leu Tyr Gly Gly Pro Arg Leu Val Arg
              2420                2425              2430

(2) INFORMATION FOR SEQ ID NO:3:

(i) SEQUENCE CHARACTERISTICS:
        (A) LENGTH: 1253 amino acids
        (B) TYPE: amino acid
        (D) TOPOLOGY: linear (ii) MOLECULE TYPE: protein (xi) SEQUENCE DESCRIPTION: SEQ ID NO:3:

Met Asn Tyr Ile Pro Thr Gln Thr Phe Tyr Gly Arg Arg Trp Arg Pro
1                  5                  10                 15

Arg Pro Ala Ala Arg Pro Trp Pro Leu Gln Ala Thr Pro Val Ala Pro
              20                  25                 30

Val Val Pro Asp Phe Gln Ala Gln Gln Met Gln Gln Leu Ile Ser Ala
              35                  40                 45

Val Asn Ala Leu Thr Met Arg Gln Asn Ala Ile Ala Pro Ala Arg Pro
              50                  55                 60

Pro Lys Pro Lys Lys Lys Lys Thr Thr Lys Pro Lys Pro Lys Thr Gln
65                  70                  75                  80

Pro Lys Lys Ile Asn Gly Lys Thr Gln Gln Gln Lys Lys Lys Asp Lys
              85                  90                 95

```
Gln Ala Asp Lys Lys Lys Lys Lys Pro Gly Lys Arg Glu Arg Met Cys
            100             105             110

Met Lys Ile Glu Asn Asp Cys Ile Phe Glu Val Lys His Glu Gly Lys
        115             120             125

Val Thr Gly Tyr Ala Cys Leu Val Gly Asp Lys Val Met Lys Pro Ala
        130             135             140

His Val Lys Gly Val Ile Asp Asn Ala Asp Leu Ala Lys Leu Ala Phe
145             150             155                         160

Lys Lys Ser Ser Lys Tyr Asp Leu Glu Cys Ala Gln Ile Pro Val His
                165             170             175

Met Arg Ser Asp Ala Ser Lys Tyr Thr His Glu Lys Pro Glu Gly His
            180             185             190

Tyr Asn Trp His His Gly Ala Val Gln Tyr Ser Gly Gly Arg Phe Thr
        195             200             205

Ile Pro Thr Gly Ala Gly Lys Pro Gly Asp Ser Gly Arg Pro Ile Phe
    210             215             220

Asp Asn Lys Gly Arg Val Val Ala Ile Val Leu Gly Gly Ala Asn Glu
225             230             235                         240

Gly Ser Arg Thr Ala Leu Ser Val Val Thr Trp Asn Lys Asp Met Val
            245             250             255

Thr Arg Val Thr Pro Glu Gly Ser Glu Glu Trp Ser Ala Pro Leu Ile
            260             265             270

Thr Ala Met Cys Val Leu Ala Asn Ala Thr Phe Pro Cys Phe Gln Pro
            275             280             285

Pro Cys Val Pro Cys Cys Tyr Glu Asn Asn Ala Glu Ala Thr Leu Arg
    290             295             300

Met Leu Glu Asp Asn Val Asp Arg Pro Gly Tyr Tyr Asp Leu Leu Gln
305             310             315             320

Ala Ala Leu Thr Cys Arg Asn Gly Thr Arg His Arg Arg Ser Val Ser
            325             330             335

Gln His Phe Asn Val Tyr Lys Ala Thr Arg Pro Tyr Ile Ala Tyr Cys
            340             345             350

Ala Asp Cys Gly Ala Gly His Ser Cys His Ser Pro Val Ala Ile Glu
            355             360             365

Ala Val Arg Ser Glu Ala Thr Asp Gly Met Leu Lys Ile Gln Phe Ser
    370             375             380

Ala Gln Ile Gly Ile Asp Lys Ser Asp Asn His Asp Tyr Thr Lys Ile
385             390             395             400

Arg Tyr Ala Asp Gly His Ala Ile Glu Asn Ala Val Arg Ser Ser Leu
            405             410             415

Lys Val Ala Thr Ser Gly Asp Cys Phe Val His Gly Thr Met Gly His
            420             425             430

Phe Ile Leu Ala Lys Cys Pro Pro Gly Glu Phe Leu Gln Val Ser Ile
        435             440             445

Gln Asp Thr Arg Asn Ala Val Arg Ala Cys Arg Ile Gln Tyr His His
    450             455             460

Asp Pro Gln Pro Val Gly Arg Glu Lys Phe Thr Ile Arg Pro His Tyr
465             470             475             480

Gly Lys Glu Ile Pro Cys Thr Thr Tyr Gln Gln Thr Thr Ala Lys Thr
            485             490             495

Val Glu Glu Ile Asp Met His Met Pro Pro Asp Thr Pro Asp Arg Thr
            500             505             510

Leu Leu Ser Gln Gln Ser Gly Asn Val Lys Ile Thr Val Gly Gly Lys
            515             520             525
```

| | | | | | | | | | | | | | | |
|---|---|---|---|---|---|---|---|---|---|---|---|---|---|---|
| Lys | Val | Lys | Tyr | Asn | Cys | Thr | Cys | Gly | Thr | Gly | Asn | Val | Gly | Thr | Thr |
| | 530 | | | | 535 | | | | 540 | | | | | | |
| Asn | Ser | Asp | Met | Thr | Ile | Asn | Thr | Cys | Leu | Ile | Glu | Gln | Cys | His | Val |
| 545 | | | | | 550 | | | | 555 | | | | | | 560 |
| Ser | Val | Thr | Asp | His | Lys | Lys | Trp | Gln | Phe | Asn | Ser | Pro | Phe | Val | Pro |
| | | | | 565 | | | | 570 | | | | | 575 | | |
| Arg | Ala | Asp | Glu | Pro | Ala | Arg | Lys | Gly | Lys | Val | His | Ile | Pro | Phe | Pro |
| | | | 580 | | | | 585 | | | | | 590 | | | |
| Leu | Asp | Asn | Ile | Thr | Cys | Arg | Val | Pro | Met | Ala | Arg | Glu | Pro | Thr | Val |
| | | 595 | | | | 600 | | | | 605 | | | | | |
| Ile | His | Gly | Lys | Arg | Glu | Val | Thr | Leu | His | Leu | His | Pro | Asp | His | Pro |
| | 610 | | | | | 615 | | | 620 | | | | | | |
| Thr | Leu | Phe | Ser | Tyr | Arg | Thr | Leu | Gly | Glu | Asp | Pro | Gln | Tyr | His | Glu |
| 625 | | | | | 630 | | | | 635 | | | | | | 640 |
| Glu | Trp | Val | Thr | Ala | Ala | Val | Glu | Arg | Thr | Ile | Pro | Val | Pro | Val | Asp |
| | | | | 645 | | | | | 650 | | | | 655 | | |
| Gly | Met | Glu | Tyr | His | Trp | Gly | Asn | Asn | Asp | Pro | Val | Arg | Leu | Trp | Ser |
| | | | 660 | | | | | 665 | | | | | 670 | | |
| Gln | Leu | Thr | Thr | Glu | Gly | Lys | Pro | His | Gly | Trp | Pro | His | Gln | Ile | Val |
| | | 675 | | | | | 680 | | | | | 685 | | | |
| Gln | Tyr | Tyr | Tyr | Gly | Leu | Tyr | Pro | Ala | Ala | Thr | Val | Ser | Ala | Val | Val |
| | 690 | | | | | 695 | | | | | 700 | | | | |
| Gly | Met | Ser | Leu | Leu | Ala | Leu | Ile | Ser | Ile | Phe | Ala | Ser | Cys | Tyr | Met |
| 705 | | | | 710 | | | | | 715 | | | | | | 720 |
| Leu | Val | Ala | Ala | Arg | Ser | Lys | Cys | Leu | Thr | Pro | Tyr | Ala | Leu | Thr | Pro |
| | | | | 725 | | | | | 730 | | | | | 735 | |
| Gly | Ala | Ala | Val | Pro | Trp | Thr | Leu | Gly | Ile | Leu | Cys | Cys | Ala | Pro | Arg |
| | | | 740 | | | | | 745 | | | | | 750 | | |
| Ala | His | Ala | Ala | Ser | Val | Ala | Glu | Thr | Met | Ala | Tyr | Leu | Trp | Asp | Gln |
| | | 755 | | | | 760 | | | | | 765 | | | | |
| Asn | Gln | Ala | Leu | Phe | Trp | Leu | Glu | Phe | Ala | Ala | Pro | Val | Ala | Cys | Ile |
| | 770 | | | | | 775 | | | | | 780 | | | | |
| Leu | Ile | Ile | Thr | Tyr | Cys | Leu | Arg | Asn | Val | Leu | Cys | Cys | Cys | Lys | Ser |
| 785 | | | | | 790 | | | | | 795 | | | | | 800 |
| Leu | Ser | Phe | Leu | Val | Leu | Leu | Ser | Leu | Gly | Ala | Thr | Ala | Arg | Ala | Tyr |
| | | | | 805 | | | | | 810 | | | | | 815 | |
| Glu | His | Ser | Thr | Val | Met | Pro | Asn | Val | Val | Gly | Phe | Pro | Tyr | Lys | Ala |
| | | | 820 | | | | | 825 | | | | | 830 | | |
| His | Ile | Glu | Arg | Pro | Gly | Tyr | Ser | Pro | Leu | Thr | Leu | Gln | Met | Gln | Val |
| | | | 835 | | | | 840 | | | | | 845 | | | |
| Val | Glu | Thr | Ser | Leu | Glu | Pro | Thr | Leu | Asn | Leu | Glu | Tyr | Ile | Thr | Cys |
| | 850 | | | | | 855 | | | | | 860 | | | | |
| Glu | Tyr | Lys | Thr | Val | Val | Pro | Ser | Pro | Tyr | Val | Lys | Cys | Cys | Gly | Ala |
| 865 | | | | | 870 | | | | | 875 | | | | | 880 |
| Ser | Glu | Cys | Ser | Thr | Lys | Glu | Lys | Pro | Asp | Tyr | Gln | Cys | Lys | Val | Tyr |
| | | | | 885 | | | | 890 | | | | | | 895 | |
| Thr | Gly | Val | Tyr | Pro | Phe | Met | Trp | Gly | Gly | Ala | Tyr | Cys | Phe | Cys | Asp |
| | | | 900 | | | | | 905 | | | | | 910 | | |
| Ser | Glu | Asn | Thr | Gln | Leu | Ser | Glu | Ala | Tyr | Val | Asp | Arg | Ser | Asp | Val |
| | | 915 | | | | | 920 | | | | | 925 | | | |
| Cys | Arg | His | Asp | His | Ala | Ser | Ala | Tyr | Lys | Ala | His | Thr | Ala | Ser | Leu |
| | 930 | | | | | 935 | | | | | 940 | | | | |
| Lys | Ala | Lys | Val | Arg | Val | Met | Tyr | Gly | Asn | Val | Asn | Gln | Thr | Val | Asp |

-continued

| 945 | | | | | 950 | | | | | 955 | | | | | 960 |

Val Tyr Val Asn Gly Asp His Ala Val Thr Ile Gly Gly Thr Gln Phe
              965                         970                 975

Ile Phe Gly Pro Leu Ser Ser Ala Trp Thr Pro Phe Asp Asn Lys Ile
              980                       985                 990

Val Val Tyr Lys Asp Glu Val Phe Asn Gln Asp Phe Pro Pro Tyr Gly
        995                      1000                 1005

Ser Gly Gln Pro Gly Arg Phe Gly Asp Ile Gln Ser Arg Thr Val Glu
    1010                     1015                 1020

Ser Asn Asp Leu Tyr Ala Asn Thr Ala Leu Lys Leu Ala Arg Pro Ser
1025                   1030                 1035                 1040

Pro Gly Met Val His Val Pro Tyr Thr Gln Thr Pro Ser Gly Phe Lys
              1045                     1050                 1055

Tyr Trp Leu Lys Glu Lys Gly Thr Ala Leu Asn Thr Lys Ala Pro Phe
            1060                     1065                 1070

Gly Cys Gln Ile Lys Thr Asn Pro Val Arg Ala Met Asn Cys Ala Val
        1075                      1080                 1085

Gly Asn Ile Pro Val Ser Met Asn Leu Pro Asp Ser Ala Phe Thr Arg
    1090                     1095                 1100

Ile Val Glu Ala Pro Thr Ile Ile Asp Leu Thr Cys Thr Val Ala Thr
1105                   1110                 1115                 1120

Cys Thr His Ser Ser Asp Phe Gly Gly Val Leu Thr Leu Thr Tyr Lys
              1125                     1130                 1135

Thr Asn Lys Asn Gly Asp Cys Ser Val His Ser His Ser Asn Val Ala
            1140                     1145                 1150

Thr Leu Gln Glu Ala Thr Ala Lys Val Lys Thr Ala Gly Lys Val Thr
    1155                     1160                 1165

Leu His Phe Ser Thr Ala Ser Ala Ser Pro Ser Phe Val Val Ser Leu
    1170                     1175                 1180

Cys Ser Ala Arg Ala Thr Cys Ser Ala Ser Cys Glu Pro Pro Lys Asp
1185                   1190                 1195                 1200

His Ile Val Pro Tyr Ala Ala Ser His Ser Asn Val Val Phe Pro Asp
              1205                     1210                 1215

Met Ser Gly Thr Ala Leu Ser Trp Val Gln Lys Ile Ser Gly Gly Leu
            1220                     1225                 1230

Gly Ala Phe Ala Ile Gly Ala Ile Leu Val Leu Val Val Val Thr Cys
    1235                     1240                 1245

Ile Gly Leu Arg Arg
    1250

( 2 ) INFORMATION FOR SEQ ID NO:4:

( i ) SEQUENCE CHARACTERISTICS:
        ( A ) LENGTH: 115 base pairs
        ( B ) TYPE: nucleic acid
        ( C ) STRANDEDNESS: single
        ( D ) TOPOLOGY: linear ( i i ) MOLECULE TYPE: RNA (genomic)

Figure 8A:
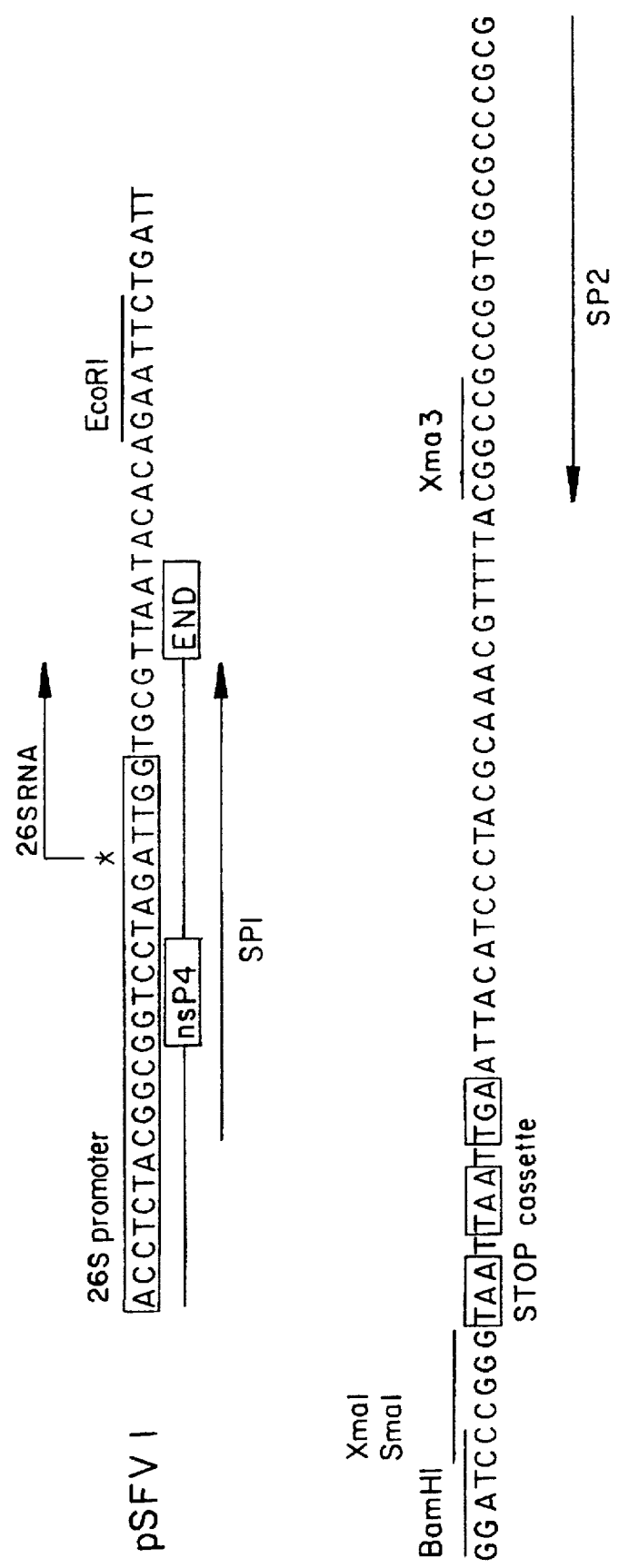
FIG. 8A–8C show the polylinker region of SFV vector plasmids pSFV2 and pSFV3 (SEQ ID NO:4,5 and 6); the position of the promoter for the subgenomic 26S RNA is boxed, and the first nucleotide to be transcribed is indicated by an asterisk.
Figure 8B:
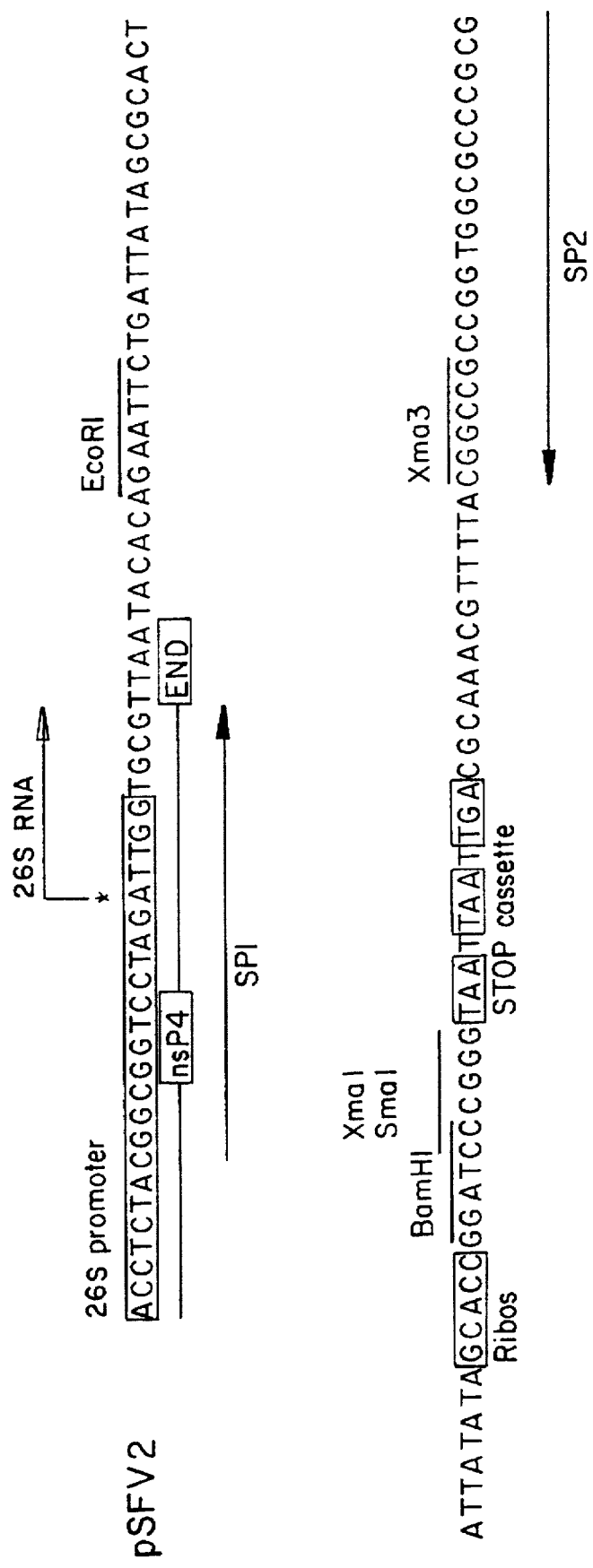
Figure 8C:
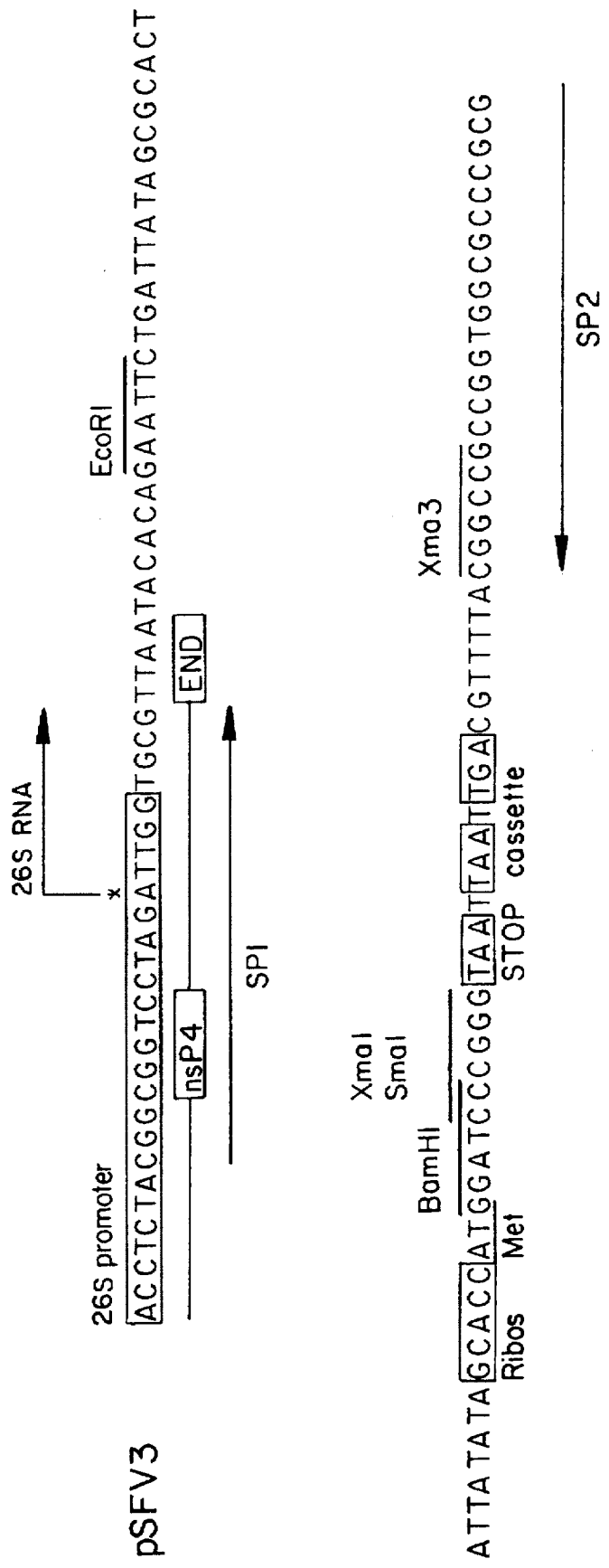

( i i i ) HYPOTHETICAL: NO ( i v ) ANTI-SENSE: NO ( i x ) FEATURE:
        ( A ) NAME/KEY: -
        ( B ) LOCATION: 1..115
        ( D ) OTHER INFORMATION: /label=26S_region
            / note="26S promoter and transcription start and
            proximal downstream region of pSFV1; Figure 8."

( i x ) FEATURE:
    ( A ) NAME/KEY: misc_feature
    ( B ) LOCATION: 1..24
    ( D ) OTHER INFORMATION: /product="26S promoter region"

( x i ) SEQUENCE DESCRIPTION: SEQ ID NO:4:

```
ACCTCTACGG CGGTCCTAGA TTGGTGCGTT AATACACAGA ATCTGATTGG ATCCCGGGTA      60
ATTAATTGAA TTACATCCCT ACGCAAACGT TTTACGGCCG CCGGTGGCGC CCGCG          115
```

( 2 ) INFORMATION FOR SEQ ID NO:5:

( i ) SEQUENCE CHARACTERISTICS:
        ( A ) LENGTH: 127 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( i x ) FEATURE:
        ( A ) NAME/KEY: -
        ( B ) LOCATION: 1..127
        ( D ) OTHER INFORMATION: /label=26S_region
            / note="26S promoter and transcription start and
            proximal downstream region of pSFV2; Figure 8."

( i x ) FEATURE:
        ( A ) NAME/KEY: misc_feature
        ( B ) LOCATION: 1..24
        ( D ) OTHER INFORMATION: /product="26S promoter region"

( x i ) SEQUENCE DESCRIPTION: SEQ ID NO:5:

```
ACCTCTACGG CGGTCCTAGA TTGGTGCGTT AATACACAGA ATTCTGATTA TAGCGCACTA      60
TTATATAGCA CCGGATCCCG GGTAATTAAT TGACGCAAAC GTTTACGGC CGCCGGTGGC      120
GCCCGCG                                                                127
```

( 2 ) INFORMATION FOR SEQ ID NO:6:

( i ) SEQUENCE CHARACTERISTICS:
        ( A ) LENGTH: 123 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( i x ) FEATURE:
        ( A ) NAME/KEY: -
        ( B ) LOCATION: 1..123
        ( D ) OTHER INFORMATION: /label=26S_region
            / note="26S promoter and transcription start and
            proximal downstream region of pSFV3; Figure 8."

( i x ) FEATURE:
        ( A ) NAME/KEY: misc_feature
        ( B ) LOCATION: 1..24
        ( D ) OTHER INFORMATION: /product="26S promoter region"

( x i ) SEQUENCE DESCRIPTION: SEQ ID NO:6:

```
ACCTCTACGG CGGTCCTAGA TTGGTGCGTT AATACACAGA ATTCTGATTA TAGCGCACTA      60
TTATATAGCA CCATGGATCC CGGGTAATTA ATTGACGTTT TACGGCCGCC GGTGGCGCCC     120
```

GCG                                                                                                                                      1 2 3

( 2 ) INFORMATION FOR SEQ ID NO:7:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( v i ) ORIGINAL SOURCE:
        ( A ) ORGANISM: Semliki Forest Virus ( i x ) FEATURE:
        ( A ) NAME/KEY: -
        ( B ) LOCATION: 1..54
        ( D ) OTHER INFORMATION: /label=restrict_site
            / note="sequence of SFV E2 genome in vicinity of Bam H1 s
            vector E2; Figure 12."

( i x ) FEATURE:
        ( A ) NAME/KEY: CDS
        ( B ) LOCATION: 1..54

( x i ) SEQUENCE DESCRIPTION: SEQ ID NO:7:

```
AAC  TCA  CCT  TTC  GTC  CCG  AGA  GCC  GAC  GAA  CCG  GCT  AGA  AAA  GGC  AAA        4 8
Asn  Ser  Pro  Phe  Val  Pro  Arg  Ala  Asp  Glu  Pro  Ala  Arg  Lys  Gly  Lys
 1              5                    10                      15

GTC  CAT                                                                                5 4
Val  His
```

( 2 ) INFORMATION FOR SEQ ID NO:8:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Asn  Ser  Pro  Phe  Val  Pro  Arg  Ala  Asp  Glu  Pro  Ala  Arg  Lys  Gly  Lys
 1              5                    10                      15

Val  His
```

( 2 ) INFORMATION FOR SEQ ID NO:9:

( i ) SEQUENCE CHARACTERISTICS:
        ( A ) LENGTH: 46 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HIV ( i x ) FEATURE:
        ( A ) NAME/KEY: -
        ( B ) LOCATION: 1..46
        ( D ) OTHER INFORMATION: /label=fragment
            / note="HIV gp120 epitope introduced into SFV
            vector E2; Figure 12."

( i x ) FEATURE:
      ( A ) NAME/KEY: CDS
      ( B ) LOCATION: 1..45

( x i ) SEQUENCE DESCRIPTION: SEQ ID NO:9:

```
GAT CCG CGT ATC CAG AGA GGA CCA GGA AGA GCA TTT GTT GAG CTA       45
Asp Pro Arg Ile Gln Arg Gly Pro Gly Arg Ala Phe Val Glu Leu
 1               5                  10                  15

G                                                                 46
```

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Asp Pro Arg Ile Gln Arg Gly Pro Gly Arg Ala Phe Val Glu Leu
 1               5                  10                  15
```

( 2 ) INFORMATION FOR SEQ ID NO:11:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: -
        ( B ) LOCATION: 1..51
        ( D ) OTHER INFORMATION: /label=chimaeric_seq
        / note="SFV-HIV chimaeric sequence shown in Figure 12."

( i x ) FEATURE:
        ( A ) NAME/KEY: CDS
        ( B ) LOCATION: 1..51
        ( D ) OTHER INFORMATION: /product="SFV-HIV chimaeric sequence"

( x i ) SEQUENCE DESCRIPTION: SEQ ID NO:11:

```
GAG GAT CCG CGT ATC CAG AGA GGA CCA GGA AGA GCA TTT GTT GAG GAT   48
Glu Asp Pro Arg Ile Gln Arg Gly Pro Gly Arg Ala Phe Val Glu Asp
 1               5                  10                  15

CCG                                                               51
Pro
```

( 2 ) INFORMATION FOR SEQ ID NO:12:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Glu Asp Pro Arg Ile Gln Arg Gly Pro Gly Arg Ala Phe Val Glu Asp
 1               5                  10                  15

Pro
```

( 2 ) INFORMATION FOR SEQ ID NO:13:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..60
        ( D ) OTHER INFORMATION: /label=oligonucleotide
            / note="used to introduce new linker site"

( x i ) SEQUENCE DESCRIPTION: SEQ ID NO:13:

```
CGGCCAGTGA ATTCTGATTG GATCCGGGT AATTAATTGA ATTACATCCC TACGCAAACG        60
```

( 2 ) INFORMATION FOR SEQ ID NO:14:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..62
        ( D ) OTHER INFORMATION: /label=oligonucleotide
            / note="used to introduce new linker site"

( x i ) SEQUENCE DESCRIPTION: SEQ ID NO:14:

```
GCGCACTATT ATAGCACCGG CTCCCGGGTA ATTAATTGAC GCAAACGTTT TACGGCCGCC        60
GG                                                                      62
```

( 2 ) INFORMATION FOR SEQ ID NO:15:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..62
        ( D ) OTHER INFORMATION: /label=oligonucleotide
            / note="used to introduce new linker site"

( x i ) SEQUENCE DESCRIPTION: SEQ ID NO:15:

```
GCGCACTATT ATAGCACCAT GGATCCGGGT AATTAATTGA CGTTTTACGG CCGCCGGTGG        60
CG                                                                      62
```

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..21
        ( D ) OTHER INFORMATION: /label=primer
                / note="SP1 upstream sequencing primer"

( x i ) SEQUENCE DESCRIPTION: SEQ ID NO:16:

CGGCGGTCCT AGATTGGTGC G                          21

( 2 ) INFORMATION FOR SEQ ID NO:17:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: YES ( i x ) FEATURE:
            ( A ) NAME/KEY: -
            ( B ) LOCATION: 1..21
            ( D ) OTHER INFORMATION: /label=primer
                    / note="SP2 downstream sequencing primer"

( x i ) SEQUENCE DESCRIPTION: SEQ ID NO:17:

CGCGGGCGCC ACCGGCGGCC G                          21

( 2 ) INFORMATION FOR SEQ ID NO:18:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: YES ( i x ) FEATURE:
            ( A ) NAME/KEY: -
            ( B ) LOCATION: 1..21
            ( D ) OTHER INFORMATION: /label=primer
                    / note="primer-1 for first strand cDNA synthesis"

( x i ) SEQUENCE DESCRIPTION: SEQ ID NO:18:

TTTCTCGTAG TTCTCCTCGT C                          21

( 2 ) INFORMATION FOR SEQ ID NO:19:

( i ) SEQUENCE CHARACTERISTICS:
            ( A ) LENGTH: 27 base pairs
            ( B ) TYPE: nucleic acid
            ( C ) STRANDEDNESS: single ( D ) TOPOLOGY: linear ( i i ) MOLECULE TYPE: DNA (genomic)

( i i i ) HYPOTHETICAL: NO ( i v ) ANTI-SENSE: YES ( i x ) FEATURE:
    ( A ) NAME/KEY: -
    ( B ) LOCATION: 1..27
    ( D ) OTHER INFORMATION: /label=primer
        / note="primer-2 for first strand cDNA synthesis"

( x i ) SEQUENCE DESCRIPTION: SEQ ID NO:19:

GTTATCCCAG TGGTTGTTCT CGTAATA                                           27

( 2 ) INFORMATION FOR SEQ ID NO:20:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: -
    ( B ) LOCATION: 1..28
    ( D ) OTHER INFORMATION: /label=primer
        / note="5'most primer for second strand cDNA
        synthesis, equals bp 1-28 of SFV sequence"

( x i ) SEQUENCE DESCRIPTION: SEQ ID NO:20:

ATGGCGGATG TGTGACATAC ACGACGCC                                        28

( 2 ) INFORMATION FOR SEQ ID NO:21:

( i ) SEQUENCE CHARACTERISTICS:
    ( A ) LENGTH: 46 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i x ) FEATURE:
    ( A ) NAME/KEY: -
    ( B ) LOCATION: 1..46
    ( D ) OTHER INFORMATION: /label=adaptor
        / note="5'-sticky end
        ( E c o R I - H i n d I I I - N o t I - X m a I I I - S p e I ) blunt end-3'
        adaptor"

( x i ) SEQUENCE DESCRIPTION: SEQ ID NO:21:

AATTCAAGCT TGCGGCCGCA CTAGTGTTCG AACGCCGGCG TGATCA                  46

( 2 ) INFORMATION FOR SEQ ID NO:22:

( i ) SEQUENCE CHARACTERISTICS:
    ( A ) LENGTH: 8 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: -
    ( B ) LOCATION: 1..8
    ( D ) OTHER INFORMATION: /label=oligonucleotide
        / note="NcoI oligonucleotide"

( x i ) SEQUENCE DESCRIPTION: SEQ ID NO:22:

GCCATGGC        8

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..20
        ( D ) OTHER INFORMATION: /label=oligonucleotide
            / note="oligonucleotide used for screening by
            colony hybridization"

( x i ) SEQUENCE DESCRIPTION: SEQ ID NO:23:

GGTGACACTA TAGCCATGGC        20

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..24
        ( D ) OTHER INFORMATION: /label=oligonucleotide
            / note="site-directed mutagenic oligonucleotide
            used to introduce a BamHI site into the SFV
            genome"

( x i ) SEQUENCE DESCRIPTION: SEQ ID NO:24:

GATCGGCCTA GGAGCCGAGA GCCC        24

( 2 ) INFORMATION FOR SEQ ID NO:25:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO

-continued (iv) ANTI-SENSE: NO (vi) ORIGINAL SOURCE:
    (A) ORGANISM: Semliki Forest Virus (ix) FEATURE:
    (A) NAME/KEY: -
    (B) LOCATION: 1..80
    (D) OTHER INFORMATION: /label=terminator
        / note="3'terminal sequence of cDNA expression
        vector complementary to alphavirus genomic RNA"

(xi) SEQUENCE DESCRIPTION: SEQ ID NO:25:

```
TTTCCAAAAA AAAAAAAAAA AAAAAAAAAA AAAAAAAAAA AAAAAAAAAA AAAAAAAAAA    60

AAAAAAAAAA AAAAACTAGT                                                80
```

(2) INFORMATION FOR SEQ ID NO:26:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (ii) MOLECULE TYPE: RNA (genomic)

(iii) HYPOTHETICAL: NO (vi) ORIGINAL SOURCE:
    (A) ORGANISM: Semliki Forest Virus (ix) FEATURE:
    (A) NAME/KEY: -
    (B) LOCATION: 1..54
    (D) OTHER INFORMATION: /label=restrict_site
        / note="sequence of SFV vector E2 in vicinity of Bam HI
        site; 12."

(ix) FEATURE:
    (A) NAME/KEY: mutation
    (B) LOCATION: 27..32
    (D) OTHER INFORMATION: /label=restriction_sit
        / note="BamHI recognition sequence introduced into
        SFV E2 genome in SFV vector E2."

(ix) FEATURE:
    (A) NAME/KEY: CDS
    (B) LOCATION: 1..54

(xi) SEQUENCE DESCRIPTION: SEQ ID NO:26:

```
AAC TCA CCT TTC GTC CCG AGA GCC GAG GAT CCG GCT AGA AAA GGC AAA    48
Asn Ser Pro Phe Val Pro Arg Ala Glu Asp Pro Ala Arg Lys Gly Lys
 1               5                  10                  15

GTC CAT                                                             54
Val His
```

(2) INFORMATION FOR SEQ ID NO:27:

(i) SEQUENCE CHARACTERISTICS:
    (A) LENGTH: 18 amino acids
    (B) TYPE: amino acid
    (D) TOPOLOGY: linear (ii) MOLECULE TYPE: protein (xi) SEQUENCE DESCRIPTION: SEQ ID NO:27:

```
Asn Ser Pro Phe Val Pro Arg Ala Glu Asp Pro Ala Arg Lys Gly Lys
 1               5                  10                  15

Val His
```

We claim:

1. A recombinant RNA molecule which can be efficiently translated and replicated in an animal host cell, comprising a Semliki Forest Virus RNA genome and an exogenous RNA sequence, wherein said Semliki Forest Virus RNA genome contains at least one deletion or stop codon mutation such that at least one structural protein of the Semliki Forest Virus cannot be made upon introduction of said recombinant RNA into said host cell, and further wherein said exogenous RNA sequence is operatively inserted into a region of the Semliki Forest Virus RNA genome which is non-essential to replication of the recombinant RNA molecule such that the exogenous RNA is expressed from a Semliki Forest Virus transcriptional promoter when the recombinant RNA is introduced into a host cell and further such that the exogenous RNA expresses its biological function in said host cell.

2. The recombinant RNA of claim 1, wherein the exogenous RNA sequence encodes a protein, a polypeptide or a peptide sequence defining an exogenous antigenic epitope or determinant.

3. The recombinant RNA of claim 1, wherein the Semliki Forest Virus genome RNA comprises a 5'-terminal portion, at least one region coding for non-structural proteins required for replication of the Semliki Forest Virus RNA genome, the subgenome promoter region and a 3'-terminal portion of said Semliki Forest Virus RNA genome.

4. The recombinant RNA of claim 1, wherein the exogenous RNA sequence encodes a peptide or protein and is inserted into the subgenomic 26S RNA of Semliki Forest Virus.

5. A composition comprising the recombinant RNA of claim 1 contained in a particle comprising an alphavirus nucleocapsid and a surrounding membrane, wherein said membrane includes an alphavirus spike protein.

6. A recombinant RNA according to claim 1 having a length effective for packaging into an infectious viral particle comprising wild-type alphavirus structural proteins.

7. A DNA vector comprising a cDNA having one strand complementary to the recombinant RNA of claim 1.

8. The recombinant RNA of claim 1, wherein said exogenous RNA sequence encodes a protein and said biological function is expression of biologically active protein.

9. The recombinant RNA of claim 4, wherein said exogenous RNA sequence is inserted into a portion of the 26S subgenomic RNA selected from the group consisting of a portion of the capsid protein RNA, the p62 RNA, the 6K RNA and the E1 RNA.

10. The recombinant RNA of claim 4, wherein the exogenous RNA sequence encodes a foreign viral epitopic peptide and is inserted into the portion of the Semliki Forest Virus genome encoding the E2 spike protein precursor subunit.

11. A recombinant RNA according to claim 6, wherein said alphavirus structural proteins include all of the nucleocapsid, p62, 6k and E1 proteins of Semliki Forest Virus.

12. A DNA vector of claim 7, further comprising a promoter for transcription of RNA operatively linked to said cDNA such that transcription of said cDNA produces a recombinant RNA molecule which can be efficiently translated and replicated in an animal host cell, said recombinant RNA comprising a Semliki Forest Virus RNA genome and an exogenous RNA sequence, wherein said exogenous RNA sequence is operatively inserted into a region of the alphavirus RNA genome which is non-essential to replication of the recombinant RNA molecule such that the exogenous RNA is expressed from the Semliki Forest Virus transcriptional promoter when said DNA vector is introduced into a host cell and further such that the exogenous RNA expresses its biological function in said host cell.

13. A cell containing a DNA vector according to claim 7.

14. A DNA vector of claim 12, wherein said promoter is an SP6 promoter and said cDNA is located immediately downstream of the SP6 promoter and further wherein said cDNA has a 5'-terminal sequence of ATGG or GATGG and a 3'terminal sequence of TTTCCA$_{69}$ACTAGT.

15. A DNA vector according to claim 12, wherein a portion of said cDNA encoding an alphavirus structural protein is deleted, and further comprising a polylinker, wherein said polylinker is composed of DNA having a nucleotide sequence containing a plurality of restriction enzyme recognition sites.

16. A DNA vector according to claim 12, wherein said cDNA contains a mutation in the region encoding the protease cleavage site in the p62 protein of the Semliki Forest Virus, wherein said mutation results in expression of a p62 protein of Semliki Forest Virus that is not cleavable by intracellular proteases endogenous to said host cell.

17. An RNA molecule made by transcription of a DNA vector of claim 12.

18. A cell containing a DNA vector according to claim 12.

19. A DNA vector according to claim 15, wherein said polylinker is operatively linked to said cDNA so as to allow expression of DNA encoding an exogenous protein in a host cell transformed with said DNA vector.

20. A DNA vector according to claim 15 wherein said polylinker is inserted into the region of the cDNA encoding the p62 spike protein.

21. A DNA vector according to claim 19, wherein said restriction enzyme recognition sites are sites for the enzymes BamHI, SmaI and XmaI.

22. A DNA vector according to claim 19, wherein said polylinker is operatively linked to said cDNA so as to allow expression of DNA encoding an exogenous protein as a part of an alphavirus structural protein.

23. A DNA vector of claim 16, wherein the cell-entry activity of said p62 protein can be activated by treatment with a protease in vitro.

24. A cell containing a DNA vector according to claim 16.

25. A DNA vector of claim 23, wherein said protease is trypsin or chymotrypsin.

26. A DNA vector of claim 23, which is selected from the group consisting of pSFV1, pSFV2 and pSFV3.

27. A helper vector comprising a cDNA encoding an alphavirus RNA which expresses at least one alphavirus structural protein and wherein said alphavirus RNA lacks sequences encoding RNA signals for packaging of RNA into alphavirus particles, but contains the 5' and 3' nucleotides needed for replication of the alphavirus RNA in a host cell and also contains nucleotides encoding a promoter for transcription of said DNA encoding said alphavirus structural protein in said host cell.

28. A helper vector of claim 27, wherein the nucleotides needed for replication are the replication sequences from Semliki Forest Virus and the structural protein sequences and promoter sequences are encoded by and direct transcription of, respectively, the Semliki Forest Virus 26S mRNA.

29. A helper vector of claim 27, wherein said cDNA comprises the nucleotides 1 to 308, inclusive, and 6400 to 11517, inclusive, of Sequence I.D. No. 1.

30. A helper vector of claim 27, wherein said structural protein is functionally homologous to a protein selected from the group consisting of the nucleocapsid, p62, 6k and E1 proteins of Semliki Forest Virus.

31. A helper vector of claim 27, wherein said cDNA contains a mutation in the protease cleavage site in the alphavirus structural protein homologous in function to the p62 protein of the Semliki Forest Virus, wherein said mutation results in expression of a p62-homologous protein that is not cleavable by intracellular proteases endogenous to said host cell.

32. A helper vector of claim 27, wherein said structural protein is the p62 protein of Semliki Forest Virus.

33. A cell containing a helper vector according to claim 27.

34. The helper vector of claim 28, wherein said cDNA comprises the nucleotides 1 to 308, inclusive, and 6400 to 11517, inclusive, of Sequence I.D. No. 1.

35. A helper vector of claim 28, wherein said structural protein is a protein selected from the group consisting of the nucleocapsid, p62, 6k and E1 proteins.

36. A helper vector of claim 28, wherein said cDNA contains a mutation in the protease cleavage site in the p62 protein, wherein said mutation results in expression of a p62 protein that is not cleavable by intracellular proteases endogenous to said host cell.

37. A cell containing a helper vector according to claim 31.

38. A helper vector of claim 32, wherein said cDNA contains a mutation in the protease cleavage site in the p62 protein, wherein said mutation results in expression of a p62 protein that is not cleavable by intracellular proteases endogenous to said host cell.

39. A method for producing recombinant alphavirus particles containing a recombinant alphavirus genome, comprising transfecting a host cell with;

a first vector comprising a cDNA encoding an alphavirus RNA which expresses at least one alphavirus structural protein and wherein said alphavirus RNA lacks sequences encoding RNA signals for packaging of RNA into alphavirus nucleocapsid particles, but contains the 5' and 3' nucleotides needed for replication of the alphavirus RNA in a host cell and also contains nucleotides encoding a promoter for transcription of said DNA encoding said alphavirus structural protein in said host cell; and a second DNA vector comprising a cDNA encoding a recombinant alphavirus RNA genome, wherein said recombinant alphavirus RNA genome contains at least one deletion or stop codon mutation in the region encoding said structural protein encoded by said first vector, such that said structural protein that is encoded by said first vector cannot be made upon introduction of said second DNA vector into said host cell, and encoding all other structural proteins needed for assembly of an alphavirus particle, so that said other structural proteins are expressed in said host cell, and further wherein an exogenous RNA sequence, encoding said exogenous protein, is operatively inserted into a region of the recombinant alphavirus RNA genome which is non-essential to replication of the recombinant alphavirus RNA genome such that the exogenous RNA is capable of expressing said exogenous protein in said host cell;

allowing assembly of said recombinant alphavirus particles from structural proteins expressed by said first and second vectors; and recovering said recombinant alphavirus particles from cultures of said host cell.

40. A cell according to claim 18, which is a stably transformed animal cell.

41. A cell according to claim 24, which is a stably transformed animal cell.

42. A cell according to claim 40, wherein said animal cell is a BHK cell.

43. A cell according to claim 41, wherein said animal cell is a BHK cell.

44. A chimeric alphavirus comprising an alphavirus structural protein containing an amino acid sequence which is exogenous to said alphavirus and wherein said structural protein containing said exogenous amino acid sequence is packaged into chimeric viral particle.

45. A chimeric alphavirus according to claim 44, wherein said exogenous amino acid sequence is contained within a structural protein that is functionally homologous to the p62 protein of Semliki Forest Virus.

46. The chimeric virus of claim 44, wherein said alphavirus is Semliki Forest Virus.

47. A chimeric alphavirus according to claim 45 wherein said structural protein is the p62 protein of Semliki Forest Virus.

48. A chimeric alphavirus according to claim 47, wherein said alphavirus is Semliki Forest Virus.

* * * * *